(12) United States Patent
Havenstrite et al.

(10) Patent No.: US 10,525,170 B2
(45) Date of Patent: Jan. 7, 2020

(54) MEDICAL DEVICE COATING WITH A BIOCOMPATIBLE LAYER

(71) Applicant: TANGIBLE SCIENCE, LLC, Redwood City, CA (US)

(72) Inventors: Karen Havenstrite, San Francisco, CA (US); Victor W. McCray, San Jose, CA (US); Brandon M. Felkins, Half Moon Bay, CA (US); Paul Cook, Palo Alto, CA (US)

(73) Assignee: Tangible Science, LLC, Redwood City, CA (US)

( * ) Notice: Subject to any disclaimer, the term of this patent is extended or adjusted under 35 U.S.C. 154(b) by 0 days.

(21) Appl. No.: 15/533,744

(22) PCT Filed: Dec. 9, 2015

(86) PCT No.: PCT/US2015/064743
§ 371 (c)(1),
(2) Date: Jun. 7, 2017

(87) PCT Pub. No.: WO2016/094533
PCT Pub. Date: Jun. 16, 2016

(65) Prior Publication Data
US 2017/0360994 A1 Dec. 21, 2017

Related U.S. Application Data

(60) Provisional application No. 62/089,734, filed on Dec. 9, 2014.

(51) Int. Cl.
| | |
|---|---|
| *A61L 29/14* | (2006.01) |
| *A61L 27/34* | (2006.01) |
| *A61L 27/52* | (2006.01) |
| *A61L 27/54* | (2006.01) |
| *A61L 29/08* | (2006.01) |
| *A61L 29/16* | (2006.01) |
| *A61L 31/10* | (2006.01) |
| *A61L 31/14* | (2006.01) |
| *A61L 31/16* | (2006.01) |
| *A61L 15/46* | (2006.01) |
| *A61L 15/60* | (2006.01) |

(52) U.S. Cl.
CPC ............ *A61L 29/145* (2013.01); *A61L 15/46* (2013.01); *A61L 15/60* (2013.01); *A61L 27/34* (2013.01); *A61L 27/52* (2013.01); *A61L 27/54* (2013.01); *A61L 29/085* (2013.01); *A61L 29/16* (2013.01); *A61L 31/10* (2013.01); *A61L 31/145* (2013.01); *A61L 31/16* (2013.01); *A61L 2300/104* (2013.01); *A61L 2300/404* (2013.01); *A61L 2400/12* (2013.01)

(58) Field of Classification Search
CPC ........ A61L 29/145; A61L 27/34; A61L 27/52; A61L 27/54; A61L 29/085; A61L 29/16; A61L 31/10; A61L 31/145; A61L 31/16; A61L 15/46; A61L 15/60; A61L 2300/104; A61L 2300/404; A61L 2400/12
See application file for complete search history.

(56) References Cited

U.S. PATENT DOCUMENTS

| | | | |
|---|---|---|---|
| 2,976,576 A | 3/1961 | Wichterle et al. | |
| 3,408,429 A | 10/1968 | Otto | |
| 4,136,250 A | 1/1979 | Mueller et al. | |
| 4,143,949 A | 3/1979 | Chen | |
| 4,153,641 A | 5/1979 | Deichert et al. | |
| 4,182,822 A | 1/1980 | Chang | |
| 4,189,546 A | 2/1980 | Deichert et al. | |
| 4,254,248 A | 3/1981 | Friends et al. | |
| 4,259,467 A | 3/1981 | Keogh et al. | |
| 4,260,725 A | 4/1981 | Keogh et al. | |
| 4,261,875 A | 4/1981 | Leboeuf | |
| 4,276,402 A | 6/1981 | Chromecek et al. | |
| 4,327,203 A | 4/1982 | Deichert et al. | |
| 4,338,419 A * | 7/1982 | Korb ..................... | B29D 11/00 351/159.33 |
| 4,341,889 A | 7/1982 | Deichert et al. | |
| 4,343,927 A | 8/1982 | Chang | |

(Continued)

FOREIGN PATENT DOCUMENTS

| | | |
|---|---|---|
| CN | 1180416 A | 4/1998 |
| CN | 1233191 A | 10/1999 |

(Continued)

OTHER PUBLICATIONS

S. Park, et al, Surface Modification of Poly(ethylene terephthalate) Angioplasty Balloons with a Hydrophilic Poly(acrylamide-co-ethylene glycol) Interpenetrating Polymer Network Coating, 53 J Biomed. Mater. (Year: 2000).*

(Continued)

*Primary Examiner* — Sean M Basquill
(74) *Attorney, Agent, or Firm* — Shay Glenn LLP

(57) ABSTRACT

Medical devices with a hydrogel layer covalently attached to a portion of the outer surface of the medical device are provided along with methods for applying the coating. The hydrogel layer can include a first polymer species comprising polyethylene glycol (PEG) and a second polymer species. Examples of the second polymer species include PEG and polyacrylamide (PAM). The first and second species can be at least partially cross-linked. Methods for forming the hydrogel coatings on the medical devices are provided including nucleophilic conjugate reactions, such as Click reactions.

29 Claims, 18 Drawing Sheets

(56) References Cited

U.S. PATENT DOCUMENTS

| | | |
|---|---|---|
| 4,347,198 A | 8/1982 | Ohkada et al. |
| 4,355,147 A | 10/1982 | Deichert et al. |
| 4,444,711 A | 4/1984 | Schad |
| 4,460,534 A | 7/1984 | Boehm et al. |
| 4,468,229 A | 8/1984 | Su |
| 4,486,577 A | 12/1984 | Mueller et al. |
| 4,543,398 A | 9/1985 | Bany et al. |
| 4,553,975 A | 11/1985 | Su |
| 4,605,712 A | 8/1986 | Mueller et al. |
| 4,661,575 A | 4/1987 | Tom |
| 4,684,538 A | 8/1987 | Klemarczyk |
| 4,703,097 A | 10/1987 | Wingler et al. |
| 4,833,218 A | 5/1989 | Lee |
| 4,837,289 A | 6/1989 | Mueller et al. |
| 4,929,250 A | 5/1990 | Hung et al. |
| 4,954,586 A | 9/1990 | Toyoshima et al. |
| 4,954,587 A | 9/1990 | Mueller |
| 5,010,141 A | 4/1991 | Mueller |
| 5,034,461 A | 7/1991 | Lai et al. |
| 5,039,761 A | 8/1991 | Ono et al. |
| 5,070,170 A | 12/1991 | Robertson et al. |
| 5,098,445 A | 3/1992 | Hung et al. |
| 5,135,297 A | 8/1992 | Valint |
| 5,135,965 A | 8/1992 | Tahan |
| 5,196,458 A | 3/1993 | Nunez et al. |
| 5,219,965 A | 6/1993 | Valint et al. |
| 5,260,000 A | 11/1993 | Nandu et al. |
| 5,326,584 A | 7/1994 | Kamel et al. |
| 5,346,946 A | 9/1994 | Yokoyama et al. |
| 5,352,714 A | 10/1994 | Lai et al. |
| 5,358,995 A | 10/1994 | Lai et al. |
| 5,409,731 A | 4/1995 | Nakagawa et al. |
| 5,416,132 A | 5/1995 | Yokoyama et al. |
| 5,446,090 A * | 8/1995 | Harris .................. C08G 65/326 525/54.1 |
| 5,451,617 A | 9/1995 | Lai et al. |
| 5,486,579 A | 1/1996 | Lai et al. |
| 5,508,317 A | 4/1996 | Muller |
| 5,583,463 A | 12/1996 | Merritt |
| 5,645,882 A | 7/1997 | Llanos |
| 5,674,942 A | 10/1997 | Hill et al. |
| 5,681,871 A | 10/1997 | Molock et al. |
| 5,760,100 A | 6/1998 | Nicolson et al. |
| 5,805,264 A | 9/1998 | Janssen et al. |
| 5,843,346 A | 12/1998 | Morrill |
| 5,874,500 A | 2/1999 | Rhee et al. |
| 5,894,002 A | 4/1999 | Boneberger et al. |
| 5,962,548 A | 10/1999 | Vanderlaan et al. |
| 5,981,675 A | 11/1999 | Valint et al. |
| 6,019,472 A | 2/2000 | Koester et al. |
| 6,022,553 A | 2/2000 | Anders et al. |
| 6,039,913 A | 3/2000 | Hirt et al. |
| 6,201,065 B1 | 3/2001 | Pathak et al. |
| 6,218,508 B1 | 4/2001 | Kragh et al. |
| 6,309,660 B1 | 10/2001 | Hsu et al. |
| 6,340,465 B1 | 1/2002 | Hsu et al. |
| 6,406,739 B1 | 6/2002 | LeBoeuf et al. |
| 6,428,839 B1 | 8/2002 | Künzler et al. |
| 6,440,571 B1 | 8/2002 | Valint et al. |
| 6,447,920 B1 | 9/2002 | Chadbrecek et al. |
| 6,451,871 B1 | 9/2002 | Winterton et al. |
| 6,458,889 B1 | 10/2002 | Trollsas et al. |
| 6,468,667 B1 | 10/2002 | Chabrecek et al. |
| 6,478,423 B1 | 11/2002 | Turner et al. |
| 6,500,481 B1 | 12/2002 | Vanderlaan et al. |
| 6,623,747 B1 | 9/2003 | Chatelier et al. |
| 6,624,245 B2 | 9/2003 | Wallace et al. |
| 6,627,124 B1 | 9/2003 | Herbrechtsmeier et al. |
| 6,630,243 B2 | 10/2003 | Valint et al. |
| 6,638,563 B2 * | 10/2003 | McGee .................. A61L 27/34 351/159.33 |
| 6,719,929 B2 | 4/2004 | Winterton et al. |
| 6,723,815 B2 | 4/2004 | Callaghan et al. |
| 6,740,116 B2 | 5/2004 | Morcher |
| 6,759,388 B1 | 7/2004 | Marchant et al. |
| 6,762,264 B2 | 7/2004 | Künzler et al. |
| 6,793,973 B2 | 9/2004 | Winterton et al. |
| 6,800,225 B1 | 10/2004 | Hagmann et al. |
| 6,811,259 B2 | 11/2004 | Tucker |
| 6,811,805 B2 | 11/2004 | Gilliard et al. |
| 6,815,074 B2 | 11/2004 | Aguado et al. |
| 6,827,966 B2 | 12/2004 | Qiu et al. |
| 6,852,353 B2 | 2/2005 | Qiu et al. |
| 6,858,248 B2 | 2/2005 | Qiu et al. |
| 6,896,926 B2 | 5/2005 | Qiu et al. |
| 6,940,580 B2 | 9/2005 | Winterton et al. |
| 7,037,517 B2 | 5/2006 | Kataoka et al. |
| 7,053,150 B2 | 5/2006 | Kozlowski et al. |
| 7,091,283 B2 | 8/2006 | Müller et al. |
| 7,132,475 B2 | 11/2006 | Hubbell et al. |
| 7,247,387 B1 | 7/2007 | Huang |
| 7,251,519 B2 | 7/2007 | Axelsson et al. |
| 7,276,474 B2 | 10/2007 | Marchant et al. |
| 7,384,590 B2 | 6/2008 | Kelly et al. |
| 7,402,318 B2 | 7/2008 | Morris et al. |
| 7,507,469 B2 | 3/2009 | Mao et al. |
| 7,642,332 B2 | 1/2010 | Kennedy et al. |
| 7,674,478 B2 | 3/2010 | Kataoka et al. |
| 7,695,775 B2 | 4/2010 | Kobrin et al. |
| 7,833,715 B1 | 11/2010 | Schweitzer et al. |
| 7,847,025 B2 | 12/2010 | Liu et al. |
| 7,857,447 B2 | 12/2010 | Myung et al. |
| 7,857,849 B2 | 12/2010 | Myung et al. |
| 7,858,000 B2 | 12/2010 | Winterton |
| 7,942,929 B2 | 5/2011 | Linhardt et al. |
| 7,955,704 B2 | 6/2011 | Lowery et al. |
| 8,071,121 B2 | 12/2011 | Chauhan et al. |
| 8,083,348 B2 | 12/2011 | Linhardt et al. |
| 8,133,580 B2 | 3/2012 | Dias et al. |
| 8,163,302 B2 | 4/2012 | Marchant et al. |
| 8,178,602 B2 | 5/2012 | Mao et al. |
| 8,309,117 B2 | 11/2012 | Rubner et al. |
| 8,357,760 B2 | 1/2013 | Qiu |
| 8,409,599 B2 | 4/2013 | Wu et al. |
| 8,425,926 B2 | 4/2013 | Qiu et al. |
| 8,480,227 B2 | 7/2013 | Qiu et al. |
| 8,790,678 B2 | 7/2014 | Elbert et al. |
| 8,871,016 B2 | 10/2014 | Trexler et al. |
| 8,871,869 B2 | 10/2014 | Dias et al. |
| 8,906,284 B2 | 12/2014 | Crosby et al. |
| 9,244,195 B2 | 1/2016 | Bauman et al. |
| 9,310,627 B2 | 4/2016 | Havenstrite et al. |
| 9,358,735 B2 | 6/2016 | Bothe et al. |
| 9,395,468 B2 * | 7/2016 | Havenstrite ............ G02B 1/043 |
| 9,395,627 B2 | 7/2016 | Liu et al. |
| 2001/0044021 A1 | 11/2001 | Ogawa et al. |
| 2002/0006493 A1 | 1/2002 | Chabrecek et al. |
| 2002/0057417 A1 | 5/2002 | Galin |
| 2002/0086160 A1 | 7/2002 | Qiu et al. |
| 2002/0155222 A1 | 10/2002 | Caron |
| 2003/0008063 A1 | 1/2003 | Chabrecek et al. |
| 2003/0087099 A1 | 5/2003 | Merill et al. |
| 2004/0067365 A1 | 4/2004 | Qiu |
| 2004/0086479 A1 | 5/2004 | Grinstaff et al. |
| 2004/0108607 A1 | 6/2004 | Winterton et al. |
| 2004/0116564 A1 | 6/2004 | Devlin et al. |
| 2004/0142016 A1 | 7/2004 | Luthra et al. |
| 2004/0181172 A1 | 9/2004 | Carney et al. |
| 2005/0008676 A1 | 1/2005 | Qiu et al. |
| 2005/0053642 A1 | 3/2005 | Ulbricht et al. |
| 2005/0129731 A1 | 6/2005 | Horres et al. |
| 2006/0063852 A1 | 3/2006 | Iwata et al. |
| 2006/0275337 A1 | 12/2006 | Cohen et al. |
| 2006/0290882 A1 | 12/2006 | Meyers et al. |
| 2006/0292701 A1 | 12/2006 | Huang et al. |
| 2007/0001155 A1 | 1/2007 | Walters et al. |
| 2007/0031498 A1 | 2/2007 | Zong et al. |
| 2007/0082019 A1 | 4/2007 | Huang et al. |
| 2007/0087113 A1 | 4/2007 | Uilk et al. |
| 2007/0116741 A1 | 5/2007 | Valint et al. |
| 2007/0122540 A1 * | 5/2007 | Salamone ............ A61L 27/10 427/2.24 |
| 2007/0129792 A1 | 6/2007 | Picart et al. |
| 2007/0197681 A1 | 8/2007 | Lowery et al. |

(56) References Cited

U.S. PATENT DOCUMENTS

| | | |
|---|---|---|
| 2007/0229758 A1 | 10/2007 | Matsuzawa |
| 2008/0002146 A1 | 1/2008 | Stachowski et al. |
| 2008/0015315 A1 | 1/2008 | Chang et al. |
| 2008/0038221 A1 | 2/2008 | Suda et al. |
| 2008/0076851 A1 | 3/2008 | Goldberg et al. |
| 2008/0143003 A1 | 6/2008 | Phelan |
| 2008/0143958 A1 | 6/2008 | Medina et al. |
| 2008/0152685 A1 | 6/2008 | Blackwell et al. |
| 2008/0152800 A1 | 6/2008 | Bothe et al. |
| 2008/0181931 A1 | 7/2008 | Qiu et al. |
| 2008/0203592 A1 | 8/2008 | Qiu et al. |
| 2008/0226922 A1 | 9/2008 | Ferreiro et al. |
| 2008/0231798 A1 | 9/2008 | Zhou et al. |
| 2008/0234457 A1 | 9/2008 | Zhou et al. |
| 2008/0255305 A1 | 10/2008 | Brook et al. |
| 2009/0060981 A1 | 3/2009 | Chauhan |
| 2009/0081275 A1 | 3/2009 | Rolfes et al. |
| 2009/0123519 A1 | 5/2009 | Rolfes et al. |
| 2009/0155595 A1 | 6/2009 | Lee |
| 2010/0013114 A1 | 1/2010 | Bowers et al. |
| 2010/0069522 A1 | 3/2010 | Linhardt et al. |
| 2010/0099852 A1 | 4/2010 | Cassingham et al. |
| 2010/0114042 A1 | 5/2010 | Dias et al. |
| 2010/0120938 A1 | 5/2010 | Phelan et al. |
| 2010/0140114 A1 | 6/2010 | Pruitt et al. |
| 2010/0149482 A1 | 6/2010 | Ammon et al. |
| 2010/0152708 A1 | 6/2010 | Li et al. |
| 2010/0198168 A1 | 8/2010 | Rooijmans |
| 2010/0226963 A1 | 9/2010 | Cooper et al. |
| 2010/0249273 A1 | 9/2010 | Scales et al. |
| 2010/0298446 A1 | 11/2010 | Chang et al. |
| 2011/0133350 A1 | 6/2011 | Qiu et al. |
| 2011/0134387 A1 | 6/2011 | Samuel et al. |
| 2011/0177150 A1 | 7/2011 | Pathak et al. |
| 2011/0189493 A1 | 8/2011 | Ott et al. |
| 2011/0293669 A1 | 12/2011 | Bennett et al. |
| 2011/0293687 A1 | 12/2011 | Bennett et al. |
| 2011/0293688 A1 | 12/2011 | Bennett et al. |
| 2011/0293692 A1 | 12/2011 | Bennett et al. |
| 2011/0293699 A1 | 12/2011 | Bennett et al. |
| 2012/0023869 A1 | 2/2012 | Samuel et al. |
| 2012/0026457 A1 | 2/2012 | Qiu et al. |
| 2012/0026458 A1* | 2/2012 | Qiu ............... G02B 1/043 351/159.33 |
| 2012/0038888 A1 | 2/2012 | Gu et al. |
| 2012/0049689 A1 | 3/2012 | Bennett et al. |
| 2012/0116019 A1 | 5/2012 | Suzuki et al. |
| 2012/0137635 A1 | 6/2012 | Qiu et al. |
| 2012/0139137 A1 | 6/2012 | Qiu |
| 2012/0147323 A1 | 6/2012 | Domschke |
| 2013/0090344 A1 | 4/2013 | Thakur et al. |
| 2013/0095235 A1 | 4/2013 | Bothe et al. |
| 2013/0118127 A1 | 5/2013 | Kolluru et al. |
| 2013/0162943 A1 | 6/2013 | Goodenough et al. |
| 2013/0176529 A1 | 7/2013 | Li et al. |
| 2013/0188124 A1 | 7/2013 | Li et al. |
| 2014/0155313 A1 | 6/2014 | Eggink et al. |
| 2016/0159019 A1 | 6/2016 | Bruce et al. |
| 2016/0161639 A1 | 6/2016 | Scales et al. |
| 2016/0216534 A1 | 7/2016 | Legerton et al. |
| 2016/0223836 A1 | 8/2016 | Havenstrite et al. |
| 2016/0320635 A1 | 11/2016 | Havenstrite et al. |
| 2017/0160432 A1 | 6/2017 | Havenstrite et al. |
| 2017/0242269 A1 | 8/2017 | Havenstrite et al. |

FOREIGN PATENT DOCUMENTS

| | | |
|---|---|---|
| CN | 1602228 A | 3/2005 |
| CN | 1961223 A | 5/2007 |
| CN | 101096451 A | 1/2008 |
| CN | 101688042 A | 3/2010 |
| CN | 101726864 A | 6/2010 |
| CN | 102323629 A | 1/2012 |
| CN | 103254436 A | 8/2013 |
| CN | 103547585 A | 1/2014 |
| EP | 0807140 A1 | 11/1997 |
| EP | 808222 B1 | 5/1999 |
| EP | 1251973 A1 | 10/2002 |
| EP | 1319037 A1 | 6/2003 |
| EP | 0906122 B1 | 9/2003 |
| EP | 1412404 A1 | 4/2004 |
| EP | 1268621 B1 | 11/2005 |
| EP | 0876165 B1 | 6/2006 |
| EP | 1744836 A2 | 1/2007 |
| EP | 1427532 B1 | 2/2007 |
| EP | 0918550 B1 | 4/2007 |
| EP | 2061526 A2 | 5/2009 |
| EP | 1261557 B1 | 11/2009 |
| EP | 1458797 B1 | 12/2009 |
| EP | 2187980 A1 | 5/2010 |
| EP | 2219865 A2 | 8/2010 |
| EP | 2389895 A2 | 11/2011 |
| EP | 2443482 A2 | 4/2012 |
| EP | 1355965 B1 | 9/2012 |
| EP | 1932874 B1 | 2/2013 |
| EP | 2461767 B1 | 5/2013 |
| EP | 2455104 B1 | 7/2013 |
| EP | 2624871 A2 | 8/2013 |
| JP | H09-507784 A | 8/1997 |
| JP | 2000512677 A | 9/2000 |
| JP | 2001131271 A | 5/2001 |
| JP | 2001518528 A | 10/2001 |
| JP | 2003527890 A | 9/2003 |
| JP | 2005520703 A | 7/2005 |
| JP | 2006508720 A | 3/2006 |
| JP | 2008511870 A | 4/2006 |
| WO | WO93/00391 A1 | 1/1993 |
| WO | WO98/28026 A1 | 7/1998 |
| WO | WO99/55742 A1 | 11/1999 |
| WO | WO01/05578 A1 | 1/2001 |
| WO | WO01/32230 A2 | 5/2001 |
| WO | WO01/44861 A1 | 6/2001 |
| WO | WO01/57118 A2 | 8/2001 |
| WO | WO01/92924 A1 | 12/2001 |
| WO | WO02/16974 A2 | 2/2002 |
| WO | WO02/096477 A2 | 12/2002 |
| WO | WO02/097481 A1 | 12/2002 |
| WO | WO03/041754 A1 | 5/2003 |
| WO | WO03/057270 A1 | 7/2003 |
| WO | WO03/075888 A2 | 9/2003 |
| WO | WO2004/024203 A1 | 3/2004 |
| WO | WO2004/025332 A1 | 3/2004 |
| WO | WO2004/056403 A2 | 7/2004 |
| WO | WO2004/056404 A2 | 7/2004 |
| WO | WO2004/080297 A1 | 9/2004 |
| WO | WO2005/014074 A1 | 2/2005 |
| WO | WO2005/035607 A1 | 4/2005 |
| WO | WO2007/002671 A1 | 1/2007 |
| WO | WO2007/146137 A2 | 12/2007 |
| WO | WO2008/024071 A1 | 2/2008 |
| WO | WO2008/079809 A2 | 7/2008 |
| WO | WO2008/094876 A1 | 8/2008 |
| WO | WO2008/130604 A2 | 10/2008 |
| WO | WO2008/156604 A1 | 12/2008 |
| WO | WO2009/055082 A2 | 4/2009 |
| WO | WO2009/094368 A1 | 7/2009 |
| WO | WO2010/003078 A2 | 1/2010 |
| WO | WO2010/011492 A1 | 1/2010 |
| WO | WO2010/018293 A1 | 2/2010 |
| WO | WO2010/056686 A1 | 5/2010 |
| WO | WO2010/065686 A1 | 6/2010 |
| WO | WO2010/065960 A2 | 6/2010 |
| WO | WO2010/103089 A1 | 9/2010 |
| WO | WO2011/007454 A1 | 1/2011 |
| WO | WO2011/056761 A1 | 5/2011 |
| WO | WO2011/071790 A1 | 6/2011 |
| WO | WO2011/071791 A1 | 6/2011 |
| WO | WO2012/035598 A1 | 3/2012 |
| WO | WO2012/149256 A2 | 4/2012 |
| WO | WO2012/055884 A1 | 5/2012 |
| WO | WO2012/074859 A1 | 6/2012 |
| WO | WO2012/082704 A1 | 6/2012 |
| WO | WO2012/153072 A1 | 11/2012 |

(56) References Cited

FOREIGN PATENT DOCUMENTS

| WO | WO2013/055746 A1 | 4/2013 |
|---|---|---|
| WO | WO2013/074535 A1 | 5/2013 |
| WO | WO2013/166358 A1 | 11/2013 |
| WO | WO2014/035912 A1 | 3/2014 |
| WO | WO2015/031196 A1 | 3/2015 |
| WO | WO2016/026884 A1 | 2/2016 |
| WO | WO2016/100557 A2 | 6/2016 |

OTHER PUBLICATIONS

Myrto Korogiannaki, Jianfeng Zhang, Heather Sheardown, Surface Modification of Model Hydrogel Contact Lenses with Hyaluronic Acid via Thiol-ene "Click" Chemistry for Enhancing Surface Characteristics, 32 J Biomat. Appl. 446 (Year: 2017).*

Bearinger et al.; P(Aam-co-EG) interpenetrating polymer networks grafted to oxide surfaces: surface characterization, protein adsorption, and cell detachment studies; Langmuir; 13(19); pp. 5175-5183; Sep. 17, 1997.

Bundgaard et al.; N-Sulfonyl imidates as a novel prodrug form for an ester function or a sulfonamide group; J Med Chem; 31(11); pp. 2066-2069; Nov. 1988.

Chang et al.; U.S. Appl. No. 61/180,453 entitled "Actinically-crosslinkable siloxane-containing copolymers," filed May 22, 2009.

Dilsiz et al.; Plasma Polymerization of Selected Organic Compounds; Polymer; 37(2); pp. 333-342; Jan. 1996.

Ghormely; The advent contact lens-clinical viewpoints; 3 pages; retrieved from http://www.sciencedirect.com/science/article/pii/0892896789900321/pdf?md5=5ff798a43537ff29c508eb02d36dd&pid=1-2.0-0892896789900321-main.pdf on May 23, 2017.

Greene et al.; Protective Groups in Organic Synthesis; 2nd Ed.; John Wiley & Sons; New York, NY; pp. 178-210; Oct. 1991.

Hermanson; Chapter 3: The Reactions of Bioconjugation; in Bioconjugate Techniques; 3rd Ed.; Academic Press, San Diego, CA; pp. 229-258; Sep. 2013.

Justynska et al.; U.S. Appl. No. 61/180,449 entitled "Actinically-crosslinkable siloxane-containing copolymers," filed May 22, 2009.

Keana et al.; New Reagents for Photoaffinity Labeling: Synthesis and Photolysis of Functionalized Perfluorophenyl Azides; J. Org. Chem.; 55(11); pp. 3640-3647; May 1990.

Park et al.; Surface modifications of poly(ethylene terephthalate) angioplasty balloons with a hydrophilic poly (acrylamide-co-ethylene glycol) interpenetrating polymer network coating; J. Biomed. Mater. Res.; 53(5); pp. 568-576; Sep. 1, 2000.

Petracek et al.; Hydroxymethylketones as pro-drugs; Annals NY Acad Sci; 507; pp. 353-354; Dec. 1987.

Yamada et al.;Selective modification of aspartic acid-101 in lysozyme by carbodiimide reaction; Biochemistry; 20(17); pp. 4836-4842; Aug. 1981.

Yasuda; Glow discharge polymerization; Journal of Polymer Science: Macromolecular Reviews; 16(1); pp. 199-293; 1981.

Kayaman et al.; Phase transition of polyacrylamide gels in PEG solutions; Polymer Gels and Networks; 5(2); pp. 167-184; Apr. 1997.

Pantar; The polymerization of acrylamide in the presence of poly (ethylene glycol) II; European Polymer Journal; 22(11); pp. 939-942; Jan. 1986.

Fiedler Encyclopedia of Excipients for Pharmaceuticals, Cosmetics and Related Areas; Ed. E.M. Hoepfner; vol. 2 (L-Z); 5 ed.; pp. 1224-1227; (Pluronics F-127); (year of pub. sufficiently earlier than effective US filing date and any foreign priority date) 2002.

Fiedler Encyclopedia of Excipients for Pharmaceuticals, Cosmetics and Related Areas; Ed. E.M. Hoepfner; vol. 2 (L-Z); 5 ed.; p. 1596; (Tetronic); (year of pub. sufficiently earlier than effective US filing date and any foreign priority date) 2002.

The Merck Index, An Encyclopedia of chemicals, drugs, and biologicals; Ed. Susan Budavari; 12th Edition; "7519 Phosphorycholine"; p. 1267; (year of pub. sufficiently earlier than effective US filing date and any foreign priority date) 1996.

Szczotka-Flynn; Introducing the latest silicone hydrogel lens; Contact Lens Spectrum; 20(8); 2 pages; retrieved from the internet (https://www.clspectrum.com/issues/2005/august-2005/contact-lens-materials); Aug. 1, 2005.

Vladkova; Surface engineered polymeric biomaterials with improved biocontact properties; International Journal of Polymer Science; Article ID 296094 doi:10.1155/2010/296094; 22 pages; (year of pub. sufficiently earlier than effective US filing and any foreign priority date) 2010.

PISSIS; Hydration studies in polymer hydrogels; Journal of Polymer Science Part B: Polymer Physics; 51(3); pp. 159-175; Feb. 2013.

* cited by examiner

FIG. 1A
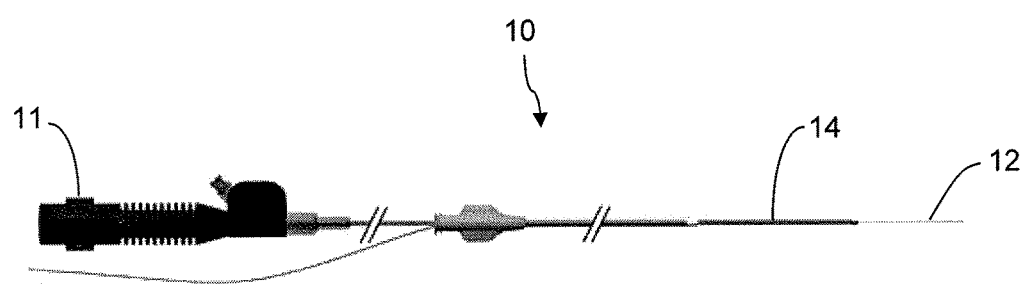
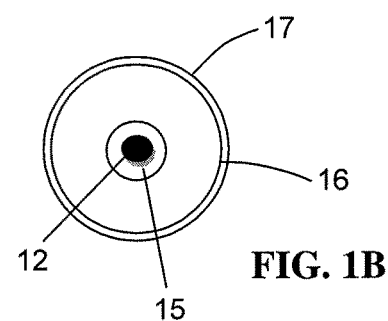
FIG. 1B

MEDICAL DEVICE COATING WITH A BIOCOMPATIBLE LAYER

CROSS-REFERENCE TO RELATED APPLICATIONS

This application claims priority to U.S. Provisional Patent Application 62/089,734 filed on Dec. 9, 2014 entitled "Medical Device Coating with a Biocompatible Layer", the disclosure of which is herein incorporated by reference in its entirety.

This application is also related to PCT/US2013/056703 filed on Aug. 27, 2013 titled "Contact Lens with a Hydrophilic Layer" and published as WO 2014/035912 and to PCT/US2014/065588 filed on Nov. 14, 2014 titled "Contact Lens with a Hydrophilic Layer" and published as WO 2015/073758, each of which are incorporated by reference in their entirety.

INCORPORATION BY REFERENCE

All publications and patent applications mentioned in this specification are herein incorporated by reference to the same extent as if each individual publication or patent application was specifically and individually indicated to be incorporated by reference.

FIELD

Embodiments of the technology relate to medical devices with improved biocompatibility and surface properties and methods for making the improved devices. More particularly, the technology relates to medical devices with a highly stable hydrogel layer covering the surface.

BACKGROUND

The use of such biomaterial articles as substitute blood vessels, synthetic and intraocular lenses, electrodes, catheters, orthopedic implants and the like in and onto the body is a rapidly developing area of medicine. A primary impediment to the use of such biomaterial devices has been the lack of satisfactory biocompatibility of the device surfaces. The uncoated surfaces of catheters made from plastics, for example, often stimulate rapid thrombogenic action. Various plasma proteins play a role in initiating platelet and fibrin deposition on plastic surfaces and these actions, and the inflammatory reaction that follows, can lead to the loss of function of the device. A "medical device" may be defined as a material that is substantially insoluble in body fluids and that is designed and constructed to be placed in or onto the body or to contact fluid of the body. Catheters, grafts, stents, implants, wound dressings, cardiac valves and intravenous tubing are examples of medical devices.

A medical device surface can desirably have the following characteristics: The device surface will not generally induce undesirable reactions in the body such as blood clotting, tissue death, tumor formation, allergic reaction, foreign body reaction (rejection) or inflammatory reaction. The device surface can be fabricated and sterilized easily such as by autoclave heat sterilization. The device surface does not substantially alter the function of the underlying device during the time that it remains implanted in or in contact with the body, whether it be an hour or a lifetime. The surface or surface coating is nontoxic to the tissues it is in contact with. In the case of a device with an optical function, the surface will be optically clear to allow proper function.

As used herein, the solid surface of a biomaterial is characterized as "biocompatible" if it is capable of functioning or existing in contact with biological fluid and/or tissue of a living organism with a net beneficial effect on the living organism. Long-term biocompatibility is desired for the purpose of reducing disturbance of the host organism.

A number of approaches have been suggested to improve the biocompatibility of implantable items. One approach has been to modify the surface of a biomaterial to prevent undesirable protein adhesion by providing the biomaterial with a protein resistant surface. For example, a contact lens may bind proteins on the lens to create protein deposits in the eye area. Additionally, the lens can cause structural changes including protein denaturation that can elicit an immune response such as tearing, reddening, or swelling in the ocular region. Accordingly, contemplated embodiments provide for medical devices and methods of making devices with improved resistance to undesirable protein interactions and other interactions at the surface.

SUMMARY OF THE DISCLOSURE

In general, in one embodiment, a medical device including an outer surface and a hydrogel layer covalently attached to at least a portion of the outer surface, the hydrogel layer adapted to contact a body tissue or fluid, wherein the hydrogel layer comprises a biocompatible polymer population having a first hydrophilic polymer species including polyethylene glycol (PEG) and a second hydrophilic polymer species including polyacrylamide, the first hydrophilic polymer species being at least partially covalently cross-linked to the second hydrophilic polymer species, wherein the medical device may not be a contact lens.

This and other embodiments can include one or more of the following features. The device can be configured to be implantable within a mammalian body. The device can be a stent configured to keep a cavity open. The stent can be configured to keep a blood vessel, bile duct, intestine, nasal passage or cavity, sinus cavity, or intraocular channel open. The device can be a sensor, camera, vital sign monitor, drug depot device, neurostimulator, ultrasound, silicone implant, saline implant, hernia mesh, penile implant, orthopedic rod or plate or pin or nails, pacemaker, cardiac valve, ear tube, aneurysm coil, or intraocular lens. The device can be a test strip. The device can be a drug, salivary, urine, blood or semen test strip. The device can be a tool configured to be inserted within a mammalian body. The device can be a catheter, trocar, endoscope, or laparoscope. The device can be configured to be used externally on a mammalian body. The device can be configured for use as a bandage, wound dressing, external sensor, hearing aid, or artificial skin. The outer surface of the device can include one or more of: glass, plastic, titanium, nitinol, polyethylene, polypropylene, polyvinyl chloride, polytetraflouroethylene, polydimethylsiloxane, polyethylene terephthalate, polyamides, polyether urethane, polyether urethane urea, polystyrene, polycarbonate, polysulfones, polymethyl methacrylate, poly 2-hydroxyethylmethacrylate, polyvinylalcohol, polyglycolic acid, polycaprolactone, polylactic acid, polyortho ester, cellulose acetate, collagen, or silk. The outer surface of the device can consists essentially of a material selected from the group consisting of: glass, plastic, titanium, nitinol, polyethylene, polypropylene, polyvinyl chloride, polytetraflouroethylene, polydimethylsiloxane, polyethylene terephthalate, polyamides, polyether urethane, polyether urethane urea, polystyrene, polycarbonate, polysulfones, polymethyl methacrylate, poly 2-hydroxyethylmethacrylate, polyvinylalcohol, polyglycolic acid, polycaprolactone, polylactic acid, polyortho ester, cellulose acetate, collagen, or silk. The first species can include a reactive electrophilic group or a reactive nucleophilic group and the second species can include a reactive electrophilic group or a reactive nucleophilic group complementary to the first species, the reactive electrophilic group and the reactive nucleophilic group can be adapted to react to thereby form cross-links between the first species to the second species. The reactive electrophilic group can be selected from the group consisting of: amino-reactive groups, sulfhydryl-reactive groups, carboxyl groups, hydroxyl groups, haloalkyl groups, dienophile groups, aldehyde or ketone groups, alkenes, epoxides, and phosphoramidites. The reactive nucleophilic group can be selected from the group consisting of: amines, amino-reactive groups, sulfhydryl, sulfhydryl-reactive groups, carboxyl groups, hydroxyl groups, haloalkyl groups, dienophile groups, aldehyde or ketone groups, alkenes, epoxides, and phosphoramidites. At least one of the reactive electrophilic group of the first species or the reactive electrophilic group of the second species can be covalently linked to the outer surface of the device. The hydrogel layer substantially can surround the outer surface of the device. The hydrogel layer or the hydrogel layer and device can be substantially optically clear. The hydrogel layer can be adapted to allow optical transmission through the hydrogel layer to the device. The hydrogel layer can be adapted to attenuate x-ray transmission. The hydrogel layer can be adapted to enable diffusion of biologic molecules, glucose, solutes, polymers, drugs. The hydrogel layer can include a thickness between about 5 nm to about 30 nm. The hydrogel layer can include a thickness below about 100 nm. The hydrogel layer can include a thickness less than about 50 nm. The hydrogel layer can include a thickness less than about 1 micron. The hydrogel layer can include a maximum thickness of about 10 microns. A first portion of the hydrogel layer can include a first thickness different from a second thickness of a second portion of the hydrogel layer. Each of the first and second hydrophilic polymer species can be a branched species having a branch count between two to twelve branch arms. The first hydrophilic polymer species can include a reactive electron pair accepting group and the second hydrophilic polymer species can include a reactive nucleophilic group, the reactive electron pair accepting group and the reactive nucleophilic group can be adapted to react to thereby form cross-links between the first hydrophilic polymer species to the second hydrophilic polymer species. The hydrogel layer has a lower coefficient of friction than an underlying device surface. The hydrogel can have a relative protein resistance compared to an underlying device surface. The hydrogel layer can include between about 80% to about 98% water by weight.

In general, in one embodiment, a medical device including an outer surface covered by an outer biocompatible polymer layer, wherein the biocompatible polymer layer includes a first polyethylene glycol (PEG) macromer subpopulation having an electron pair accepting moiety and a second macromer subpopulation including polyacrylamide having a first nucleophilic reactive moiety, wherein the first and second macromer subpopulations are cross-linked.

This and other embodiments can include one or more of the following features. The device can be configured to be implantable within a mammalian body. The device can be a stent configured to keep a cavity open. The stent can be configured to keep a blood vessel, bile duct, intestine, nasal passage or cavity, sinus cavity, or intraocular channel open. The device can be a glucose sensor, endoscopic camera, vital sign monitor, drug depot device, neurostimulator, ultrasound, breast implant, hernia mesh, penile implant, orthopedic rod or plate or pin or nails, pacemaker, cardiac valve, ear tube, aneurysm coil, or intraocular lens. The device can be a tool configured to be inserted within a mammalian body. The device can be a catheter, trocar, endoscope, or laparoscope. The device can be configured to be used externally on a mammalian body. The device can be configured for use as a bandage, wound dressing, external sensor, hearing aid, or artificial skin. The medical device may not be a contact lens. The outer surface of the device can include or consist essentially of any of the following: glass, plastic, titanium, nitinol, polyethylene, polypropylene, polyvinyl chloride, polytetraflouroethylene, polydimethylsiloxane, polyethylene terephthalate, polyamides, polyether urethane, polyether urethane urea, polystyrene, polycarbonate, polysulfones, polymethyl methacrylate, poly 2-hydroxyethylmethacrylate, polyvinylalcohol, polyglycolic acid, polycaprolactone, polylactic acid, polyortho ester, cellulose acetate, collagen, or silk. The outer surface of the device can consist essentially of a material selected from the group consisting of: glass, plastic, titanium, nitinol, polyethylene, polypropylene, polyvinyl chloride, polytetraflouroethylene, polydimethylsiloxane, polyethylene terephthalate, polyamides, polyether urethane, polyether urethane urea, polystyrene, polycarbonate, polysulfones, polymethyl methacrylate, poly 2-hydroxyethylmethacrylate, polyvinylalcohol, polyglycolic acid, polycaprolactone, polylactic acid, polyortho ester, cellulose acetate, collagen, or silk. The biocompatible polymer layer can be attached to the device by a covalent linkage between the electron pair accepting moiety of the first hydrophilic polymer macromer and a second nucleophilic reactive moiety on a surface of the device. The first species can include a reactive electrophilic group or a reactive nucleophilic group and the second species can include a reactive electrophilic group or a reactive nucleophilic group complementary to the first species, the reactive electrophilic group and the reactive nucleophilic group can be adapted to react to thereby form cross-links between the first species to the second species. The reactive electrophilic group can be selected from the group consisting of: amino-reactive groups, sulfhydryl-reactive groups, carboxyl groups, hydroxyl groups, haloalkyl groups, dienophile groups, aldehyde or ketone groups, alkenes, epoxides, and phosphoramidites. The reactive nucleophilic group can be selected from the group consisting of: amines, amino-reactive groups, sulfhydryl, sulfhydryl-reactive groups, carboxyl groups, hydroxyl groups, haloalkyl groups, dienophile groups, aldehyde or ketone groups, alkenes, epoxides, and phosphoramidites. At least one of the reactive electrophilic group of the first species or the reactive electrophilic group of the second species can be covalently linked to the outer surface of the device. The biocompatible polymer layer can include between about 50% and about 98% water by weight. The biocompatible polymer layer can include between about 85% and about 98% water by weight. The hydrogel layer can include a thickness between about 5 nm to about 30 nm. The hydrogel layer can include a thickness below about 100 nm. The hydrogel layer can include a thickness less than about 50 nm. The hydrogel layer can include a thickness less than about 1 micron. The hydrogel layer can include a maximum thickness of about 10 microns. The biocompatible polymer layer can further include at least one active agent. The at least one active agent can be selected from the group consisting of a protein, drug, nanoparticle, cell, or solute.

In general, in one embodiment, a method of making a medical device with a hydrophilic polymer layer including reacting an outer surface of the medical device with a first polymer species of a hydrophilic polymer solution, wherein the first polymer species comprises a moiety at a first portion that forms a covalent attachment to the outer surface of the device and reacting the first polymer species of the hydrophilic polymer solution with a second polymer species of the hydrophilic polymer solution, the second polymer species including a moiety that forms a covalent bond to a second portion of the first polymer species in a second covalent reaction thereby forming a hydrogel coating including the first polymer species and the second polymer species at least partially cross-linked.

This and other embodiments can include one or more of the following features. The device can be configured to be implantable within a mammalian body. The device can be a stent configured to keep a cavity open. The stent can be configured to keep a blood vessel, bile duct, intestine, nasal passage or cavity, sinus cavity, or intraocular channel open. The hydrophilic polymer layer can reduce thrombosis of the stent. The device can be a glucose sensor, endoscopic camera, vital sign monitor, drug depot device, neurostimulator, ultrasound, breast implant, hernia mesh, penile implant, orthopedic rod or plate or pin or nails, pacemaker, cardiac valve, ear tube, aneurysm coil, or intraocular lens. The hydrophilic polymer layer can reduce an immune system reaction against the implant. The device can be a tool configured to be inserted within a mammalian body. The device can be a catheter, trocar, endoscope, or laparoscope. The hydrophilic polymer layer can increase blood flow through the catheter when the catheter can be inserted into a mammalian body. The device can be configured to be used externally on a mammalian body. The device can be configured for use as a bandage, wound dressing, external sensor, hearing aid, or artificial skin. The medical device may not be a contact lens. The outer surface of the device can include or consist essentially of any of the following: glass, plastic, titanium, nitinol, stainless steel, polyethylene, polypropylene, polyvinyl chloride, polytetraflouroethylene, polydimethylsiloxane, polyethylene terephthalate, polyamides, polyether urethane, polyether urethane urea, polystyrene, polycarbonate, polysulfones, polymethyl methacrylate, poly 2-hydroxyethylmethacrylate, polyvinylalcohol, polyglycolic acid, polycaprolactone, polylactic acid, polyortho ester, cellulose acetate, collagen, or silk. The outer surface of the device can consist essentially of a material selected from the group consisting of: glass, plastic, titanium, nitinol, stainless steel, polyethylene, polypropylene, polyvinyl chloride, polytetraflouroethylene, polydimethylsiloxane, polyethylene terephthalate, polyamides, polyether urethane, polyether urethane urea, polystyrene, polycarbonate, polysulfones, polymethyl methacrylate, poly 2-hydroxyethylmethacrylate, polyvinylalcohol, polyglycolic acid, polycaprolactone, polylactic acid, polyortho ester, cellulose acetate, collagen, or silk. The reacting steps can be performed at a temperature between about 15 degrees Celsius and about 100 degrees Celsius. The reacting steps can be performed at a temperature between about 20 degrees Celsius and about 40 degrees Celsius. The reacting steps can be performed at a pH between about 7 and about 11. The hydrophilic polymer layer can be substantially optically clear. The covalent attachment between the outer surface of the device and the first portion of the first polymer species can be formed by a first nucleophilic conjugate reaction. The second covalent reaction can be a second nucleophilic conjugate reaction. The partial cross-linking can be between an electrophilic moiety of the first species and a nucleophilic moiety of the second species in a nucleophilic conjugate reaction. The hydrophilic polymer layer can include a first species selected from the group consisting of: polyethylene glycol (PEG), phosphorylcholine, poly(vinyl alcohol), poly (vinylpyrrolidinone), poly(N-isopropylacrylamide) (PNIPAM), polyacrylamide (PAM), poly(2-oxazoline), polyethylenimine (PEI), poly(acrylic acid), polymethacrylate, polyelectrolytes, hyaluronic acid, chitosan, chondroitin sulfate, alginate, hydroxypropylmethylcellulose, and dextran. The hydrophilic polymer layer can include a second species selected from the group consisting of: polyethylene glycol (PEG), phosphorylcholine, poly(vinyl alcohol), poly(vinylpyrrolidinone), poly(N-isopropylacrylamide) (PNIPAM), polyacrylamide (PAM), poly(2-oxazoline), polyethylenimine (PEI), poly(acrylic acid), polymethacrylate, polyelectrolytes, hyaluronic acid, chitosan, chondroitin sulfate, alginate, hydroxypropylmethylcellulose, and dextran. The hydrophilic polymer layer can include a first species including polyethylene glycol (PEG). The hydrophilic polymer layer can include a second species including polyacrylamide. The first species can include a reactive electrophilic group or a reactive nucleophilic group and the second species can include a reactive electrophilic group or a reactive nucleophilic group complementary to the first species, the reactive electrophilic group and the reactive nucleophilic group can be adapted to react to thereby form cross-links between the first species to the second species. The reactive electrophilic group can be selected from the group consisting of: amino-reactive groups, sulfhydryl-reactive groups, carboxyl groups, hydroxyl groups, haloalkyl groups, dienophile groups, aldehyde or ketone groups, alkenes, epoxides, and phosphoramidites. The reactive nucleophilic group can be selected from the group consisting of: amines, amino-reactive groups, sulfhydryl, sulfhydryl-reactive groups, carboxyl groups, hydroxyl groups, haloalkyl groups, dienophile groups, aldehyde or ketone groups, alkenes, epoxides, and phosphoramidites. At least one of the reactive electrophilic group of the first species or the reactive electrophilic group of the second species can be covalently linked to the outer surface of the device. The method can further include modifying the outer surface of the device to form the plurality of reactive nucleophilic sites or a plurality of electrophilic sites on the outer surface. The modifying step can include exposing the outer surface of the medical device to a gas plasma treatment. The method can further include adding a bifunctional monomer or a polymer to a prepolymerization mixture used to form the hydrophilic polymer layer. The bifunctional monomer or polymer may not substantially change the optical properties of the contact medical device. The bifunctional monomer or polymer can provide additional nucleophilic or electrophilic reactive sites on the surface of the device. The method can further include modifying an outer surface of the device. Modifying the outer surface of the device can include one or more of: pH adjustment, plasma activation, light activation, activation of the liquid monomer mix, wet activation, and adding a monomer that reacts with the outer surface of the device that still leaves reactive sites. Both of the first and second nucleophilic conjugate reactions can be Click reactions. The Click reaction can be a conjugate addition reaction. Both of the first and second nucleophilic conjugate addition reactions can be 1,4-nucleophilic addition reactions. The first and second nucleophilic conjugate addition reactions can be both Michael-type reactions. The reacting steps can be performed at a pH between about 5 and about 11. The method can further include adding at least one active agent to the hydrophilic polymer layer. The at least one active agent can be selected from the group consisting of a UV-absorbing agent, a visibility tinting agent, an antimicrobial agent, a bioactive agent, a leachable lubricant, a leachable tear-stabilizing agent, or any mixture thereof. The antimicrobial agent can include silver nanoparticles. The hydrophilic polymer layer can have a thickness of less than about 50 nm.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 1 shows a catheter in accordance with an embodiment. FIG. 1B is a cross section view of the catheter illustrated in FIG. 1A.

DETAILED DESCRIPTION

Figure 2A:
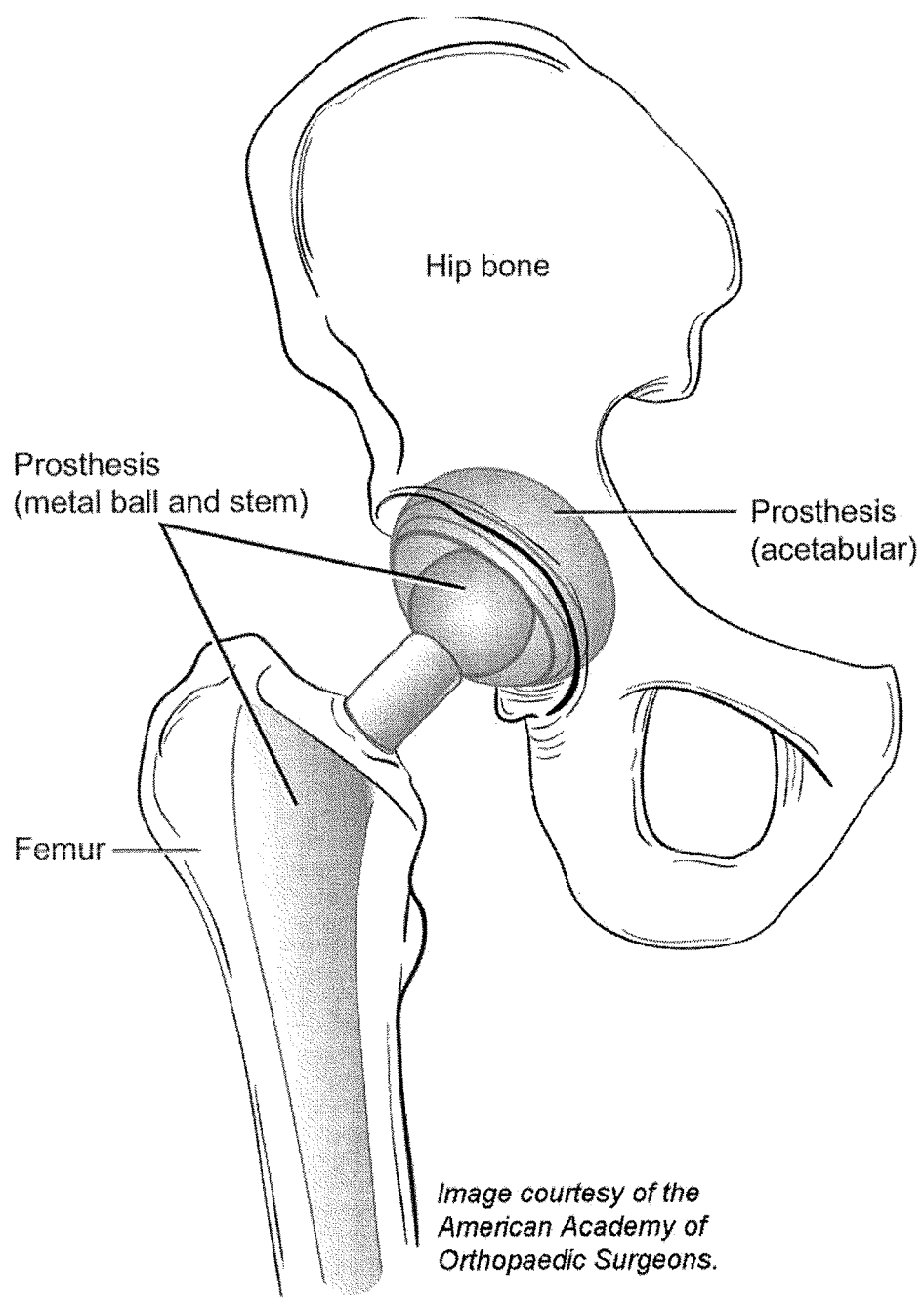
FIG. 2A shows prosthetic implants for replacing a hip joint.

Methods for forming biocompatible coatings are disclosed herein. The biocompatible coatings can be formed on a surface of a medical device. The biocompatible coating can improve the compatibility of the medical device with the biological tissue that the device contacts. The processes disclosed herein advantageously allow for rapid, high yield reactions to coat the medical devices. The reactions do not produce toxic byproducts, which is a large advantage when medical devices are coated. The reaction can also take place in an aqueous solution thereby facilitating coating coverage of the device surfaces. In some embodiments the medical device is not a contact lens.

The properties of the biocompatible coating can be tailored based on the specific medical device application. For example, the coating can have improved protein resistance and antithrombogenic properties on vascular stents and on catheters or other devices used in the vasculature. For example, the catheter coating can result in increased blood flow through the catheter. The biocompatible coating can also improve wettability, lubricity, protein resistance, and antithrombogenicity of catheter devices.

The medical device can be used in on or on mammalian bodies. In some embodiments the medical device is used within the mammalian body. In some embodiments the medical device is implanted in the mammalian body. In some embodiments the medical device contacts an external surface of the mammalian body.

FIG. 1A illustrates a catheter 10 in accordance with an embodiment. The catheter 10 has a handle 11 and flexible outer shaft 14. The catheter 10 has a lumen configured to receive a guidewire 12. FIG. 1B illustrates a cross section of the catheter 10 showing a cross section of the guidewire 12 within a guidewire lumen 15. A biocompatible coating 17 is formed on an outer surface 16 of the catheter 10.

FIG. 2A shows prosthetic implants for replacing a hip joint. The prosthesis includes a metal ball and stem engaged with the femur and an acetabular prosthesis engaged with the hip bone. The biocompatible coating can be formed on the exterior surfaces of the acetabular prosthesis and the metal ball and stem prosthesis. The biocompatible coating can improve the lubricity of the prosthesis surfaces and decrease friction between the metal ball and acetabular prosthesis.

Figure 2B:
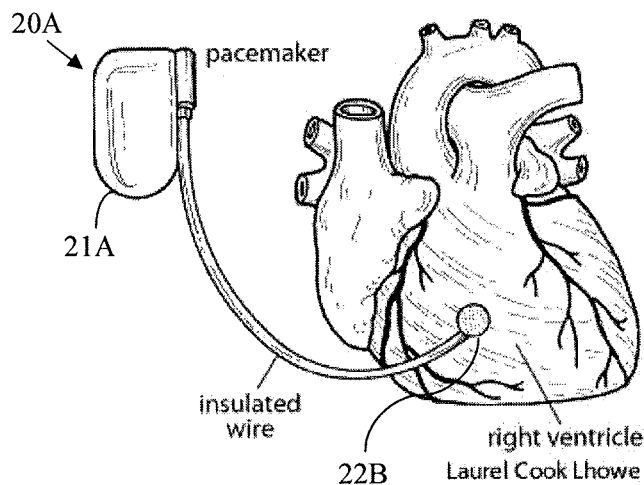
FIG. 2B shows an implantable pacemaker.

FIG. 2B shows an implantable pacemaker 20A. The implantable pacemaker 20A includes an electronics compartment 21A, insulated wire, and electrode 22B. The electronics compartment 21A, insulated wire, and electrode 22B of the implantable pacemaker 20A can be partially or fully coated with the biocompatible coatings described herein.

Figure 2C:
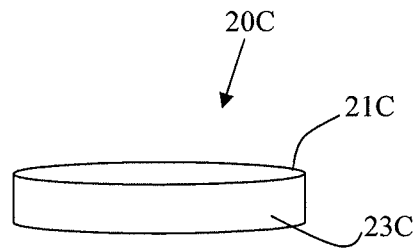
FIG. 2C shows an implantable glucose sensor.

FIG. 2C shows an implantable glucose sensor 20C. The glucose sensor 20C can have an outer surface 21C with biocompatible coating 23C.

Figure 2D:
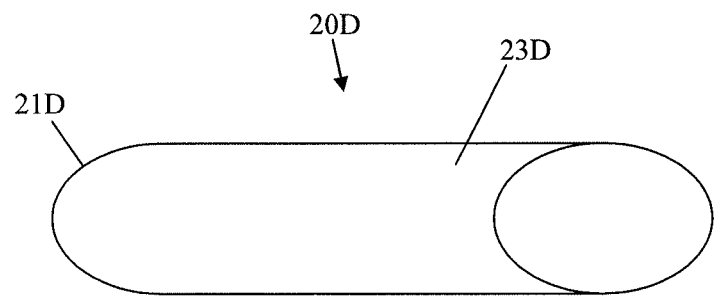
FIG. 2D shows a stent.

FIG. 2D shows a stent 20D. The stent 20D has an outer surface 21D with a biocompatible coating 23D. The stent 20D is illustrated in a tubular configuration. Other stent shapes and configurations are possible. The stents can be used in vascular applications, gastrointestinal applications, and in other hollow body lumens.

A. Biocompatible Polymer Layer

As used herein, the term "biocompatible layer" or "hydrogel layer" may refer to a single continuous layer or various coated portions on the medical device.

Although shown in FIG. 1B as a single biocompatible layer covering an exterior of the medical device, it is to be appreciated that in some cases, only a portion of the medical device (e.g. a single surface or a part of a surface) may be coated by a biocompatible polymer layer. In some cases, the biocompatible layer may only coat one of the medical device surfaces such as the surface in direct contact with the tissue. Moreover, the layer may not coat the entire area of the surface.

Additionally, other contemplated embodiments may include two or more noncontiguous biocompatible polymer layers. For example, a first biocompatible polymer layer may at least partially cover one surface while a second biocompatible polymer layer may at least partially cover a second surface. The first and second biocompatible polymer layer may not touch or share a boundary with one another.

In certain embodiments, the arrangement between the medical device and the surrounding hydrogel or biocompatible layer may be understood as a layered structure with a biocompatible polymer layer attached to an outer surface of a medical device. The biocompatible polymer layer may be placed on either of the anterior or posterior surfaces. In some variations, the biocompatible layer may only cover a portion of the medical device.

In other cases, the arrangement may include a first biocompatible polymer layer on one side of the medical device, a second biocompatible polymer layer on another side of the medical device. The core layer being a middle layer between the two biocompatible polymer layers. The first and second layers may share a boundary (e.g. contiguous layers) or may form separate independent layers (e.g. noncontiguous layers).

In some cases, the layered arrangement on a medical device can be established by fluorescence analysis methods as described in Qui et al, U.S. Pat. Appl. Nos. 201200026457 and 201200026458 or alternatively, by scanning electron microscopy.

Additionally, the biocompatible layer may have relatively uniform dimensions, compositions, and mechanical properties throughout. The biocompatible layer may have a substantially uniform thickness, water content, and chemical composition throughout the layer. In some embodiments, the biocompatible layer has a substantially homogeneous composition and a substantially uniform depth and/or thickness. In some embodiments the hydrogel layer substantially surrounds the outer surface of the medical device. In other embodiments the hydrogel layer can be applied to only a portion of the medical device or only the portion of the medical device that contacts the body tissue or fluid.

As can be appreciated, uniformity is not required and may not be desirable for all situations. In some cases, a single layer may include portions having different characteristics including dimensions, composition, and/or mechanical properties. For example, a portion of the layer may have a different thickness than another portion, which may result in varying water content between the two portions.

In some cases the medical device can include multiple hydrogel layer coatings applied to different portions of the device. The different coatings can have different properties. The different properties can be tailored the specific portion of the device to which the coating is applied. In some examples a first portion of the hydrogel layer can have a first thickness and a second portion of the hydrogel layer can have a second thickness with the first thickness and second thickness being different.

Similarly, where two or more biocompatible layers are used, the biocompatible polymer layers may share or differ in any characteristics. For example, the medical device may be asymmetrically layered with the biocompatible polymer. The depth/thickness of the resulting biocompatible polymer layers may vary between the layers on opposing sides of the medical device. This can result in, for example, different mechanical characteristics between the anterior facing side of the coated medical device and the posterior side.

In some variations, the average thickness of the biocompatible polymer layer may range between about 25 nm and about 50 nm. In particular embodiments, the biocompatible layer has a thickness of about 1 nm to about 500 nm. In an exemplary embodiment, the thickness of the biocompatible layer is between about 1 nm and about 10 microns, or between about 1 nm and about 50 nm, or between about 10 nm and about 200 nm, or between about 25 nm and about 200 nm, or between about 25 nm and about 100 nm, or between about 5 nm and about 50 nm, or between about 10 nm and about 50 nm, or between about 10 nm and about 35 nm, or between about 10 nm and about 25 nm, or between about 1 nm and about 10 nm. In some embodiments, the hydrogel layer comprises a thickness below about 100 nm.

In some embodiments, the hydrogel layer comprises a thickness below about 50 nm. In some embodiments, the hydrogel layer comprises a thickness below about 40 nm. In some embodiments, the hydrogel layer has a thickness between about 5 nm to about 30 nm. In some embodiments, the hydrogel layer has a thickness less than about 1 micron. In some embodiments, the hydrogel layer has a thickness less than about 10 microns.

In further variations, the thickness or depth of the hydrogel layer may also be expressed in terms of the fold-multiple over a layer that could be represented as a molecular monolayer. In some embodiments, the biocompatible layer has a thickness of that exceeds the nominal thickness of a molecular monolayer by at least five-fold. For example, in some cases the biocompatible polymer layer is formed from PEG molecules that have a PEG monolayer radius of about 5 nm. The PEG containing biocompatible polymer layer may have a thickness of about 50 nm, which results in a layer thickness or depth that is approximately 10-fold greater than the PEG monolayer radius.

Without limitation, the thickness of the anterior or posterior surface of a coated medical device of the invention can be determined by Scanning Electron Microscopy, AFM or fluorescence microscopy analysis of a cross section of the medical device in fully hydrated state as described herein.

Additionally, the biocompatible layer may be understood to have a volume. In some cases, a first portion of the layer may have first volume V1 and a second portion of the layer may have a second volume V2. The volume may be calculated based on an estimated surface area of the layer. A total volume may also be understood to be the volume of a single biocompatible layer (e.g. a layer covering an entire implant) or a sum of various layers with corresponding volumes.

Volume calculations may be based on an estimated surface area of approximately 1.25 square centimeters, in the example of a contact lens on each side of the lens core. In some cases, the biocompatible polymer layer has a volume in the range of about 15 nl to about 1.5 µl. In other variations, a volume range of about 7.5 nl to about 150 nl corresponds to an enveloping biocompatible thickness range of about 25 nm to about 500 nm. Other volume ranges are possible for coatings on medical devices having different geometries. For example, the layer on a coated catheter forms an annular shape. The coating volume can be calculated using the dimensions of the annular shape.

For water content of the biocompatible layer, in some embodiments, the water content is between about 50% and about 98% water by weight. In some embodiments, the water content is between about 80% and about 98% water by weight. In some embodiments, the water content is between about 85% and about 98% water by weight. In other embodiments, the biocompatible layer includes between about 85% and about 95% water by weight. Additionally, the water content of the biocompatible layer may be expressed either by total water content or by a weight/volume percent. The polymer content of the biocompatible layer may be described also by a weight/volume percent.

The biocompatible layer may also include a biocompatible polymer population having one or more subpopulations or species. In some cases, one or more species or subpopulations are cross-linked to form the biocompatible polymer layer. The biocompatible polymer layer precursors may be provided in a solution containing the cross-linkable material. Once cross-linked, the one or more species form the biocompatible polymer coating.

In one variation, the biocompatible layer includes a first polymer species and a second polymer species that are at least partially cross-linked together to form the biocompatible layer. Additionally, the polymer species or subpopulation may include linear and/or branched components. A branched species may include a polymer having a branch count ranging from 2-arm to 12-arm branching. In other embodiments, the branched species may include starred branching with about 100 branches or more.

Figure 3A:
FIGS. 3A-3B show a first polymer species and a second polymer species with respective reactive groups A and N.
Figure 3B:
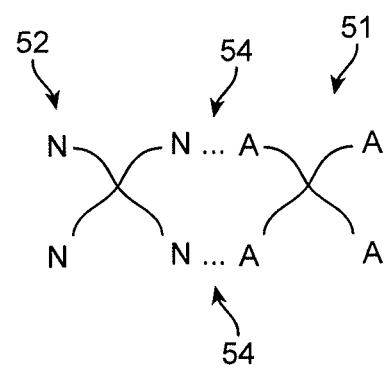

Referring to the FIG. 3A, a first branched polymer species 51 and a second branched polymer species 52 are schematically shown. The first branched polymer species 51 has four branch arms with reactive functional group A. The second branched polymer species 52 is shown having four branch arms with a reactive functional group N. In some embodiments, a reactive moiety A of the first polymer species 51 is adapted to react with a reactive moiety B of the second polymer species 52. The reaction between moieties A and B may form a covalent cross-link between the first and second polymer species. FIG. 3B depicts the first and second species 51, 52 cross-linked by an A-N moiety formed by a reaction between the reactive group A of the first polymer species and a reactive group B of a second polymer species. In some embodiments, the cross-linking action between one or more polymer and/or macromer species forms the biocompatible polymer layer. For example, cross-linking one or more polymer species in a polymer solution may form a hydrogel with desirable characteristics for coating the medical device.

As can be appreciated, the cross-linking mechanism and/or reaction for a first and second polymer species may include any number of suitable methods known in the art including photochemical or thermal cross-linking. In some cases, cross-linking may occur through nucleophilic conjugate reaction, Michael-type reaction (e.g. 1,4 addition), and/or Click reaction between respective reactive groups on more than one polymer species in the biocompatible layer.

Any suitable polymers may be used for the biocompatible polymer population in the biocompatible layer. In some cases, the polymer population includes species derived from polyethylene glycol (PEG), phosphorylcholine, poly(vinyl alcohol), poly(vinylpyrrolidinone), poly(N-isopropylacrylamide) (PNIPAM), polyacrylamide (PAM), poly(2-oxazoline), polyethylenimine (PEI), poly(acrylic acid), acrylic polymers such as polymethacrylate, polyelectrolytes, hyaluronic acid, chitosan, and dextran. In some embodiments a PEG polymer species or macromer is used in the biocompatible coating. In some embodiments a PAM polymer species or macromer is used in the biocompatible coating. In some embodiments a PEG polymer species or macromer and a PAM species or macromer are used in the biocompatible coating.

Additionally, any suitable reactive moieties may be used for the polymer species and subpopulations including reactive functional groups (e.g. reactive nucleophilic groups and electron pair acceptor) that react to form covalent linkages between polymer species or subpopulations to form the biocompatible polymer layer described.

1. Reactive Functional Groups

Reactive functional groups and classes of reactions useful in covalent linking and cross-linking are generally known in the art. In some cases, suitable classes of reactions with reactive functional groups include those that proceed under relatively mild conditions. These include, but are not limited to nucleophilic substitutions (e.g., reactions of amines and alcohols with acyl halides and activated esters), electrophilic substitutions (e.g., enamine reactions) and additions to carbon-carbon and carbon-heteroatom multiple bonds (e.g., Michael reactions and Diels-Alder reactions). These and other useful reactions are discussed, for example, in: March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

a) Amines and Amino-Reactive Groups

In one embodiment, the reactive functional group is a member selected from amines, such as a primary or secondary amine, hydrazines, hydrazides, and sulfonylhydrazides. Amines can, for example, be acylated, alkylated or oxidized. Useful non-limiting examples of amino-reactive groups include N-hydroxysuccinimide (NHS) esters, sulfo-NHS esters, imidoesters, isocyanates, isothiocyanates, acylhalides, arylazides, p-nitrophenyl esters, aldehydes, sulfonyl chlorides and carboxyl groups.

NHS esters and sulfo-NHS esters react preferentially with the primary (including aromatic) amino groups of the reaction partner. The imidazole groups of histidines are known to compete with primary amines for reaction, but the reaction products are unstable and readily hydrolyzed. The reaction involves the nucleophilic attack of an amine on the acid carboxyl of an NHS ester to form an amide, releasing the N-hydroxysuccinimide.

Imidoesters are the most specific acylating reagents for reaction with the amine groups of e.g., a protein. At a pH between 7 and 10, imidoesters react only with primary amines. Primary amines attack imidates nucleophilically to produce an intermediate that breaks down to amidine at high pH or to a new imidate at low pH. The new imidate can react with another primary amine, thus crosslinking two amino groups, a case of a putatively monofunctional imidate reacting bifunctionally. The principal product of reaction with primary amines is an amidine that is a stronger base than the original amine. The positive charge of the original amino group is therefore retained. As a result, imidoesters do not affect the overall charge of the conjugate.

Isocyanates (and isothiocyanates) react with the primary amines of the conjugate components to form stable bonds. Their reactions with sulfhydryl, imidazole, and tyrosyl groups give relatively unstable products.

Acylazides are also used as amino-specific reagents in which nucleophilic amines of the reaction partner attack acidic carboxyl groups under slightly alkaline conditions, e.g. pH 8.5.

Arylhalides such as 1,5-difluoro-2,4-dinitrobenzene react preferentially with the amino groups and phenolic groups of the conjugate components, but also with its sulfhydryl and imidazole groups.

p-Nitrophenyl esters of carboxylic acids are also useful amino-reactive groups. Although the reagent specificity is not very high, α- and ε-amino groups appear to react most rapidly.

Aldehydes react with primary amines of the conjugate components. Although unstable, Schiff bases are formed upon reaction of the amino groups with the aldehyde. Schiff bases, however, are stable, when conjugated to another double bond. The resonant interaction of both double bonds prevents hydrolysis of the Schiff linkage. Furthermore, amines at high local concentrations can attack the ethylenic double bond to form a stable Michael addition product. Alternatively, a stable bond may be formed by reductive amination.

Aromatic sulfonyl chlorides react with a variety of sites of the conjugate components, but reaction with the amino groups is the most important, resulting in a stable sulfonamide linkage.

Free carboxyl groups react with carbodiimides, soluble in both water and organic solvents, forming pseudoureas that can then couple to available amines yielding an amide linkage. Yamada et al., *Biochemistry* 1981, 20: 4836-4842, e.g., teach how to modify a protein with carbodiimides.

b) Sulfhydryl and Sulfhydryl-Reactive Groups

In another embodiment, the reactive functional group is a member selected from a sulfhydryl group (which can be converted to disulfides) and sulfhydryl-reactive groups. Useful non-limiting examples of sulfhydryl-reactive groups include maleimides, alkyl halides, acyl halides (including bromoacetamide or chloroacetamide), pyridyl disulfides, and thiophthalimides.

Maleimides react preferentially with the sulfhydryl group of the conjugate components to form stable thioether bonds. They also react at a much slower rate with primary amino groups and imidazole groups. However, at pH 7 the maleimide group can be considered a sulfhydryl-specific group, since at this pH the reaction rate of simple thiols is 1000-fold greater than that of the corresponding amine.

Alkyl halides react with sulfhydryl groups, sulfides, imidazoles, and amino groups. At neutral to slightly alkaline pH, however, alkyl halides react primarily with sulfhydryl groups to form stable thioether bonds. At higher pH, reaction with amino groups is favored.

Pyridyl disulfides react with free sulfhydryl groups via disulfide exchange to give mixed disulfides. As a result, pyridyl disulfides are relatively specific sulfhydryl-reactive groups.

Thiophthalimides react with free sulfhydryl groups to also form disulfides.

c) Other Reactive Functional Groups

Other exemplary reactive functional groups include:
(a) carboxyl groups and various derivatives thereof including, but not limited to, N-hydroxybenztriazole esters, acid halides, acyl imidazoles, thioesters, p-nitrophenyl esters, alkyl, alkenyl, alkynyl and aromatic esters;
(b) hydroxyl groups, which can be converted to esters, ethers, aldehydes, etc.;
(c) haloalkyl groups, wherein the halide can be displaced with a nucleophilic group such as, for example, an amine, a carboxylate anion, thiol anion, carbanion, or an alkoxide ion, thereby resulting in the covalent attachment of a new group at the site of the halogen atom;
(d) dienophile groups, which are capable of participating in Diels-Alder reactions such as, for example, maleimido groups;
(e) aldehyde or ketone groups, such that subsequent derivatization is possible via formation of carbonyl derivatives such as, for example, imines, hydrazones, semicarbazones or oximes, or via such mechanisms as Grignard addition or alkyllithium addition;
(f) alkenes, which can undergo, for example, cycloadditions, acylation, Michael addition, etc;
(g) epoxides, which can react with, for example, amines and hydroxyl groups;
(h) phosphoramidites and other standard functional groups useful in nucleic acid synthesis and
(i) any other functional group useful to form a covalent bond between the functionalized ligand and a molecular entity or a surface.

d) Reactive Functional Groups with Non-specific Reactivities

In addition to the use of site-specific reactive moieties, the present invention contemplates the use of non-specific reactive functional groups. Non-specific groups include photoactivatable groups, for example. Photoactivatable groups are ideally inert in the dark and are converted to reactive species in the presence of light. In one embodiment, photoactivatable groups are selected from macromers of nitrenes generated upon heating or photolysis of azides. Electron-deficient nitrenes are extremely reactive and can react with a variety of chemical bonds including N—H, O—H, C—H, and C=C. Although three types of azides (aryl, alkyl, and acyl derivatives) may be employed, arylazides are presently preferred. The reactivity of arylazides upon photolysis is better with N—H and O—H than C—H bonds. Electron-deficient arylnitrenes rapidly ring-expand to form dehydroazepines, which tend to react with nucleophiles, rather than form C—H insertion products. The reactivity of arylazides can be increased by the presence of electron-withdrawing substituents such as nitro or hydroxyl groups in the ring. Such substituents push the absorption maximum of arylazides to longer wavelength. Unsubstituted arylazides have an absorption maximum in the range of 260-280 nm, while hydroxy and nitroarylazides absorb significant light beyond 305 nm. Therefore, hydroxy and nitroarylazides may be preferable since they allow to employ less harmful photolysis conditions for the affinity component than unsubstituted arylazides.

In an exemplary embodiment, photoactivatable groups are selected from fluorinated arylazides. The photolysis products of fluorinated arylazides are arylnitrenes, all of which undergo the characteristic reactions of this group, including C—H bond insertion, with high efficiency (Keana et al., *J. Org. Chem.* 55: 3640-3647, 1990).

In another embodiment, photoactivatable groups are selected from benzophenone residues. Benzophenone reagents generally give higher crosslinking yields than arylazide reagents.

In another embodiment, photoactivatable groups are selected from diazo compounds, which form an electron-deficient carbene upon photolysis. These carbenes undergo a variety of reactions including insertion into C—H bonds, addition to double bonds (including aromatic systems), hydrogen attraction and coordination to nucleophilic centers to give carbon ions.

In still another embodiment, photoactivatable groups are selected from diazopyruvates. For example, the p-nitrophenyl ester of p-nitrophenyl diazopyruvate reacts with aliphatic amines to give diazopyruvic acid amides that undergo ultraviolet photolysis to form aldehydes. The photolyzed diazopyruvate-modified affinity component will react like formaldehyde or glutaraldehyde.

It is well within the abilities of a person skilled in the art to select a reactive functional group, according to the reaction partner. As an example, an activated ester, such as an NHS ester can be a useful partner with a primary amine. Sulfhydryl reactive groups, such as maleimides can be a useful partner with SH, thiol, groups.

Additional exemplary combinations of reactive functional groups found on a compound of the invention and on a targeting moiety (or polymer or linker) are set forth in Table 1.

TABLE 1

| Chemical Functionality 1 | Chemical Functionality 2 | Linkage |
| --- | --- | --- |
| Hydroxy | Carboxy | Ester |
| | Hydroxy | Carbonate |
| | Amine | Carbamate |
| | $SO_3$ | Sulfate |
| | $PO_3$ | Phosphate |
| | Carboxy | Acyloxyalkyl |
| | Ketone | Ketal |
| | Aldehyde | Acetal |
| | Hydroxy | Anhydride |
| Mercapto | Mercapto | Disulfide |
| | Carboxy | Acyloxyalkyl Thioether |
| | Carboxy | Thioester |
| | Carboxy | Amino amide |
| | Mercapto | Thioester |
| | Carboxy | Acyloxyalkyl ester |
| | Carboxy | Acyloxyalkyl amide |
| | Amino | Acyloxyalkoxy carbonyl |
| | Carboxy | Anhydride |
| | Carboxy | N-acylamide |
| | Hydroxy | Ester |
| | Hydroxy | Hydroxymethyl ketone ester |
| | Hydroxy | Alkoxycarbonyl oxyalkyl |
| Amino | Carboxy | Acyloxyalkylamine |
| | Carboxy | Acyloxyalkylamide |
| | Amino | Urea |
| | Carboxy | Amide |
| | Carboxy | Acyloxyalkoxycarbonyl |
| | Amide | N-Mannich base |
| | Carboxy | Acyloxyalkyl carbamate |
| Phosphate oxygen ester | Hydroxy | Phosphate |
| | Amine | Phosphoramidate |
| | Mercapto | Thiophosphate ester |
| Ketone | Carboxy | Enol ester |
| Sulfonamide | Carboxy | Acyloxyalkyl sulfonamide |
| | Ester | N-sulfonyl-imidate |

One skilled in the art will readily appreciate that many of these linkages may be produced in a variety of ways and using a variety of conditions. For the preparation of esters, see, e.g., March supra at 1157; for thioesters, see, March, supra at 362-363, 491, 720-722, 829, 941, and 1172; for carbonates, see, March, supra at 346-347; for carbamates, see, March, supra at 1156-57; for amides, see, March supra at 1152; for ureas and thioureas, see, March supra at 1174; for acetals and ketals, see, Greene et al. supra 178-210 and March supra at 1146; for acyloxyalkyl derivatives, see, PRODRUGS: TOPICAL AND OCULAR DRUG DELIVERY, K. B. Sloan, ed., Marcel Dekker, Inc., New York, 1992; for enol esters, see, March supra at 1160; for N-sulfonylimidates, see, Bundgaard et al., *J. Med. Chem.*, 31:2066 (1988); for anhydrides, see, March supra at 355-56, 636-37, 990-91, and 1154; for N-acylamides, see, March supra at 379; for N-Mannich bases, see, March supra at 800-02, and 828; for hydroxymethyl ketone esters, see, Petracek et al. *Annals NY Acad. Sci.*, 507:353-54 (1987); for disulfides, see, March supra at 1160; and for phosphonate esters and phosphonamidates.

The reactive functional groups can be chosen such that they do not participate in, or interfere with, the reactions necessary to assemble the reactive ligand analogue. Alternatively, a reactive functional group can be protected from participating in the reaction by the presence of a protecting group. Those of skill in the art will understand how to protect a particular functional group from interfering with a chosen set of reaction conditions. For examples of useful protecting groups, see Greene et al., PROTECTIVE GROUPS IN ORGANIC SYNTHESIS, John Wiley & Sons, New York, 1991.

Generally, prior to forming the linkage between the compound of the invention and the targeting (or other) agent, and optionally, the linker group, at least one of the chemical functionalities will be activated. One skilled in the art will appreciate that a variety of chemical functionalities, including hydroxy, amino, and carboxy groups, can be activated using a variety of standard methods and conditions. For example, a hydroxyl group of the ligand (or targeting agent) can be activated through treatment with phosgene to form the corresponding chloroformate, or p-nitrophenylchloroformate to form the corresponding carbonate.

In an exemplary embodiment, the invention makes use of a targeting agent that includes a carboxyl functionality. Carboxyl groups may be activated by, for example, conversion to the corresponding acyl halide or active ester. This reaction may be performed under a variety of conditions as illustrated in March, supra pp. 388-89. In an exemplary embodiment, the acyl halide is prepared through the reaction of the carboxyl-containing group with oxalyl chloride. The activated agent is combined with a ligand or ligand-linker arm combination to form a conjugate of the invention. Those of skill in the art will appreciate that the use of carboxyl-containing targeting agents is merely illustrative, and that agents having many other functional groups can be conjugated to the ligands of the invention.

Figure 4A:
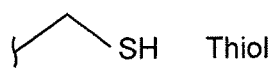
FIGS. 4A-4B show a reaction between a sulfonyl and thiol group.
Figure 4A:
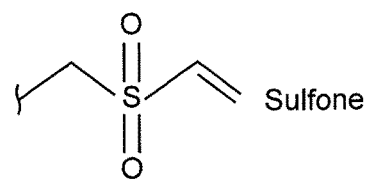
Figure 4B:
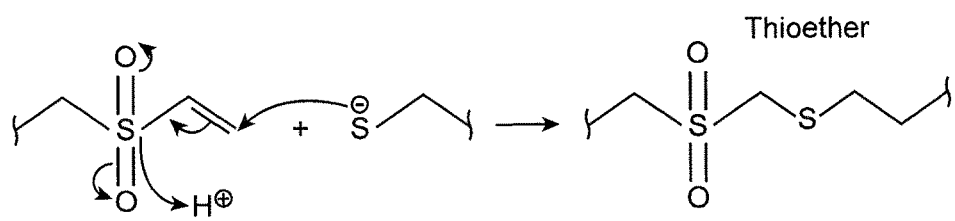

Referring to FIG. 4A, in some embodiments, the reactive functional groups include thiol and sulfonyl moieties. The reactive nucleophilic group may be a thiol group adapted to react to a sulfonyl group that functions as an electron pair accepting moiety. Where a first polymer species contains a reactive thiol group and a second polymer species contains a reactive sulfonyl group, the cross-linkage between the first and second species may be formed through a thioether moiety (FIG. 4B).

In other variations, one or more polymer species in the biocompatible layer are covalently linked through a sulfonyl moiety such as, but not limited to, an alkylene sulfonyl moiety, a dialkylene sulfonyl moiety, an ethylene sulfonyl moiety, or a diethylene sulfonyl moiety. In further variations, one or more polymer species in the biocompatible layer are covalently linked through a sulfonyl moiety and a thioether moiety, or an alkylene sulfonyl moiety and a thioether moiety, or a dialkylene sulfonyl moiety and a thioether moiety, or an ethylene sulfonyl moiety and a thioether moiety, or a diethylene sulfonyl moiety and a thioether moiety.

In further variations, the one or more polymer species in the biocompatible layer are covalently linked through an ester moiety, or alkylene ester moiety, or an ethylene ester moiety, or a thioether moiety, or an ester moiety and a thioether moiety, or an alkylene ester moiety and a thioether moiety, or an ethylene ester moiety and a thioether moiety.

In some embodiments, the ratio of the reactive subpopulations in the biocompatible polymer population is approximately 1 to 1. In other embodiments, the concentration of one of the subpopulations or species exceeds another species by about 10% to about 30%. For example, the concentration of a polymer species with an electron pair accepting moiety may exceed another polymer species with a reactive nucleophilic group.

Additionally, where the concentration of a first and second polymer species are approximately 1 to 1, the relative number of reactive moieties for each species may be approximately the same or different. For example, a polymer species may have more sites having an electron pair accepting moiety compared to the number of reactive sites on the other polymer species carrying the nucleophilic group. This may be accomplished, for example, by having a first branched polymer species having more arms with reactive electron pair accepting sites compared to a second polymer species carrying the nucleophilic moiety.

2. PEG-containing Biocompatible Layer

In some embodiments, the polymers in the biocompatible layer comprise polyethylene glycol (PEG). The PEG may include species that have a molecular weight of between about 1 kDa and about 40 kDa. In particular embodiments, the PEG species have a molecular weight of between about 5 kDa and about 30 kDa. In some embodiments, the biocompatible polymer population consists of a species of polyethylene glycol (PEG). In other variations, the weight average molecular weight $M_w$ of the PEG polymer having at least one amino or carboxyl or thiol or vinyl sulfone or acrylate moiety (as a biocompatibleity-enhancing agent) can be from about 500 to about 1,000,000, or from about 1,000 to about 500,000. In other embodiments, the biocompatible polymer population comprises different species of PEG.

In some cases, the polymer includes subunits of PEG. In some variations, the subunits of the polymers of the PEG-containing layer of the medical device are or at least about 50%, or at least about 75%, at least about 90%, or at least about 96%, or at least about 97%, or at least about 98%, or at least about 99% or at least about 99.5% water.

In some cases, the water content of the PEG-containing biocompatible layer is between about 59% and about 98% water by weight. In other embodiments, the biocompatible layer includes between about 50% and about 75% water by weight. In other embodiments, the biocompatible layer includes between about 75% and about 95% water by weight. In other embodiments, the biocompatible layer includes between about 85% and about 95% water by weight.

The PEG-containing biocompatible layer may include a PEG hydrogel having a swelling ratio. To determine swelling ratio, the PEG-hydrogel can be weighed immediately following polymerization and then immersed in distilled water for a period of time. The swollen PEG hydrogel is weighed again to determine the amount of water absorbed into the polymer network to determine the swelling ratio. The mass fold increase an also be determined based on this comparison before and after water swelling. In some embodiments, the PEG-containing layer has a mass fold increase of less than about 10%, or of less than about 8%, or of less than about 6%, or of less than about 5%, or of less than about 4%, or of less than about 3%, or of less than about 2%, or of less than about 1%. In some cases, the mass fold increase is measured by weighing the hydrogel when wet and then dehydrating it and weighing it again. The mass fold increase is then the swollen weight minus the dry weight divided by the swollen weight. For the biocompatible layer as opposed to a bulk hydrogel, this could be accomplished by coating a non-hydrated substrate and then performing mass change calculations.

In another aspect, the invention provides for a biocompatible layer with two cross-linkable PEG species. The first PEG species may include a reactive functional group adapted to react to another reactive functional on the second species comprising PEG or PAM. Any of the described functional groups (e.g. previous section (A)(1)) may be suitable for forming a cross-linkage between the first and second polymer species.

In some cases, the first PEG species includes an electron pair accepting moiety and the second polymer species may include a reactive nucleophilic moiety. Once cross-linked through a reaction between the electron pair accepting and nucleophilic moieties, the PEG polymer network forms a hydrogel with a water content or concentration. The PEG hydrogel may serve as the biocompatible coating a medical device to provide improved wettability, lubricity, protein resistance, or antithrombogenicity.

3. Active Agents

The biocompatible polymer layer may include one or more active agents. Examples of active agents include one or more of a medicinal agent, UV-absorbing agent, a visibility tinting agent, an antimicrobial agent, an antithrombotic agent, a bioactive agent, a leachable lubricant, a leachable tear-stabilizing agent, or any mixture thereof. Additional examples of active agents includes a bioactive agent or drug, nanoparticle, cell, solute, or protein. The substances and materials may be deposited on the medical device to augment the interaction of a device with the body. These substances may consist of polymers, drugs, or any other suitable substance and may be used to treat a variety of pathologies including but not limited dry eye disease, glaucoma, macular degeneration, cardiovascular disease, thrombosis, renal failure, infection, wounds, cancer, or allergies.

Other examples of active agents include antimicrobial agents. One example of an antimicrobial agent is silver nanoparticles.

4. Interpenetration Polymer Network

The outer hydrogel network may also consist of interpenetrating polymer networks (or semi-interpenetrating polymer networks) formed in either simultaneous or sequential polymerization steps. For example, upon forming the initial outer hydrogel layer, the layer can be swollen in a monomer solution such as acrylic acid along with a crosslinker and initiator. Upon exposure to UV light, a second interpenetrating network will form. The double network confers additional mechanical strength and durability while maintaining high water content and high biocompatibility.

B. Medical Devices

Many devices would benefit from a biocompatible coating including any device that is placed inside of or in contact with the body or any of its tissues or fluids. The devices can be placed inside of the body temporarily during a medical procedure or can be implanted inside the body for short term or long term use.

In some embodiments, the device is a catheter, defined as an artificial tube designed to carry fluid or serve as a conduit for instrumentation. This includes but is not limited to, catheters placed in arteries or veins for infusing or removing fluids such as saline or blood as for dialysis. Other embodiments include catheters placed in the peritoneal cavity, urinary bladder, or skull. For example, an outer surface of a catheter could be coated and/or an inner surface of the catheter tube could be coated.

Additional embodiments include trocars and endoscopes placed in the peritoneal cavity, urinary bladder, or skull. In some embodiments the medical devices include a laparoscope or laparoscopic tools. Further embodiments include tubing for instilling fluid and blood for tubing for cardiac bypass.

In some embodiments, the device is an implantable device placed in the skin, subcutaneous tissue, abdomen, spine, chest, brain or other bodily cavity, to detect, transmit, or record data, deliver a bioactive substance such as a drug, or deliver an electrical stimulus. The device can be placed inside of the body for short term use or for longer term use. This includes but is not limited to, glucose sensors, endoscopic cameras, vital sign monitors, drug depot devices, neurostimulators, ultrasounds, breast implants, silicone implants, saline implants, hernia meshes, penile implants, orthopedic rods, plates, pins or nails, pacemakers, cardiac valves, ear tubes, aneurysm coils, or intraocular lenses.

In some embodiments, the device is a stent designed to keep a cavity open, including blood vessels, bile ducts, intestines, nasal passage or cavity, sinus cavity, or intraocular channels.

The hydrogel layer can be designed to increase biocompatibility of the medical device. In one example, the hydrophilic layer could reduce thrombosis associated with a stent. In another example, the hydrophilic layer could be designed to increase blood flow through a catheter or other device. In yet another example, the hydrophilic layer could reduce a mammalian immune system response against the implanted device.

In some embodiments, the medical device is configured to be used externally on a mammalian body. Examples include a bandage, wound dressing, external sensor, hearing aid, or artificial skin.

In some embodiments the medical device can be a test strip. Examples of test strips include drug, salivary, urine, blood, and semen test strips.

In some embodiments the medical device is not a contact lens.

In some embodiments the properties of the hydrogel layer can be selected to meet desired optical characteristics. For example, the hydrogel layer can be substantially optically clear or the hydrogel layer and device can be substantially optically clear. In some embodiments the hydrogel layer is adapted to allow optical transmission through the hydrogel layer to the device.

In some embodiments the properties of the hydrogel layer can be selected or modified to attenuate x-ray transmissions.

In some embodiments the hydrogel layer is adapted to enable diffusion of biologic molecules, glucose, solutes, polymers, or drugs.

In some embodiments the hydrogel layer has a lower coefficient of friction than the underlying device surface.

In some embodiments the hydrogel layer has a relative protein resistance compared to the underlying device surface.

C. Attachment of Biocompatible Layer to Device

Another aspect of the invention provides for a coated medical device with biocompatible polymer layer that is covalently linked and attached to the device. The covalent linkage between the biocompatible layer and the outer surface of the medical device may be understood to be a linking moiety that is covalently disposed between the outer surface of the medical device and the biocompatible layer. In some cases, the linking moiety covalently attaches the biocompatible layer to an outer surface of the device.

The coatings disclosed herein can be applied to a variety of different materials. Examples of the outer surface materials list include: glass, plastic, titanium, stainless steel, nitinol, polyethylene, polypropylene, polyvinyl chloride, polytetraflouroethylene, polydimethylsiloxane, polyethylene terephthalate, polyamides, polyether urethane, polyether urethane urea, polystyrene, polycarbonate, polysulfones, polymethyl methacrylate, poly 2-hydroxyethylmethacrylate, polyvinylalcohol, polyglycolic acid, polycaprolactone, polylactic acid, polyortho ester, cellulose acetate, collagen, or silk. The outer surface of the device can comprise a portion with one or more of these materials. In some embodiments the outer surface of the medical device can consist essentially of one or more of these materials.

In some embodiments, the linking moiety may include any of the reactive functional groups described in at least section (A)(1). In further variations, the linking moiety may be a resultant moiety formed from a reaction between one or more of the reactive functional groups described in at least section (A)(1). For example, the linking moiety may include an electron pair accepting group such as a Michael-type Michael-Type electron pair accepter (e.g. sulfone group) on a polymer species in the biocompatible layer that reacts to covalently attach the biocompatible polymer layer to the device.

Figure 5A:
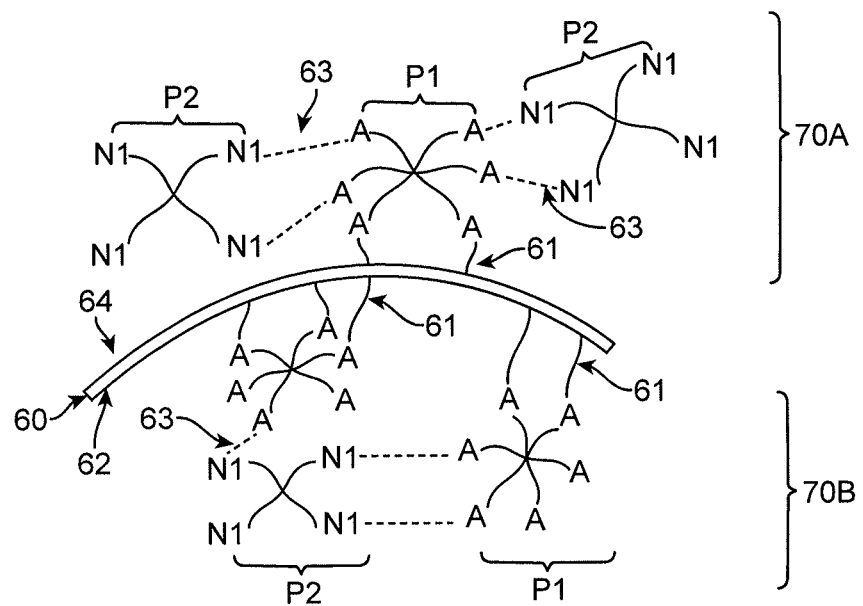
FIGS. 5A-5C show schematically a biocompatible polymer having two species covalently attached to a lens core.
Figure 5B:
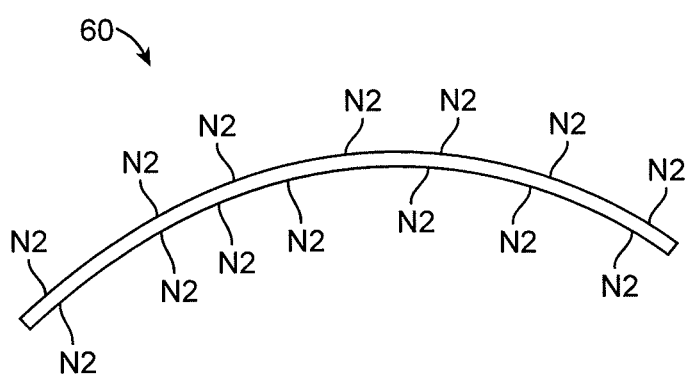
Figure 5C:
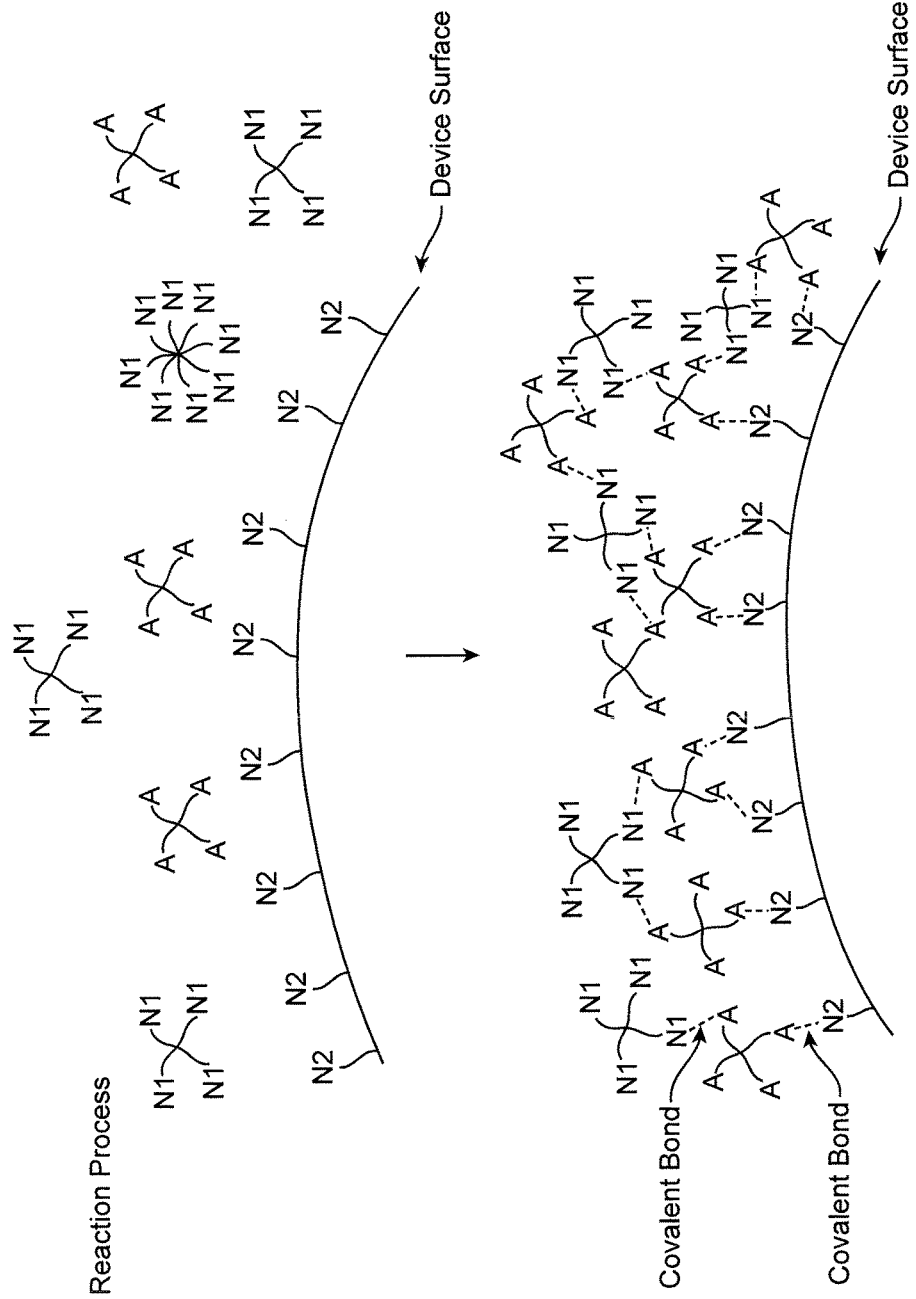

Advantageously, the biocompatible polymer layer may be attached to the device through similar reactions utilized to cross-link the biocompatible polymer layer. Referring to FIGS. 5A-5C, the biocompatible polymer layer includes a first polymer species P1 having a reactive group A and second polymer species P2 with a reactive group N1. As described earlier, the biocompatible polymer layer may be formed by cross-linking the first polymer species and the second polymer species through a reaction between reactive group A and N1. FIG. 5A illustrates forming a biocompatible layer 70A/70B on an anterior surface 64 and a posterior surface 62 of a medical device 60. As shown in FIG. 5A cross-linkages 63 covalently link the first and second species to form the first biocompatible polymer layer 70A on the anterior surface 64 and the second biocompatible polymer layer 70B on the posterior surface 62 of the device 60.

Referring still to FIG. 5A, the first polymer species also forms a covalent linkage 61 with the outer surface of the device. As shown, the covalent linkage is formed through the reactive group A of the first polymer species P1 and the device surface. In some embodiments, the reactive group A on the first polymer species P1 reacts to (1) crosslink the polymer species in the biocompatible polymer layer and (2) attach the formed biocompatible polymer layer to the device. In such cases, this permits a first portion of the A moieties to react with the N1 moieties and a second portion of A moieties to react with the device surface. In some cases, the concentration of the first polymer species P1 and/or the number of available reactive A moieties of the first polymer species exceeds the corresponding concentration of the second polymer species and/or available reactive N1 moieties.

Referring to FIG. 5B, the device may include a reactive moiety N2. Reactive moiety N2 may be adapted to react with reactive groups of polymer species in the biocompatible polymer layer. In some cases, the reactive moiety N2 only reacts to one of the polymer species. Referring to FIG. 5C, reactive moiety N2 reacts with reactive group A on the first species P1 to form a covalent attachment between the biocompatible polymer layer and the device.

As can be appreciated, the reaction for attaching the biocompatible polymer layer to the device may include any number of suitable methods known in the art including those described in at least section (A)(1). In some cases, covalent linking occurs through nucleophilic conjugate reaction, Michael-type reaction (e.g. 1,4 addition), and/or Click reaction between respective reactive groups on more than one polymer species in the biocompatible layer.

In some cases, the reactive A group is an electron pair acceptor and the reactive groups N1 and N2 are reactive nucleophilic groups. N1 and N2 may be the same or different reactive groups. Continuing with the example shown in FIGS. 5A-5C, the biocompatible polymer layer is formed by a first reaction between the reactive A group and reactive nucleophile N1. Additionally, the biocompatible polymer layer is covalently attached to the core through a second reaction between the reactive A group and nucleophile N2. The two reactions may occur simultaneously or near simultaneously in the same reaction vessel.

Where the reactive functional groups include thiol and sulfonyl moieties, the reactive A group may be a sulfonyl group on a first PEG macromer. The sulfone moiety functions as an electron pair accepting moiety on the first PEG macromer. The reactive nucleophiles N1 and/or N2 may be a thiol group (see FIG. 4A). For the first reaction, the first and second macromers form a cross-link through the reactive thiol and sulfonyl groups, which can results in a thioether moiety (see FIG. 4B). Where the N2 nucleophile on the device is also thiol, a thioether may also be formed by a reaction between the sulfonyl moiety on the first PEG macromer and the N2 on the surface of the device.

As can be appreciated, the nucleophilic group (or other type of reactive group) on the device does not need to be the same as the reactive groups in the biocompatible polymer layers. However, utilizing the same reactive groups may provide some advantages such as controllability and predictability of the respective reactions.

In other variations, the biocompatible polymer layer are covalently linked to the device surface through a sulfonyl moiety such as, but not limited to, an alkylene sulfonyl moiety, a dialkylene sulfonyl moiety, an ethylene sulfonyl moiety, or a diethylene sulfonyl moiety. In further variations, the biocompatible polymer layer is covalently attached to the device through a sulfonyl moiety and a thioether moiety, or an alkylene sulfonyl moiety and a thioether moiety, or a dialkylene sulfonyl moiety and a thioether moiety, or an ethylene sulfonyl moiety and a thioether moiety, or a diethylene sulfonyl moiety and a thioether moiety.

In further variations, the biocompatible polymer layer is covalently attached to the device through an ester moiety, or alkylene ester moiety, or an ethylene ester moiety, or a thioether moiety, or an ester moiety and a thioether moiety, or an alkylene ester moiety and a thioether moiety, or an ethylene ester moiety and a thioether moiety.

In further embodiments, the linkage between the device and the biocompatible layer is covalent, to the particular exclusion of any other form of chemical bond or association. For example, a hydrogel layer as described may be bound to the surface of a device by a chemical bond that consists of a covalent bond.

E. Contact Angle

Advantageously, some of the contemplated coated devices provide for a biocompatible polymer layer that has a population of hydrophilic polymers that are cross-linked with each other and, moreover, are as a whole, covalently attached to a device or layer. As such, the biocompatible polymer layer can improve the hydrophilicity of the device.

As described in further detail below, the hydrophilicity or wettability of the hydrogel layer may be measured by a contact angle goniometer that implements a method known as a captive bubble contact angle test. Relatively high hydrophilicity is associated with a relatively low advancing contact angle.

In typical embodiments of the device according to the disclosed technology, when the device is subjected to a bubble contact angle test, the medical device shows an advancing contact in the range about 20° to about 75°. In more particular embodiments, the medical device shows an advancing contact in the range about 35° to about 55°.

Figure 6A:
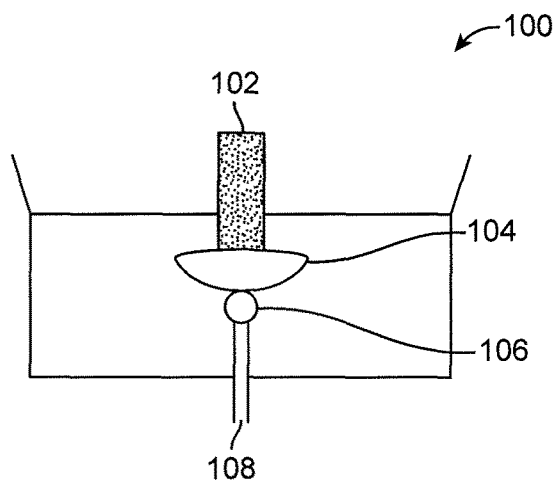
FIGS. 6A-6C show a captive bubble test.
Figure 6B:
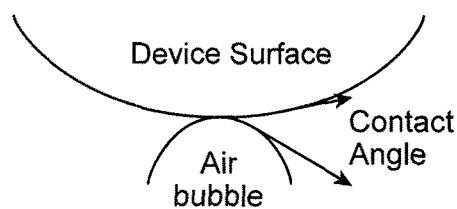
Figure 6C:
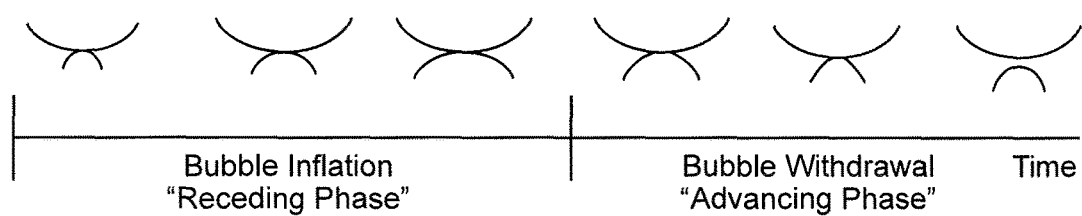

FIGS. 6A-6C show aspects of a captive bubble test that is commonly used in the device industry as a surrogate measure of wettability or hydrophilicity of surfaces, as provided by embodiments of the technology. FIG. 6A shows the setup 100 for a captive bubble test. The setup 100 includes a device holding fixture 102 in communication with a test device 104. An air bubble 106 is positioned at a surface of the test device from a syringe pump 108. The test device 104 is illustrated with a curved surface; however, devices having different geometries can also be tested.

FIG. 6B shows a schematic view of the contact angle as it occurs in an aqueous solution between the surface of a device and an air bubble, as the air bubble is being inflated against or being withdrawn away from the device.

FIG. 6C provides a schematic series of angles created as a bubble is being inflated against the device, and then withdrawn. The left side of the drawing depicts the "receding phase" of the test; the right side of the drawing depicts the "advancing phase of the test. On the left, after the bubble first makes contact at what will be the central contact point between the bubble and the device, the area of mutual contact expands, and the surrounding aqueous space recedes from the central contact point. Accordingly, this is termed the "receding phase". On the right, as the bubble is being withdrawn, the aqueous solution advances toward the central point of contact between the bubble and the device. Accordingly, this is termed the "advancing phase" of the test. These profiles can be videographed during the test to capture the dynamics. In the recorded videos, software-based edge detection and angular separation techniques can be used to measure the receding and advancing angles at the interface of the bubble and device.

In both the advancing and receding portions of the test, a small angle reflects the relatively high affinity of the device surface for water, rather than air. Thus, there is an association between a small contact angle and hydrophilicity or wettability of the device surface. In contrast, a large contact angle reflects a relative lack of affinity of the device surface with water. By means of this test, the hydrophilicity of device embodiments of the technology may be quantified.

In an exemplary embodiment, the device having a biocompatible polymer layer as described has an advancing contact angle of at least 20 degrees, or at least 25 degrees, or at least 30 degrees, or at least 35 degrees, or at least 40 degrees. In another embodiment, the advancing contact angle is between about 20 degrees and about 40 degrees, or between about 20 degrees and about 35 degrees, or between about 20 degrees and about 30 degrees, or between about 20 degrees and about 25 degrees, or between about 25 degrees and about 40 degrees, or between about 25 degrees and about 35 degrees, or between about 25 degrees and about 30 degrees, or between about 30 degrees and about 40 degrees or between about 35 and about 40 degrees. In another variation, the advancing contact angle is at least about 8 degrees, or at least about 9 degrees, or at least about 10 degrees, or at least about 11 degrees, or at least about 12 degrees, or at least about 13 degrees. In an exemplary embodiment, the advancing contact angle is between about 8 degrees and about 20 degrees, or between about 8 degrees and about 17 degrees, or between about 8 degrees and about 14 degrees, between about 8 degrees and about 12 degrees, or between about 9 degrees and about 20 degrees, or between about 9 degrees and about 17 degrees, or between about 9 degrees and about 14 degrees, between about 9 degrees and about 12 degrees, or between about 10 degrees and about 20 degrees, or between about 10 degrees and about 17 degrees, or between about 10 degrees and about 14 degrees, between about 10 degrees and about 12 degrees, or between about 11 degrees and about 20 degrees, or between about 11 degrees and about 17 degrees, or between about 11 degrees and about 14 degrees.

FIG. 15 shows contact angles measured for contemplated embodiments described. Lot numbers are shown for the measured embodiments made from described methods.

F. Methods of Making a Coated Device or Multi-Layered Device

Another aspect of the invention provides for methods of making described coated and/or layered devices.

In some embodiments, the method includes the steps of reacting a surface of a device with a biocompatible polymer solution. The biocompatible polymer solution may contain one or more subpopulations or species that are adapted to react to form a coating on at least a portion of the device. In some cases, the biocompatible polymer solution reacts to form a cross-linked coating on the device. The coating may be partially or substantially completely cross-linked.

As shown in FIG. 3A, the biocompatible polymer solution may include a first polymer species with a reactive group A and a second polymer species with a reactive group N. The biocompatible polymer layer may be formed on the medical device surface by reacting the reactive groups on the first and second polymer species to form the cross-linked biocompatible polymer layer. As shown in FIG. 3B, the reactive groups A and N may form a covalent linkage 54 between the first and second polymer species to thereby cross-link the two species and result in a biocompatible polymer layer. In some cases, the reaction between the first and second reactive groups on respective polymer species forms a hydrogel.

As described, any suitable reaction may be employed to form the biocompatible polymer layer. These include (without limitation) nucleophilic conjugate reactions, Michael-type reactions (e.g. 1,4 nucleophilic addition reactions), and/or click reactions. In some cases, the reactive groups A and N are an electron pair accepting moiety and a nucleophilic moiety respectively.

Additionally, in some variations, the polymer species or subpopulation with in the biocompatible polymer layer may include PEG species. In some cases, a first PEG species reacts with a second polymer species, such as a PEG or PAM species, to form the biocompatible polymer layer. For example, the first PEG species may include an electron pair acceptor adapted to react to a nucleophilic reactive moiety of a second PEG species or PAM species to covalently link the polymer species.

Some embodiments provide for a covalent attachment between the biocompatible polymer layer and the device. For example, one or more of the polymer subpopulation or species within the biocompatible polymer layer or solution may be adapted to react to the device to form a covalent attachment between the biocompatible layer and the device. In some cases, the method of biocompatible polymer layer attachment includes the step of reacting at least one of the polymer species with reactive sites on the surface of the device to form covalent bonds between the polymer species and the device surface.

In some embodiments modifying the outer surface of the device includes one or more of: pH adjustment, plasma activation, light activation, activation of the liquid monomer mix, wet activation, and adding a monomer that reacts with the outer surface of the device that still leaves reactive sites.

Referring again to FIGS. 5A-5C, a first polymer species P1 may include a reactive group A that is adapted to react to a reactive group N2 of the device 60 surface. The reaction between the A and N2 groups results in a covalent linkage 61 between the first polymer species P1 and the device 60.

As shown, the reactive group A may also be adapted to react with another reactive moiety N1 of a second polymer species P2 to form the biocompatible polymer layer. As such, a first reaction between P1 and P2 forms the biocompatible polymer layer and a second reaction couples the biocompatible polymer layer to the device.

In some cases, the same reactive group A on the first polymer species P1 is capable of reacting to either the reactive moiety N1 or N2. In one variation, a first portion of the reactive A groups react to the N1 moiety and a second portion of the reactive groups react to the N2 moiety. In some embodiments, the first and second portions of the reactive A groups are on the same molecule of a polymer species. In further variations, the first and second portions of the reactive A groups are on different branch arms of the same polymer species. The dual reactions between P1 and P2, and P1 and core may occur in the same reactive vessel and during the same reaction time (or overlapping in some portion of the reaction time).

As described, any suitable reaction may be employed to form the biocompatible polymer layer and attach the biocompatible polymer layer to the medical device. These include (without limitation) nucleophilic conjugate reactions, Michael-type reactions (e.g. 1,4 nucleophilic addition reactions), and/or click reactions. For example, the plurality of reactions may all be nucleophilic conjugate reactions. Alternatively, the plurality of reactions may be different types of reactions.

In some embodiments, the first and second reactions are nucleophilic conjugate reactions, more particularly, both are 1,4-nucleophilic addition Michael-type reactions. By way of example, in some embodiments, the nucleophilic reactive moiety of the first macromer population comprises a thiol group and the electron pair accepting moiety of the second macromer population comprises a sulfone group.

In other embodiments of the method the first and second nucleophilic conjugate reactions may be described more broadly as a "Click" type reaction. Click reactions, as originally described by Karl Sharpless and others, refer to modular assembly of macromolecules that are typified as occurring in an aqueous environment, delivering high yield as a result of being driven to completion by large thermodynamic force, and creating substantially no byproducts, or byproducts that are non-toxic to biological systems. The click reactions are advantageous for application toward the manufacture of devices because the devices may be reacted in an aqueous solution, without toxic byproducts, rapidly, and with a high yield.

Other examples of click type reactions that could be used to attach branched polymers in our immersive dip coating process including (a) general thiol-ene click reactions in general, (b) [3+2] cycloadditions, including the Huisgen 1,2-dipolar cycloaddition, (c) Diels-Alder reaction, (d) [4+1] cycloadditions between isonitriles (isocyanides) and tetrazines, (e) nucleophilic substitution especially to small strained rings like epoxy and aziridine compounds, (f) carbonyl-chemistry-like formation of ureas, and (g) addition reactions to carbon-carbon double bonds, such as involve dihydroxylation or the alkynes in the thiolyne reaction.

In a particular embodiment, the method of making the described coated device includes the steps of reacting an outer surface of the device with a first PEG species of a biocompatible polymer solution, wherein the first PEG species comprises an electron pair accepting moiety and a first portion of the electron pair accepting moiety forms a covalent attachment to the outer surface of the device through a first nucleophilic conjugate reaction; and reacting the first PEG species of the biocompatible polymer solution with a second polymer species of the biocompatible polymer solution, the second polymer species comprising a nucleophilic reactive moiety adapted to covalently link to a second portion of the electron pair accepting moiety of the first PEG species in a second nucleophilic conjugate reaction to thereby at least partially cross-link the first and second species, wherein a hydrogel coating is formed and covalently attached to the outer surface of the device by the first and second nucleophilic conjugate reactions.

In additionally embodiments, the method includes activating a surface of the device. Activating the surface may form a plurality of chemically reactive sites on the surface. The reactive sites may be, for example, nucleophilic sites for reaction with a biocompatible polymer.

Figure 7:
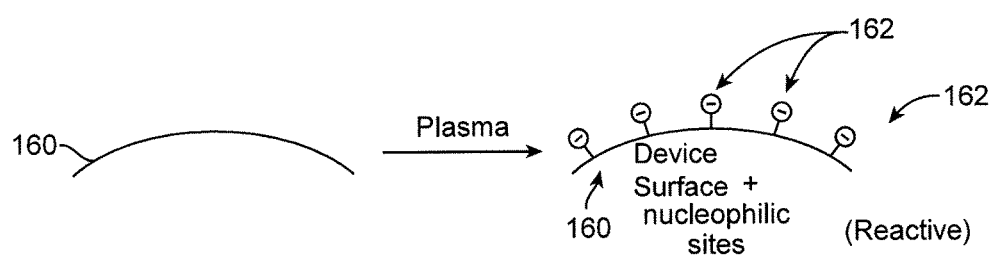
FIG. 7 shows an activated lens surface.

Referring to FIG. 7, a surface 160 of a medical device without reactive sites is shown with a plurality of reactive sites 162 following an activation or modification process. In some cases, a plasma process is used to activate the surface of a device. The activation process may include the step of exposing the outer surface of the device to gas plasma. In some embodiments, the device is transferred to a holding device, typically metal, and placed in a vacuum plasma chamber. The device is plasma treated in an atmospheric plasma to form reactive sites on the surface. In some cases, atmospheric plasma is applied to the device at 200 mTorr for about 3 minutes to thereby result in nucleophilic functional sites on the device. In some embodiments, the devices are dehydrated prior to the plasma treatment.

In further variations, the device surface may be activated through plasma treatment, preferably in oxygen or nitrogen gas. For example, the contemplated process may include activating a core material in a nitrogen plasma. In other variations, the surface may be activated through a plasma treatment in carbon dioxide, carbon monoxide, argon, nitrous oxide, hydrogen, or air.

In some embodiments modifying an outer surface of the device forms a plurality of reactive nucleophilic sites or a plurality of electrophilic sites on the outer surface.

In some embodiments modifying any other surface of the medical device can be done by adding a bifunctional monomer or a polymer to a prepolymerization mixture used to form a portion of the medical device. The bifunctional monomer or polymer does not substantially change the mechanical properties of the contact lens. The bifunctional monomer or polymer provides additional nucleophilic or electrophilic reactive sites on the surface of the medical device.

In some embodiments modifying the outer surface of the medical device includes adding a monomer that reacts with the medical device surface but still leaves reactive sites after the reaction.

In other embodiments, activation of the device surface can also occur through exposure to increasing pH's, for example solution pH of above 11.

In further embodiments, activation can also occur by modifying the monomer mix to include groups that are reactive to the branched biocompatible coating polymers. Activation of the monomer mix can be a direct activation, or activation with a protected group that is cleaved, for example by light or changing pH. In other cases, plasma polymerization of functional silanes including mercapto and amino silanes may be used for activation. Additionally, plasma polymerization of allyl alcohol and allyl amine can also be used for activation.

In some embodiments, the device activation or modification step results in a reactive group N2 (shown in FIG. 5B) that is capable of reacting with at least one of the polymer species of the biocompatible polymer layer. In some cases, at least one of the polymer species in the biocompatible polymer layer reacts with a portion of the plurality of reactive sites on the device outer surface to form a covalent attachment between the biocompatible polymer layer and the device surface. In some cases, the device is activated prior to the formation of the biocompatible polymer layer on the device surface.

In some embodiments, the process of making the coated device includes the step of reacting the activated device surface with a population of functionalized biocompatible polymers. For example, the biocompatible polymers may include a population of functionalized branched biocompatible macromers with a first subpopulation functionalized with a nucleophilic reactive moiety and a second subpopulation functionalized with an electron pair accepting moiety. In further embodiments, the method may include reacting the functional moieties of two macromer subpopulations with each other in a first nucleophilic conjugate reaction to form covalent linkages between the two macromer subpopulations, thereby forming a cross-linked polymer network.

The method may also include reacting the electron pair accepting moieties of second macromer subpopulation and the nucleophilic moieties of the activated device surface in a second nucleophilic conjugate reaction to covalently attach the electron pair accepting moieties to the device surface. The first and second nucleophilic conjugate reactions, when complete, yield a device with a cross-linked biocompatible hydrogel layer covalently attached thereto.

As described, the first and second nucleophilic conjugate reactions may be of the same type with the reactions differing by having different reactants. The two reactions may involve the same electron pair acceptor, such as the biocompatible polymer species comprising an electron pair accepter that can participate in a plurality of reactions. The plurality of reactions may differ by having distinct nucleophilically-reactive parent molecules, in one case, a biocompatible polymer species with a nucleophilic moiety, and in the second case, a device surface with a nucleophilic moiety.

Figure 8:
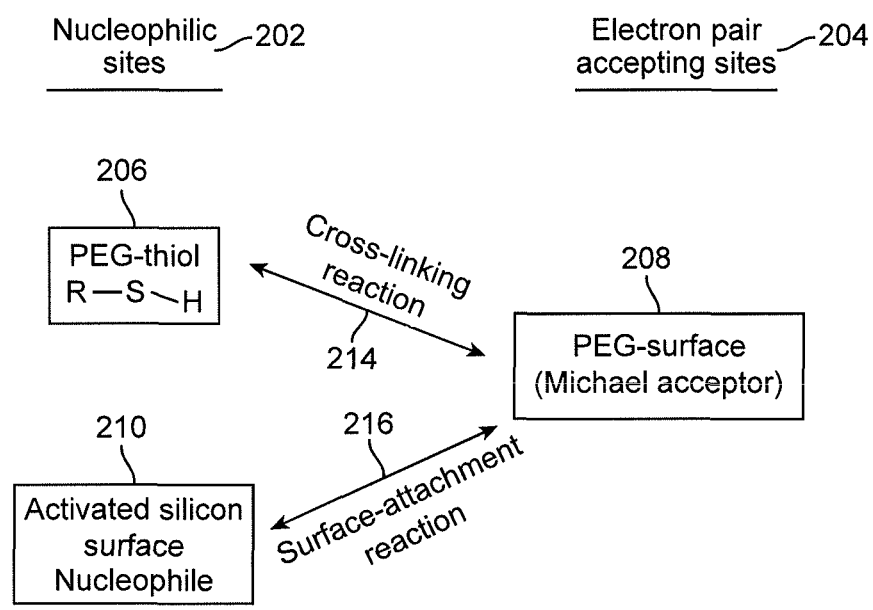
FIG. 8 is a schematic diagram of a first and second reaction with principal reactants.

Referring to FIG. 8, a schematic diagram 200 of two exemplary conjugate addition reactions 214, 216 and the principal reactants are shown. The principal reactants can be understood as nucleophilic moieties 202 and electron pair accepting moieties 204. In a first reaction, a reactant having nucleophilic functional moiety, such as PEG-thiol 206, reacts with a reactant having an electron pair accepting functional moiety 204, such as PEG-sulfone 204; the product of the reaction 214 is a linked pair of PEG molecules, linked by way of a central thioether bond. As the reaction proceeds among the functionalized PEG molecules, the PEG takes the form of a linked network, and inasmuch as a PEG network is biocompatible, in an aqueous environment, the network takes the form of an integrated hydrogel.

In a second reaction 216, a reactant 204 having an electron pair accepting functional moiety, such as PEG-sulfone 204, reacts with a nucleophilic site on the surface of the medical device 210; the product of this second reaction 216 is a covalent bond between the PEG-sulfone and the device. As above, inasmuch as the individual molecular that covalently link to the activated device surface also are included as a constituent of a hydrogel structure, the hydrogel structure, as a whole, becomes covalently linked to the device.

Figure 9A:
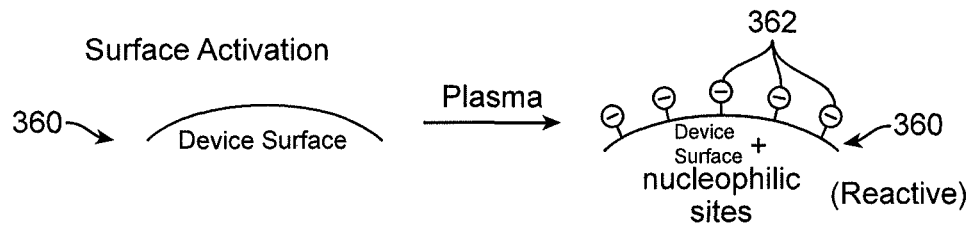
FIGS. 9A-9D show more details of reactants and reactions depicted in FIG. 8.
Figure 9B:
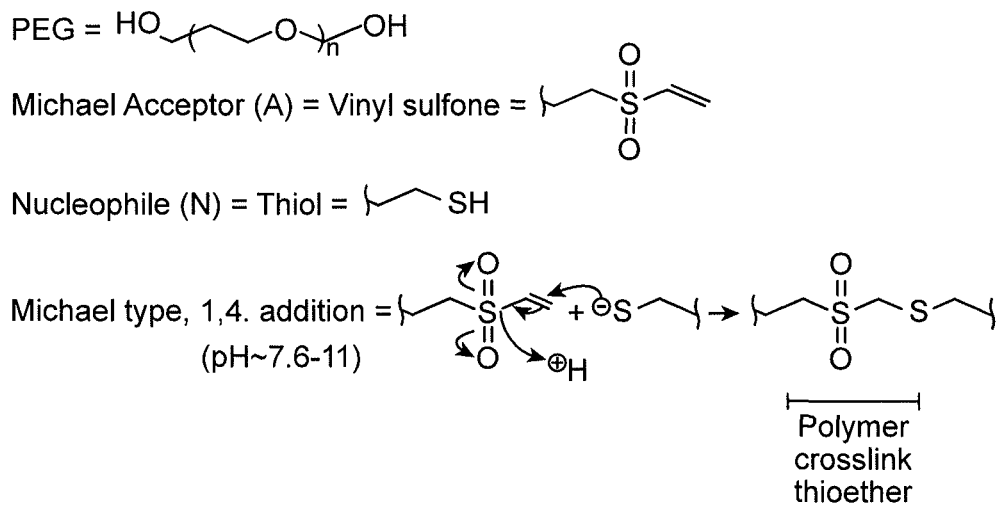

FIG. 9A-9D show more detailed and particular aspects of reactants and reactions, as depicted schematically in FIG. 8. FIG. 9A shows a device surface being activated by a plasma treatment to yield a device surface covered with a bed of activated nucleophilic sites. FIG. 9B shows the structure of examples of reactants, including a PEG molecule, a Michael-Type electron acceptor such as a vinyl sulfone moiety, a nucleophile functional group such as a thiol, and the detail of the Michael type reaction itself.

Figure 9C:
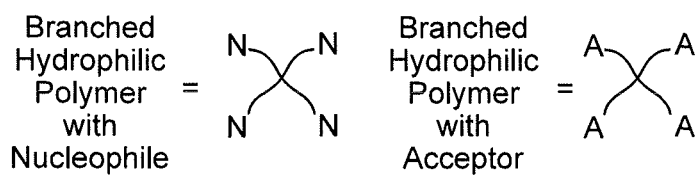
Figure 9D:
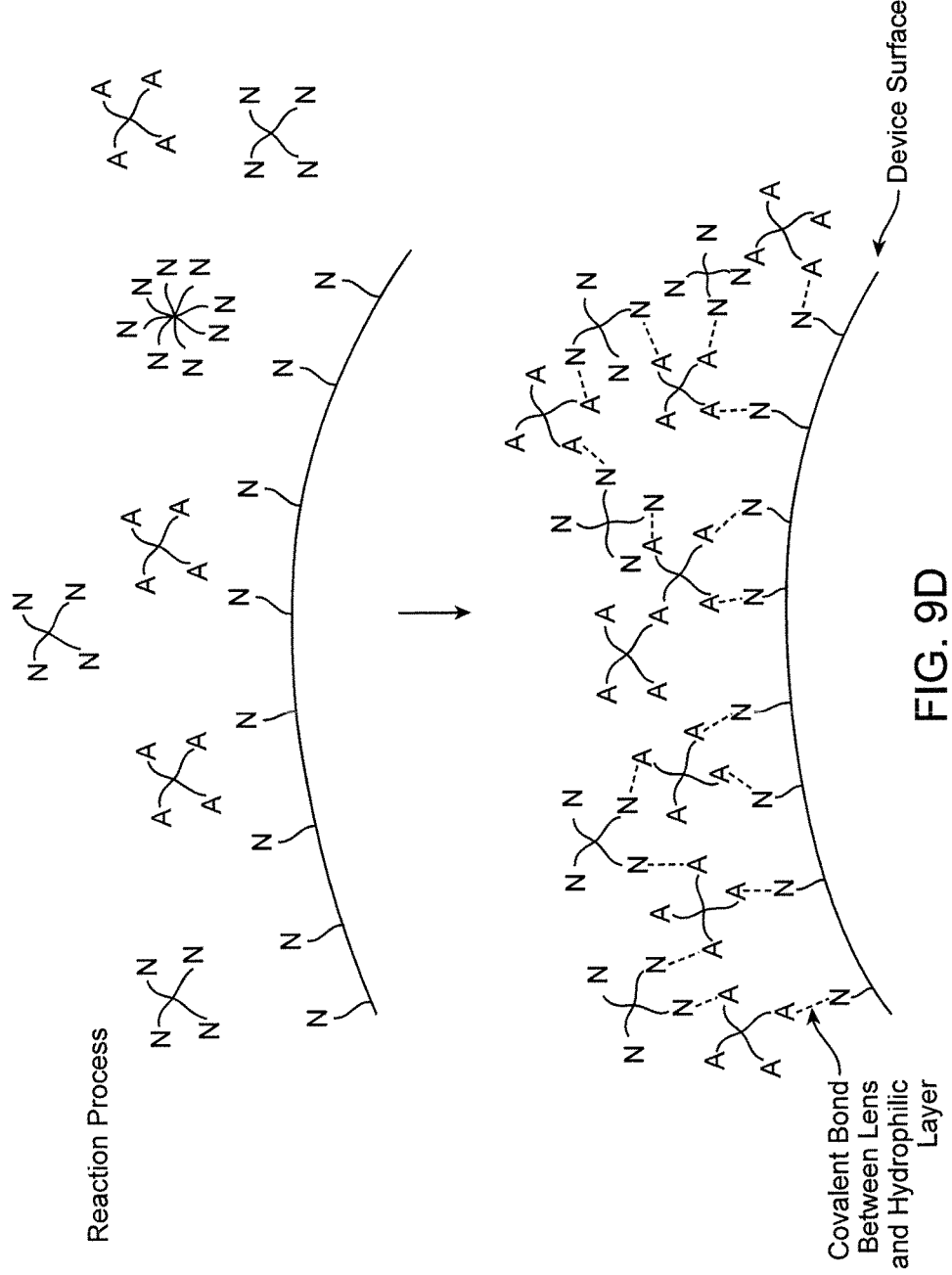

FIGS. 9C-9D show a reaction process whereby two subpopulations of branched biocompatible polymer species, a first subpopulation with a nucleophile functionality (N) and a second subpopulation with an electron pair accepting functionality (A) are in a reaction solution that bathes a nucleophilically activated (N) device. In the lower portion of FIG. 9D, per the first reaction as depicted in FIG. 8, reaction individual members of the two subpopulations have begun to link together by way of their functional groups, to form a hydrogel network. And, per the second reaction as depicted in FIG. 8, electron pair accepting moieties (A) of biocompatible polymers engage in covalent linking with the nucleophilic sites on the device surface, thereby covalently attaching the hydrogel network to the device surface.

Figure 10A:
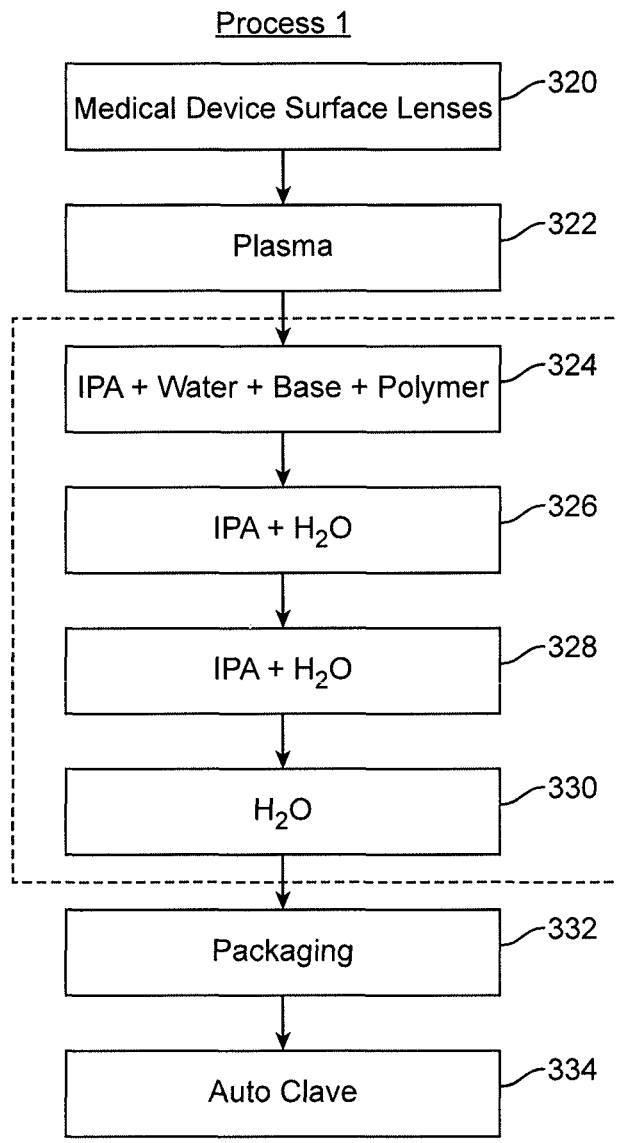
FIGS. 10A-10B are flow diagrams of exemplary methods described.
Figure 10B:
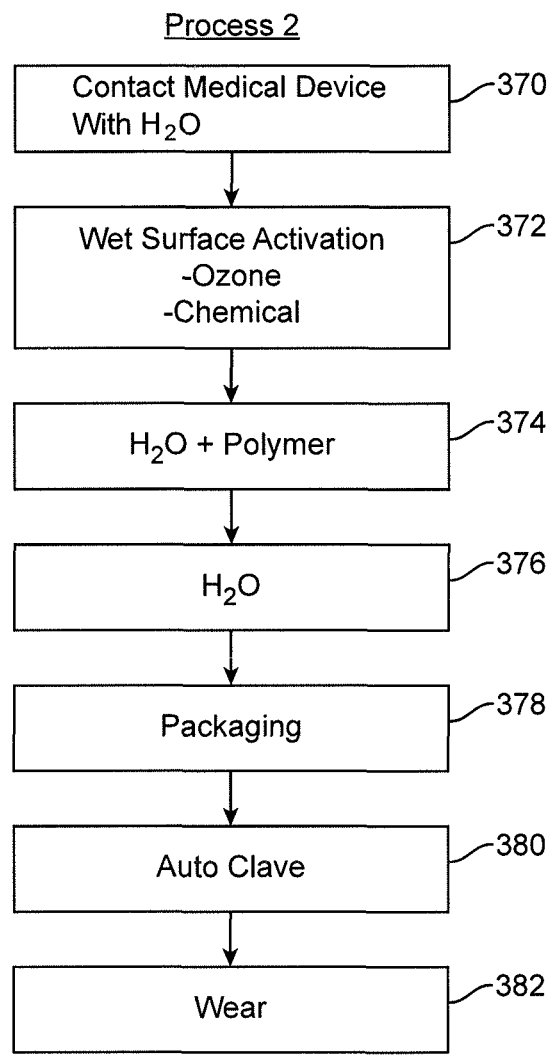

FIGS. 10A-10B provide flow diagrams of two variations of processes for making a device with a covalently attached hydrogel membrane. FIG. 10A shows a process that includes a plasma activation method. Such plasma treatment may include exposure to any of an oxygen plasma or a nitrogen plasma. FIG. 10B shows a process that includes a chemical or "wet" activation method.

As described in FIG. 10A, a medical device surface 320 is plasma treated 322 to form a plurality of reactive sites on the device surface. This may be accomplished by placing the device into a vacuum plasma chamber. In some embodiments, the device is transferred to a holding device, typically metal, and placed in a vacuum plasma chamber.

Referring still to FIG. 10A, after the device surface is activated, the activated device is placed into a solution that includes coating polymer and/or coating polymer species or precursors 324. The coating polymer may be any of the described biocompatible polymers described including a biocompatible polymer population including subpopulations of functionalized branched PEG species. In some cases, the solution also includes isopropyl alcohol and water. The solution may have a pH >7. The solution may be agitated to create a well-stirred bath and the devices incubate in the solution for some period of time. In some cases, the incubation time is about 50 minutes.

Optionally, the coating process may include extraction steps to remove an unwanted component from the device. For example, where a silicone-based lens core is used for a base or substrate, unreacted silicone molecules in the lens cores are extracted or diffused out of the devices. Advantageously, the extraction process removes raw core material (e.g. raw silicone for a silicone-containing core) that may leach out of the device into the body tissues. As such, further steps of the process may include transferring the device to a solution of isopropyl alcohol and water for a period of time such as about 50 minutes 326 to continue extracting unreacted silicone molecules from the devices. Additionally, as a second rinse 328, the device may be transferred to a fresh solution of isopropyl alcohol and water for a period of time such as about 50 minutes to further extract unreacted silicone molecules from the devices. In some variations, the devices may also be transferred into a water bath 330 to equilibrate in water for a period of time (e.g. about 50 minutes).

Additionally, as shown in FIG. 10A, the devices may be transferred to a packaging container with a packaging solution 332. The devices may also be autoclaved 334. In some cases, the device is autoclaved at about 250° F. for about 30 minutes.

FIG. 10B describes a wet-activation process for activating a device and coating the activated device. The process may begin with a medical device in a hydrated state 370. The next step may include activating the hydrated device 372. This may be accomplished by a plasma or chemical treatment. For example, ozone may be used to activate the device surface. Once activated, the activated device may be placed into a solution containing the coating material 374. The solution may include a biocompatible polymer solution as described and water. In some cases, the solution is at a pH >7. The solution may be agitated to create a well-stirred bath and the device incubates therein. In some cases, the device incubates for about 50 minutes.

Next, the device may be transferred to a water bath to equilibrate in water 376. The equilibration step may also serve to wash excess polymer from the device. The device may be equilibrated in water for about 50 minutes. The device may be transferred to a packaging container with packaging solution 378. Additionally, as another step, the device may be autoclaved. In some cases, the device is autoclaved at about 250° F. for about 30 minutes. After the autoclave step, the resulting coated device is ready for use 382.

Advantageously, the methods described herein provide for a cost-effective coating process that can be integrated with device manufacturing processes currently employed in the industry.

Some embodiments of the method may be understood as an immersive method, wherein activated device are immersed in a reaction solution within a stirred vessel, the solution including biocompatible macromer reactants, and the reaction vessel operated to achieve appropriate reaction conditions. The reaction vessel and aspects of the conditions, in biochemical engineering terms, may be understood as occurring in a continuously stirred reaction tank (CSTR). In typical embodiments, the reacting steps occur within a reaction solution that has an aqueous solvent. Such the aqueous solvent may include any one or more of water, methanol, ethanol, or any suitable aqueous solvent that solubilizes PEG.

Figure 11A:
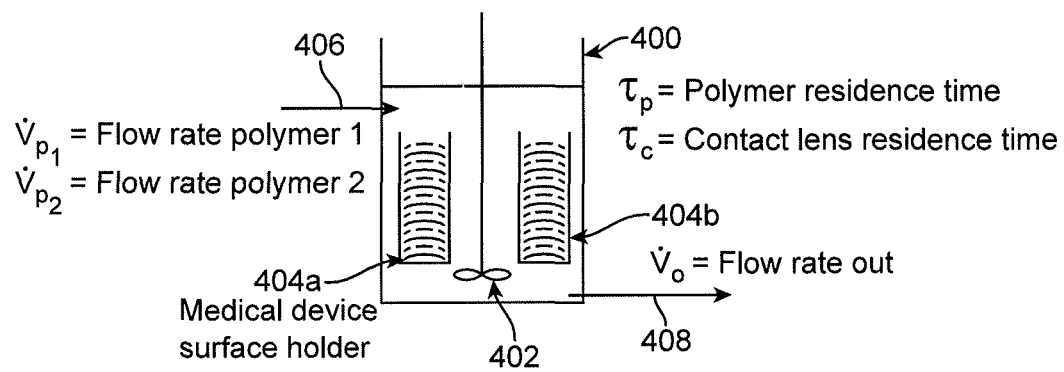
FIGS. 11A-11B show a schematic viewing of a continuously stirred tank reactor.

FIG. 11A provides a schematic view of a continuously stirred tank reactor (CSTR) 400 suitable for performing the reaction described. The CSTR 400 includes an agitator 402 for stirring the reaction contents within the tank. A feeding line or conduit allows input or inflow 406 of reaction solutions including a biocompatible polymer solution containing at least one polymer species. As shown, first and second polymer species flow into the CSTR 400. In some cases, the first and second polymer species have different flow rates VP1 and VP2 respectively. In other cases, the flow rates may be the same.

FIG. 11A shows a plurality of implantable medical devices, such as sensors 404a and 404b in the CSTR 400. In some cases, the implantable medical devices may be held in a mesh holder with openings or sufficient porosity to allow contact between the held implantable medical devices and the solution in the CSTR. The skilled artisan would appreciate that different tank geometries can be used based on the size and shape of the medical device to be coated.

FIG. 11A also shows an output or outflow opening or conduit 408 for removing fluid from the CSTR 400. In some cases, the removed fluid is spent reaction fluid. The flow rate of the removed fluid may be designed as $V_O$.

Figure 11B:
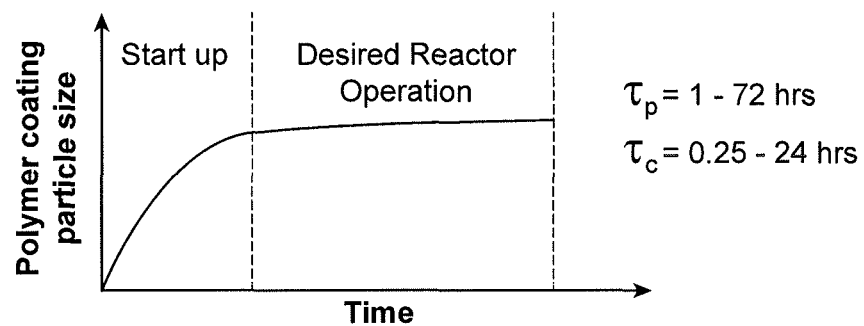

In some cases, $T_P$ indicates the polymer residence time and $T_C$ indicates the contact residence time in the CSTR 400. FIG. 11B shows the relationship between polymer coating particle size as a function of time in a CSTR 400 where $T_P$ is 1-72 hours and $T_C$ is 0.25-24 hours.

In some variations, within the reaction solution, the total biocompatible macromer concentration in the solution typically ranges between about 0.01 (w/v) % and about 0.50 (w/v) %. In some embodiments, the first and second macromer subpopulations are present in the solution at substantially equivalent concentrations. However, in other embodiments, the concentration of the reactive moiety of the second macromer subpopulation (an electron pair accepter) exceeds the concentration of the reactive moiety of first macromer subpopulation (a nucleophile).

Having an excess of electron pair reactive moieties with respect to the nucleophilic reactive moieties can be advantageous for the reactions included herein for the purpose of forming embodiments of hydrogel-coated medical devices in that the electron pair accepting moieties of the biocompatible polymer subpopulation so-functionalized can participate in two reactions. The polymer subpopulation functionalized with the electron pair acceptors participates (1) in covalent cross linking with the subpopulation functionalized with nucleophiles and (2) covalent attachment to nucleophilic sites on the medical device surface. In contrast, the polymer subpopulation functionalized with a nucleophilic moiety engages only in the single reaction wherein it engages the polymer subpopulation functionalized with the electron pair accepting moiety.

The reactant concentration may also be appropriately expressed in terms of the relative concentrations of the reactive moieties of the participant macromers, rather than the concentrations of the macromers themselves. This follows from the possible variations in the degree to which the macromers are decorated with the function moieties that actually participate in the reactions. Accordingly, in some reaction embodiments, the concentration of the reactive moiety of the second macromer subpopulation exceeds the concentration of the reactive moiety of the first macromer subpopulation by at least about 1%. In more particular embodiments, the concentration of the reactive moiety of the second macromer subpopulation exceeds the concentration of the reactive moiety of the first macromer subpopulation by an amount that ranges between about 1% and about 30%. And in still more particular embodiments, the concentration of the reactive moiety of the second macromer subpopulation exceeds the concentration of the reactive moiety of the first macromer subpopulation by an amount that ranges between about 5% and about 20%.

Returning now to aspects of the reaction conditions, in some embodiments, the reacting steps are performed for a duration of between about 5 minutes and about 24 hours. In particular embodiments, the reacting steps are performed for a duration of between about 0.5 hour and about 2 hrs. In some embodiments, the reacting steps are performed at a temperature at a range between about 15° C. and about 100° C. In more particular embodiments, the reacting steps are performed at a temperature at a range between about 20° C. and about 40° C. In some embodiments, the reacting steps are performed at a pH between about 7 and about 11.

In some embodiments, the activated device is incubated in a dilute reaction solution containing 4-arm branched, 10 kDa PEG end functionalized with thiol groups, and 8-arm branched, 10 kDa PEG end functionalized with vinyl sulfone groups. The dilute solution contains between 0.01 and 0.5% total polymer, with a 10% excess of vinyl sulfone groups. The reaction can be performed in aqueous conditions, methanol, ethanol, or other solvents in which PEG is soluble. The reaction can be performed at a range of temperatures between about 15 degrees C. and about 100 degrees C. The reaction can be performed at a range of temperatures between about 20 degrees C. and about 40 degrees C. The reaction can be performed from between about 5 minutes and about 24 hours. The reaction can be performed at basic pH's, preferably in the range of about 5 to about 11. The reaction can be performed at basic pH's, preferably in the range of about 7 to about 11.

As polymer reaction proceeds in the dilute solution, hydrogels (e.g. cross-linked biocompatible polymer particles) are formed as branched polymers react with each other. Reaction progress can be monitored using dynamic light scattering techniques to measure hydrogel particle size and/or macromer aggregation level as the hydrogel network is forming. Temperature, pH, convection speed, and concentration will influence reaction rate and hydrogel particle size and formation rate. Hydrogel particles that are smaller than visible light will not cause optical distortions in the device. Layer thickness can be regulated by monitoring hydrogel formation during the course of reaction.

In some variations, polyethylene glycol is the biocompatible polymer. However, other multifunctional natural and synthetic biocompatible polymers can also be used, for example poly(vinyl alcohol), poly(vinylpyrrolidinone), Poly(N-isopropylacrylamide) (PNIPAM) and Polyacrylamide (PAM), Poly(2-oxazoline) and Polyethylenimine (PEI), Poly(acrylic acid), Polymethacrylate and Other Acrylic Polymers, Polyelectrolytes, hyaluronic acid, chitosan, dextran.

In other embodiments, the methods include the step of forming a cross-linked biocompatible polymer layer on a device surface that is covalently attached to the device. Covalent linkages between the branched biocompatible polymers may occur due to Michael type nucleophilic conjugate addition reaction between vinyl sulfone and thiol and covalent linkages between the biocompatible polymer and the device surface occur due to conjugate addition reaction between vinyl sulfone and nucleophiles generated during the activation step. In some cases, reactivity of nucleophiles will increase with rising pH as molecules are increasingly deprotonated.

In further variations, any general Michael type reaction between enolates and conjugated carbonyls can also be used. For example, acrylate, methacrylate, or maleimide can be substituted for vinyl sulfone. Other examples include the Gilman reagent as an effective nucleophile for addition to conjugated carbonyls. The stork enamine reaction can be performed using enamines and conjugated carbonyls.

Additional covalent reaction mechanisms include hydroxylamine reaction with electrophiles such as aldehyde or ketone to produce oxime linkages.

Additional covalent reaction mechanisms include reaction of N-Hydroxysuccinimidyl esters with amines.

Additional covalent reaction mechanisms include isocyanates reaction with nucleophiles including alcohols and amines to form urethane linkages.

In another embodiment, a PEG containing layer can be attached to a device using cast molding techniques. First, the device is modified to ensure surface groups are present that will react covalently with the PEG macromers. Second, molds are prepared that contain a top part and a bottom part in the same or similar shape as the device. The device is placed into the mold along with the liquid macromer PEG solution and the mold halves are placed together. The PEG can cure thermally for approximately 1 hour and the mold is taken apart.

The PEG containing layer can also be attached to the device using a dip coating method. First, the device is modified to ensure surface groups are present that will react covalently with the PEG macromers. For example, surface groups can be generated in a plasma treatment step, or by incubating in a basic solution, or by including reactive groups in the monomer mix. Next, a dip coating solution is prepared that consists of a dilute solution of reactive, branched, biocompatible polymers. The activated device is placed in the dip coating solution and incubated for 1-24 hours. Following incubation, the device is rinsed thoroughly and then autoclaved in an excess volume of buffer solution prior to measuring captive bubble contact angles.

In alternative method, the biocompatible polymer layer can be covalently attached to the device using another dip coating method. First, the device can be modified to create surface chemical moieties that are covalently reactive to the biocompatible macromers. For example, surface groups can be generated in a plasma treatment step, or by incubating in a basic solution, or by including reactive groups in the monomer mix. Next, a dip coating solution can be prepared that consists of a dilute solution of reactive, branched, biocompatible polymers. For example, the dilute solution can consist of a branched poly(ethylene glycol) end functionalized with vinyl sulfone and thiol in a solution containing 0.2M triethanolamine. The activated device is placed in the dip coating solution and incubated for 1-24 hours at a temperature between about 20° C. and about 60° C. Following incubation, the device is rinsed thoroughly and then autoclaved in an excess volume of phosphate buffered saline.

In an exemplary embodiment, the invention provides a method of making a device described herein. The method comprises contacting an activated device and a dip coating solution, thereby making a device. In an exemplary embodiment, the method further comprises activating a device, thereby creating an activated device. A device can be activated through a method known to one of skill in the art or a method described herein, such as plasma treatment or incubation in a basic solution, or by including reactive groups in the monomer mix. In an exemplary embodiment, the contacting takes place for between 1-24 hours, or from 1-12 hours, or from 12-24 hours, or from 6-18 hours. In an exemplary embodiment, the method further comprises rising the device after the contacting step. In an exemplary embodiment, the method further comprises autoclaving the device after the contacting step. In an exemplary embodiment, the method further comprises autoclaving the device after the rinsing step.

In another embodiment, an alternative method of forming a coated device includes a spray coating approach wherein a reactive ultrasonic spray coating is used to coat substrates with a thin, adhered layer of cross-linked hydrogel. A two-component hydrogel, comprising branched PEG end-capped with vinyl sulfone, and branched PEG end-capped with thiol, was used to produce the cross-linked thin films. The two components are simultaneously dripped onto an ultrasonic spray nozzle where they are combined and atomized into small droplets, which then are accelerated to the substrate in an air sheath. The rate of reaction is adjusted to ensure that reaction is fast enough that a solid structure forms on the surface, but slow enough that the components do not instantly polymerize upon mixing at the nozzle.

An alternative spray method, considered appropriate for scaled manufacturing, is ultrasonic spray coating, a technique that enables precise, thin film coatings. It has been employed previously for stents and in the microelectronics industry, and is currently used in several high volume manufacturing lines. A state of the art Sonotek instrument was used to form coated device prototypes. This technology enables 3D printing, thus potentially providing a platform for constructing complicated device structures with integrated sensors or electronics.

The Sonotek instrument has an ultrasonically driven spray nozzle with two feed lines that deposit solution onto the tip. A two-component hydrogel system involves dissolving the PEG vinyl sulfone component in methanol containing triethanolamine (TEOA; acting as an organic base) and the PEG thiol component in pure methanol. The two solutions are delivered to the nozzle tip at a rate of 5 microliters per minute and the concentration of each PEG component is adjusted such that equal volumes of each component mix to achieve a 10% molar excess of vinyl sulfone groups. When the solutions are deposited on the ultrasonic tip, they mix and are atomized into droplets that are approximately 20 microns in diameter. A pressured air sheath then accelerates the droplets onto the surface to be coated. By including FITC-malelimide in the PEG vinyl sulfone component, mixing and crosslinking that result in film deposition can be films. A concentration of TEOA and identified that at a molar ratio of TEOA:SH of 6:1 could deposit a uniform cross-linked hydrogel on a variety of device substrates. An alternative aqueous spray coating method was also tested and was shown to be feasible, however for the device substrates, the methanol process advantageously produces a highly uniform film of ~5 microns. The contact angle measurements on coated devices demonstrated the integrity of the deposited film.

Figure 12A:
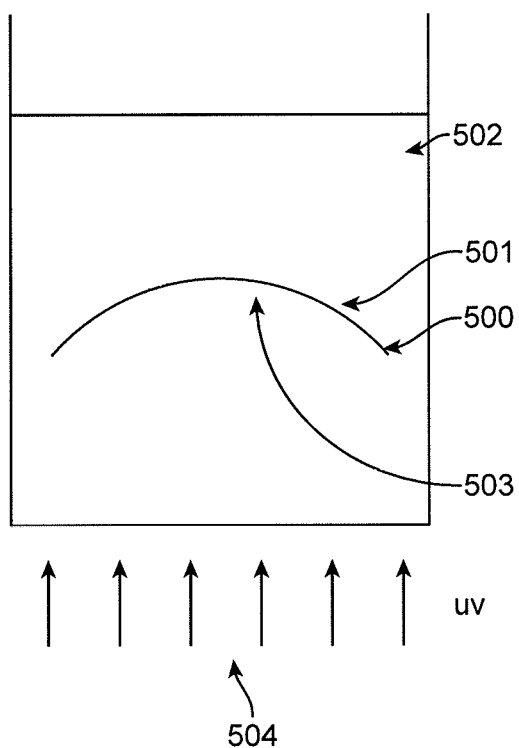
FIGS. 12A-12B show a method of producing lenses with bilateral hydrogel layers differing in depth or composition.
Figure 12B:
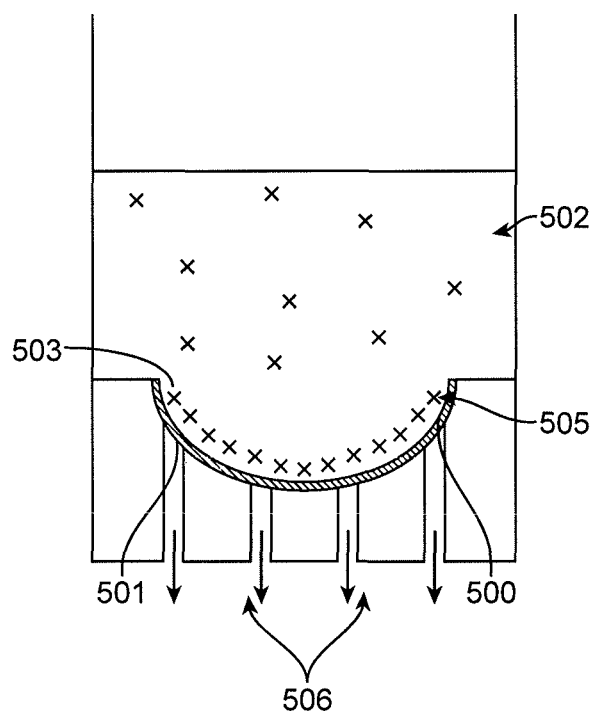
Figure 13:
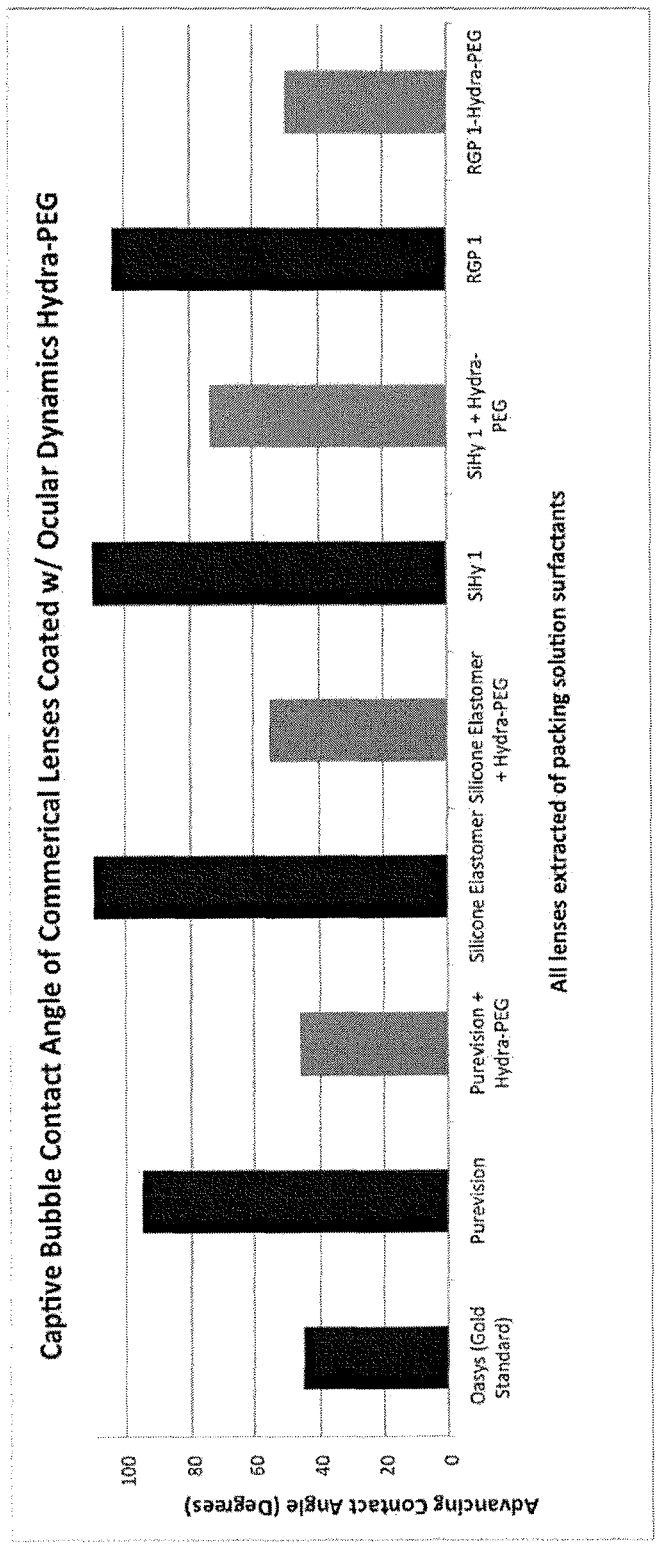
FIG. 13 is a graph illustrating captive bubble contact angle results for coatings applied to various devices in accordance with some embodiments.

FIGS. 12A and 12B depict alternative embodiments of methods of the technology that are directed toward making devices with a covalently attached bilateral hydrogel layer, in which the hydrogel layer sides differ in composition or depth. In some instances, it may be advantageous to produce a device surface that is asymmetric (convex side vs. concave side) with regard to the thickness or composition of the hydrogel coating that is associated with the two surfaces, respectively. For example, it may be advantageous to form a hydrogel layer on the concave (or posterior) device surface that is thicker than the layer on the convex (or anterior) device surface.

FIG. 12A shows a method to produce a device with a thicker biocompatible layer on the concave surface 503 in which a device 500 containing a UV blocking agent is dipped into a non-mixed solution 502 of coating polymer, and then exposed to UV light 504. UV light accelerates the reaction between polymers as well as the reaction between polymer and surface. The light strikes the device on a vector that is perpendicular to the device surface, directly onto the anterior side 503 and through the posterior side 501. Due to the UV blocking agent present in the device, the posterior side 503 is exposed to a higher dose of UV light, while the anterior side 501 receives a relatively lower dose. This asymmetric UV dosing creates layers of varying thickness. To achieve complete independent variation in layer thickness control, light dosage of varying intensity can also be used to shine from each side.

FIG. 12B shows an alternative method for producing a thicker hydrogel layer on the concave surface 503 of the device 500. As shown, the convex surface 501 of the device 500 is held in a vacuum chuck 506 while exposing the concave surface 503 to the coating polymer 502. The vacuum suction pulls the aqueous solvent through the device 500 while concentrating coating polymer at the device interface at the concave surface 503. After achieving a desired layer thickness, the device 500 is removed from the chuck 506. In some variations, the device 500 is then placed into a well-mixed bath of coating polymer, to continue building the hydrogel layer on both sides of the device.

G. Examples

Additional properties of the hydrogel coating and the processes for forming hydrogel coatings are illustrated in the Examples. The processes and properties of the coatings detailed in the Examples are detailed for contact lenses; however, the coating properties and processes are applicable to the additional medical devices disclosed herein. The Examples are not intended to define or limit the scope of the invention.

Example 1

Functionalization of Silicone Hydrogel Lenses. Silicone hydrogel lenses were stored in purified water prior to functionalization. A solution of 10% by volume divinyl sulfone in 0.5M sodium bicarbonate (pH 11) were prepared. Lenses were added to the solution at a ratio of 6 lenses per 10 mL of solution and mixed vigorously on a shake plate for 60 minutes. The lenses were removed, washed in a strainer to remove any excess reaction solution, and added to a container of purified water at a ratio of 1 lens per 20 mL of water. They were mixed vigorously on a shake plate for 60 minutes. The washing procedure was repeated twice more for a total of 3 washes. Next, the lenses were stored in triethanolamine (TEOA) for at least 20 minutes and up to 6 hours prior to attaching the hydrogel layer.

Example 2

Functionalization of Silicone Lenses. Silicone lenses were stored dry prior to functionalization. Lenses were added to a solution of 10% hydrochloric acid and 2% hydrogen peroxide at a ratio of 6 lenses per 10 mL. The lenses were mixed vigorously for 5 minutes and then removed, washed in a plastic strainer to remove any excess reaction solution, and then added to a container of purified water a ratio of 1 lens per 20 mL of water. They were mixed vigorously for 5 minutes. Next the lenses were added to a solution of 95% ethanol, 3% water, 1% glacial acetic acid, and 1% 3-mercaptopropyltrimethoxysilane and mixed vigorously for 60 minutes. The lenses were rinsed in a strainer with pure ethanol and added to a container of pure ethanol at a ratio of 1 lens per 20 mL of ethanol. The lenses were mixed vigorously for 60 minutes. This washing procedure was repeated once more. Finally the lenses were removed from the rinse solution and allowed to dry. They were stored at 4° C. Prior to attaching hydrogel to the lenses, they were immersed in a solution of 150 mM dithiothreitol for 30 minutes and then rinsed in DI water. Following this step, hydrogel must be attached within 15 minutes.

Example 3

Plasma Functionalization of Silicone Containing Layers. Silicone containing layers (silicone or silicone hydrogel) were placed in a vacuum chamber for 2 hours to ensure all moisture was removed. After drying, lenses were inserted into a plasma chamber. Pressure was reduced to 375 milliTorr with continuous flow of nitrogen gas at 10 standard cubic centimeters per minute. The chamber was allowed to stabilize for 30 seconds before initiating plasma at 100 W for 3 minutes. The chamber was then vented to atmosphere and lenses removed. Lenses were then used within 1 hour.

Example 4

Preparation of molds for adding bulk layers to contact lenses. Molds were prepared using silicone hydrogel lenses and agar. 5 grams of Agar were dissolved in 333 mL of water and the solution was heated on a temperature controlled stirred plate until it reaches 88° C. A delrin plate containing small cavities (1" in diameter and 0.5" deep) was used to contain each individual mold. Liquid agar is pipetted to fill a mold cavity half full. A contact lens was then placed, convex side down, on top of the molten agar and additional agar was added on top to completely encase each lens in agar. Each plate contained 12 mold cavities and upon forming all 12, the plate was placed at 4° C. for 10 minutes until it is completely solidified. Once solid, a small brass punch of the same diameter as the contact lens (14 mm) was used to punch a hole in the agar around each lens. A hand held vacuum suction cup was used to pull the top of the agar mold off, tweezers were used to remove the silicone hydrogel lens, and then the top of the mold was replaced. This is repeated for each mold. Molds were then ready to be used for hydrogel attachment.

Example 5

Preparation of poly(ethylene glycol) hydrogel macromer solutions. The PEG hydrogel consists of two components. The first is 8-arm, 10 kDa poly(ethylene glycol) (PEG) end functionalized with vinyl sulfone (PEG-VS). The second is 4-arm, 10 kDa PEG end functionalized with thiol groups (PEG-SH). The PEG-VS was dissolved to 10% w/v in triethanolamine buffer (TEOA) at pH 8.0 and then filter sterilized in a 0.45 micron PVDF filter. The PEG-SH was dissolved to 10% w/v in distilled water and then filter sterilized in a 0.45 micron PVDF filter.

Example 6

Fabrication of a PEG hydrogel. To form a PEG hydrogel, the macromer solutions of Example 5 were mixed together. To achieve varying polymer concentrations, a diluting volume of TEOA was added to the PEG-VS solution prior to mixing. The components were combined together with a 10% molar excess of thiol groups. The table below lists quantities used to fabricate various weight percentage PEG hydrogels. For example, to form a 5% PEG hydrogel: 96 µL of TEOA, was added to 30 µL of PEG-VS in an eppendorf tube. Finally, 66 mL of PEG-SH was added to the tube and it is mixed using a vortex for 3 seconds to ensure complete mixing. The PEG hydrogel was then incubated at 37° C. for 1 hour to ensure complete polymerization.

|  | Volume (µL) | | | |
| --- | --- | --- | --- | --- |
| Hydrogel | TEOA | PEG-VS | PEG-SH | Total |
| 4% | 115.2 | 24.0 | 52.8 | 192.0 |
| 5% | 96.0 | 30.0 | 66.0 | 192.0 |
| 6% | 76.8 | 36.0 | 79.2 | 192.0 |
| 7% | 57.6 | 42.0 | 92.4 | 192.0 |
| 8% | 38.4 | 48.0 | 105.6 | 192.0 |

-continued

| Hydrogel | Volume (µL) | | | |
|---|---|---|---|---|
| | TEOA | PEG-VS | PEG-SH | Total |
| 9% | 19.2 | 54.0 | 118.8 | 192.0 |
| 10% | 0.0 | 60.0 | 132.0 | 192.0 |

Example 7

Determining a non-swelling PEG hydrogel formulation. PEG hydrogel macromer solutions of Example 6 were pipetted between two hydrophobic glass slides separated by a 1 mm spacer and allowed to incubate at 37° C. for 1 hour. To determine swelling ratio, the PEG hydrogel was weighed immediately following polymerization and then immersed in distilled water for 24 hours. The swollen PEG hydrogel was weighed again to determine the amount of water absorbed into the polymer network to determine the mass fold increase. The mass change for all PEG hydrogel formulations was small and the PEG hydrogel formulation of 5% did not undergo any swelling following polymerization.

Example 8

Fabricating a Contact Lens with a bulk layer of PEG Hydrogel on the Concave Side. To produce a contact lens with a bulk layer of PEG hydrogel, the molds of Example 3 were prepared using sacrificial lenses identical to those receiving a bulk layer of PEG hydrogel. A solution of 50% by volume TEOA, 34.4% PEG-SH, and 15.6% PEG-VS were prepared by mixing in an eppendorf tube and vortexing. The top of the agar mold was removed using a small hand held vacuum suction device and the functionalized lens (of either Example 1 or Example 2 or Example 3) were placed into the mold. 20 µL of the mixed PEG solution was placed onto the concave side of the lens, and the top of the agar mold was replaced on top. Air bubbles were removed by gently tapping on the top of the mold until all air was removed from the mold. The mold was placed in an incubator at 37° C. for 1 hour. The lenses were then removed, visually inspected, and placed in purified water for storage.

Example 9

Fabricating a Contact Lens with a bulk layer of PEG Hydrogel on the Convex Side. To produce a contact lens with a bulk layer of PEG hydrogel, the molds of Example 3 were prepared using sacrificial lenses identical to those receiving a bulk layer of PEG hydrogel. A solution of 50% by volume TEOA, 34.4% PEG-SH, and 15.6% PEG-VS were prepared by mixing in an eppendorf tube and vortexing. The top of the agar mold were removed using a small hand held vacuum suction device and 20 µL of the mixed PEG solution was placed into the bottom of the mold. The functionalized lenses (of either Example 1 or Example 2 or Example 3) were placed into the mold and the top of the agar mold was replaced on top. Air bubbles were removed by gently tapping on the top of the mold until all air was removed from the mold. The mold was placed in an incubator at 37° C. for 1 hour. The lenses are then removed, visually inspected, and placed in purified water for storage.

Example 10

Fabricating a Contact Lens with a bulk layer of Hydrogel on both Concave and Convex Sides (Encased). To produce a contact lens encased in a bulk layer of PEG hydrogel, the molds of Example 4 were prepared using sacrificial lenses identical to those receiving a bulk layer of PEG hydrogel. A solution of 50% by volume TEOA, 34.4% PEG-SH, and 15.6% PEG-VS was prepared by mixing in an eppendorf tube and vortexing. The top of the agar mold was removed using a small hand held vacuum suction device and 20 µL of the mixed PEG solution is placed into the bottom of the mold. The functionalized lens (of either Example 1 or Example 2 or Example 3) were placed into the mold and 20 µL of the mixed PEG solution was placed onto the concave side of the lens and then the top of the agar mold was placed on top. Air bubbles were removed by gently tapping on the top of the mold until all air was removed from the mold. The mold was placed in an incubator at 37° C. for 1 hour. The lenses were then removed, visually inspected, and placed in purified water for storage.

Example 11

Oaysys Lenses Encapsulated in PEG Hydrogel. Contact lenses (Acuvue Oaysys, lotrafilcon A) were functionalized according to Example 1. Agar molds were prepared according to Example 4. Lenses were encapsulated according to Example 10.

Example 12

Oaysys Lenses with a bulk layer of PEG Hydrogel. Contact lenses (Acuvue Oaysys, lotrifilcon A) were functionalized according to Example 1. Agar molds were prepared according to Example 4. A bulk layer was added according to Example 8.

Example 13

PureVision Lenses Encapsulated in PEG Hydrogel. Contact lenses (PureVision, balafilcon A) were functionalized according to Example 1. Agar molds were prepared according to Example 4. Lenses were encapsulated according to Example 10.

Example 14

PureVision Lenses with a bulk layer of PEG Hydrogel. Contact lenses (PureVision, balafilcon A) were functionalized according to Example 1. Agar molds were prepared according to Example 4. A bulk layer was added according to Example 8.

Example 15

Silicone Lenses Encapsulated in a bulk layer of PEG Hydrogel. Silicone lenses (NuSil, Med 6755) were functionalized according to Example 2. Agar molds were prepared according to Example 4. Lenses were encapsulated according to Example 10.

Example 16

Silicone Lenses with a bulk layer of PEG Hydrogel on the Concave Side. Silicone lenses (NuSil, Med 6755) were functionalized according to Example 2. Agar molds were prepared according to Example 4. A bulk layer was added according to Example 8.

Example 17

Silicone Lenses with a bulk layer of PEG Hydrogel on the Convex Side. Silicone lenses (NuSil, Med 6755) were functionalized according to Example 2. Agar molds were prepared according to Example 4. A bulk layer was added according to Example 9.

Example 18

Contact Angle Measurement. To measure lens contact angles, the captive bubble technique was used. First, the lens was spun in a vortex in distilled water to remove surface contaminants. The lens was then submerged in distilled water and suspended atop a plate that has a hole through which the convex surface of the lens protrudes downward. An 11/16" diameter stainless steel ball was placed atop the lens to keep it in place when the bubble was applied. Next, the curved tip of a 16 gauge blunt needle was placed just below the surface of the center of the lens. A bubble was then advanced until it makes contact with the lens, at which point the bubble was retracted until it breaks free from either the lens or the needle. A high-definition video camera records the entire procedure, after which an image was saved from the frame immediately preceding the moment the bubble detaches from either the lens or the needle. From this image, the angles between the lens and the bubble on both sides of the bubble were calculated in MATLAB and saved as the contact angles for that lens.

Example 19

Contact Angle Measurement of Oasys Lenses with bulk layers of PEG Hydrogel. The contact angle of lenses of Example 11 were measured according to Example 18.

| Lens with bulk layers of PEG hydrogel | Contact Angle* |
|---|---|
| Lens 1 | 12.3 |
| Lens 2 | 14.6 |
| Lens 3 | 10.7 |
| Average | 12.5 |

*Contact angle is the average of 3 tests

Example 20

Preparation of photo-polymerizable poly(ethylene glycol) hydrogel macromer solutions. The hydrogel consists of two components. The first is 8-arm, 10 kDa poly(ethylene glycol) (PEG) end functionalized with acrylate (PEG-Ac). The second is 4-arm, 10 kDa PEG end functionalized with thiol groups (PEG-SH). The PEG-Ac is dissolved to 10% w/v in triethanolamine buffer (TEOA) at pH 8.0 and then filter sterilized in a 0.45 micron PVDF filter. The PEG-SH is dissolved to 10% w/v in distilled water and then filter sterilized in a 0.45 micron PVDF filter.

Example 21

Fabrication of a photo-polymerizable PEG hydrogel. To form a hydrogel, the macromer solutions of Example 20 are mixed together. To achieve varying polymer concentrations, a diluting volume of TEOA is added to the PEG-Ac solution prior to mixing. The components are combined together with a 10% molar excess of thiol groups. The table below lists quantities used to fabricate various weight percentage hydrogels. For example, to form a 5% PEG hydrogel: 96 μL of TEOA, is added to 30 μL of PEG-Ac in an eppendorf tube. Finally, 66 mL of PEG-SH is added to the tube and it is mixed using a vortex for 3 seconds to ensure complete mixing. The solution is then exposed to UV light (365 nm, 5 mW/cm2, 10 min) to polymerize the mixture.

| Hydrogel | Volume (μL) | | | |
|---|---|---|---|---|
| | TEOA | PEG-Ac | PEG-SH | Total |
| 4% | 115.2 | 24.0 | 52.8 | 192.0 |
| 5% | 96.0 | 30.0 | 66.0 | 192.0 |
| 6% | 76.8 | 36.0 | 79.2 | 192.0 |
| 7% | 57.6 | 42.0 | 92.4 | 192.0 |
| 8% | 38.4 | 48.0 | 105.6 | 192.0 |
| 9% | 19.2 | 54.0 | 118.8 | 192.0 |
| 10% | 0.0 | 60.0 | 132.0 | 192.0 |

Example 22

Layer by Layer Reactive Spin Coating. The macromer solutions of Example 20 are prepared. Lenses of Example 1 or 2 or Example 3 are fixed to a spin coater chuck. The lenses are rotated at speeds ranging from 500-5000 rpms. While revolving, the lens is continuously exposed to UV light (365 nm, 5 mW/cm2), while drops of macromer solution are alternately added to the lenses as follows: 10 μL of PEG-Ac followed by 10 μL of PEG-SH, etc. This is repeated for multiple cycles, ranging from 10-1000.

Example 23

PEG Dipping Solution for Enzyme Mediated Redox Chain Initiation. The PEG dipping solution consists of a mixture of glucose oxidase (GOX), Fe+2, and polyethylene glycol diacrylate (PEGDA) (MW from 2,000 Da-10,000 Da). For example, a dipping solution may contain $3.1 \times 10^{-6}$ M GOX, $2.5 \times 10^{-4}$ M iron (II) sulfate, 10% PEGDA 5,000 Da.

Example 24

Contact Lens Encapsulated in PEG Hydrogel Via Interfacial Enzyme Mediated Redox Chain Initiation. The glucose loaded lenses of Example 18 are dipped into the solution of Example 19 until the hydrogel layer grows to the desired thickness. The time to achieve a layer thickness of 10-100 microns ranges from 2 seconds-10 minutes.

Example 25

Captive Bubble Contact Angle Measurement. A macro lens of 10× magnification was affixed to the camera detailed in Example 17, Contact Angle Measurement. The macro lens enables close-up movies of the bubble/contact lens interface. A syringe pump (New Era Syringe Pump 750) was added to the testing fixture to enable continuous and repeatable bubble control. The pump was programmed using Syringe Pump Pro programming software. A new test fixture chamber was constructed of black acrylonitrile butadiene styrene (abs) to facilitate the use of a thin, clear, glass viewing plate and a semi-opaque background screen. The tested lens were held between two plates and submerged in PBS. An air bubble was extended 2 mm from a straight 16 gage blunt needle until it made contact with the lens. A high-definition web camera recorded the lens+bubble interface while 3 μl of air was infused and then withdrawn at a rate of 7.2 μl/min from the micro-syringe (Precision Sampling corp, series A-2, 25 ul).

Example 26

PEG Concentration Dependence. To determine the effect of PEG concentration on polymerization rate for the hydrogel, the macromer solutions of Example 4 were combined at decreasing concentrations and checked at set time intervals until solidification. PEG-VS and PEG-SH were combined in the below quantities with the specified quantity of 0.2M TEOA in 1.5 ml eppendorf tubes to form the noted concentrations. Each solution was vortexed and then pippted onto a glass slide. The PEG solution was pippetted at 5, 10, or 30 second intervals (increasing time interval for lower concentrations) until filaments formed, indicating that the gel had polymerized. The time-until-polymerization was recorded.

|  |  | PEG Concentration | | | | | | |
| --- | --- | --- | --- | --- | --- | --- | --- | --- |
|  |  | 1% | 2% | 3% | 4% | 6% | 8% | 10% |
| Volume (μL) | PEG-VS | 10.6 | 10.6 | 16.0 | 21.3 | 31.9 | 42.6 | 53.2 |
|  | PEG-SH | 19.4 | 19.4 | 29.0 | 38.7 | 58.1 | 77.4 | 96.8 |
|  | TEOA | 270 | 120 | 105 | 90 | 60 | 30 | 0 |
| Total Volume |  | 300 | 150 | 150 | 150 | 150 | 150 | 150 |
| Polymerization Time (Sec) |  | 8820 | 680 | 406 | 250 | 150 | 103 | 83 |

Example 27

PEG pH Dependence. To determine the polymerization rate of the hydrogel as a function of pH, the macromer solutions of Example 4 were combined with 0.2M TEOA at increasing pH levels. 20% PEG-VS and 10% PEG-SH were combined in the below quantities with TEOA at the specified pH in 1.5 ml eppendorf tubes. The TEOA buffer was prepared at the noted concentrations by adjusting pH with NaOH or HCl as required. A 4% hydrogel solution was made. Each solution was vortexed and then pippted onto a glass slide. The PEG solution was pippetted at 5, 10, or 30 second intervals (increasing time interval for lower pH) until filaments formed, indicating that the gel had polymerized. The time-until-polymerization was recorded.

Example 28

Lenses Dip Coated to Obtain a Bulk Layer of PEG. Lenses were functionalized using nitrogen gas in a plasma chamber (Plasma Etch PE-50) at settings: 375 mTorr, 3 min, 100% RF power. Pressure was reduced to 375 milliTorr with continuous flow of nitrogen gas at 10-20 standard cubic centimeters per minute. The chamber was allowed to stabilize for 30 seconds before initiating plasma at 100 W for 3 minutes. The chamber was then vented to atmosphere and lenses removed. Lenses were then used within 1 hour. The PEG macromer solutions of Example 4 were combined with excess TEOA to obtain solutions with a total solids concentration of 0.1% and 0.5% and with a 10% molar excess of VS (See quantities in table below). A 0% PEG solution was also prepared as a control. The volume of 0.2M TEOA detailed below was added to individual plastic vials (McMaster Carr 4242T83); followed by the noted volume of PEG-VS. The surface functionalized PureVision lenses were added to this solution and vortexed. The PEG-SH was added and the solution was again vortexed. The lenses were placed on a mixing table for 24 hrs. The lenses were transferred to new plastic vials containing Phosphate Buffered Saline (PBS) and placed on the mixing table for 24 hrs. The lenses were transferred to glass jars and autoclaved (Tuttnauer 3870 E) in a wet cycle at 250° F. for 30 min.

|  |  | PEG Concentration | | |
| --- | --- | --- | --- | --- |
|  |  | 0.00% | 0.1% | 0.5% |
| Volume (μL) | PEG-VS | 0.0 | 5.3 | 26.6 |
|  | PEG-SH | 0.0 | 9.7 | 48.4 |
|  | TEOA | 1500 | 1485 | 1425 |
| Total |  | 1500 | 1500 | 1500 |

Example 29

Silicone Lenses Surface Activated to Enhance Hydrogel Adhesion. Silicone lenses (NuSil, Med 6755) were functionalized with the plasma treatment process of Example 28. In a 50 mL conical tube, the lenses were placed in a 10% w/v divinyl sulfone solution with a sodium bicarbonate buffer at pH 11 and vortexed. After 1 hr on a mixing table, the lenses were washed with 20 ml of deionized water (DI Water) and placed back on the mixing table in 40 ml of DI water. After 1 hr, this cycle was repeated once more and the lenses were placed in the fridge for 8 hrs in 40 ml of DI water.

Example 30

Silicone Lenses Dip Coated to Obtain a Bulk Layer of PEG. Silicone lenses (NuSil, Med 6755) were functionalized, dip coated and autoclaved, in the 0%, 0.1%, and 0.5% PEG solutions per Example 28.

Example 31

PureVision Lenses Surface Activated and Dip Coated to Obtain a Bulk PEG Layer. Contact lenses (PureVision, balafilcon A) were functionalized with the plasma treatment process of Example 28. The lenses were placed into 400 uL of 10% PEGVS, vortexed, and then positioned on the mixing table for 5 minutes. Subsequently, the lenses were placed in 3 mL of 0.2M TEOA, vortexed, and set on the mixing table for 5 minutes. The lenses were added to a solution of 0.1% PEG in TEOA according to example 28. The lenses were vortexed, stationed on the mixing table for 24 hrs, and autoclaved according to Example 28.

Example 32

PureVision Lenses Dip Coated with FITC-Maleimide Addition for PEG Layer Visualization. Contact lenses (PureVision, balafilcon A) were functionalized with the plasma treatment process of Example 28. The lenses were placed into 0.1% and 0.5% PEG solutions according to example 28. 5.1 μl of FITC-Maleimide @ 10 mg/mL was added to each of the solutions to visualize the PEG layer. The solutions were vortexed and placed on a mixing table for 24 hrs.

Example 33

PureVision Lenses Dip Coated to Obtain a Bulk Layer of PEG with Shortened Wash Cycle. Contact lenses (PureVision, balafilcon A) were functionalized and coated according to Example 28. After 24 hrs in the PEG solution, the lenses were placed in vials containing PBS and placed on the mixing table for 1.5 hrs. The lenses were placed in a second set of vials containing PBS and placed on the mixing table for 1.5 hrs. The lenses were autoclaved according to Example 28.

Example 34

PureVision Lenses Dip Coated in Ultra-Low Concentration PEG with No Wash Cycle. Contact lenses (PureVision, balafilcon A) were functionalized with the plasma treatment process of Example 28. The macromer solutions of Example 4 were combined with TEOA at 0.01% and 0.05% PEG. A 0% PEG solution was also prepared as a control. The PureVision lenses were added to this solution and vortexed. The PEG-SH was added and the solution was again vortexed. The lenses were autoclaved in individual plastic vials for 30 min at 250° F. without being washed and without being removed from the PEG solution.

|  |  | PEG Concentration | | |
| --- | --- | --- | --- | --- |
|  |  | 0.00% | 0.01% | 0.05% |
| Volume (μL) | PEG-VS | 0.0 | 0.53 | 2.66 |
|  | PEG-SH | 0.0 | .97 | 4.84 |
|  | TEOA | 1500 | 1498.5 | 1492.5 |
|  | Total | 1500 | 1500 | 1500 |

Example 35

PureVision Lenses Dip Coated in Low Concentration PEG with Immediate Autoclave in Glass. Contact lenses (PureVision, balafilcon A) were functionalized and coated according to Example 28. The lenses were placed in glass vials (McMaster-Carr 4417T48) containing 3 ml of PBS and autoclaved according to Example 28.

Example 36

PureVision Lenses Dip Coated and Extracted in Isopropanol Alcohol. Contact lenses (PureVision, balafilcon A) were functionalized and coated at the 0% and 0.5% concentrations according to Example 28. The lenses were placed on a mixing table for 18 hrs. The PEG solution was replaced with pure isopropanol alcohol (IPA) and returned to the mixing table for 1 hr. The IPA was switched and the lenses were washed for an additional hour. The IPA was replaced with deionized water and the lenses were washed for 1 hr. The water was replaced twice and the lenses were washed for 30 min each time. The lenses were placed in PBS and autoclaved per Example 28.

Example 37

PureVision Lenses Dip Coated in Organic Solvents to Obtain Bulk Layer of PEG. 1 ml of pure TEOA was added to 40 ml of isopropyl alcohol (IPA) to make a 0.2M solution. Pure Methanol was added to IPA at 0.2M TEOA to create a 50% solution. 1 ml of concentrated TEOA was dissolved into 40 ml of pure Methanol (MeOH) to form a MeOH at 0.2 Molar TEOA solution. Contact lenses (PureVision, balafilcon A) were functionalized with the plasma treatment process of Example 28. The macromer solutions of Example 4 were combined with the 50% MeOH and 50% IPA at 0.2M TEOA at 0.5% PEG. A 0% PEG solution was also prepared as a control. The macromer solutions of Example 4 were also combined with the MeOH at 0.2 M TEOA at 0.5% PEG. The volume of MeOH and IPA detailed below were added to individual plastic vials; the surface functionalized PureVision lenses were added to the solution and vortexed. The PEG-VS and PEG-SH were added and the solution but the solution was not vortexed due to the sensitivity of the lenses in solvents. The lenses were placed on a mixing table for 18 hrs. A washing series was utilized to remove the organic solvents; the solutions were changed to pure IPA and the lens were placed on the mixing table for 1 hr. The IPA was replaced with deionized (DI) water and the lenses were placed on the mixing table for 1 hr. The DI water was replaced with PBS and the lenses were autoclaved per Example 28.

Example 38

PureVision Lenses with DVS Activation during IPA Solvent Extraction. 1 ml of 100% TEOA was added to 40 ml of isopropyl alcohol (IPA) to make a 0.2M solution. Contact lenses (PureVision, balafilcon A) were functionalized according to Example 28 and placed in 5 ml of IPA at 0.2M TEOA. Non-plasma treated and no-peg lenses were also prepared as controls. 7.5% DVS was added to each vial. The lenses were swirled in the solution and then placed on the mixing table for 1 hour. The DVS was discarded and 40 ml of IPA was added to each solution prior to placing the lenses on the mixing table for 1 hour. The IPA was changed and the lenses were placed on the mixing table for 1 hr. The IPA was replaced with 40 ml of deionized (DI) water and mixed for 1 hr. The DI water was changed and the lenses were mixed for 1 hr. The lenses were dip coated and autoclaved according to Example 28.

Example 39

PureVision Lenses with DVS Activation during MeOH Solvent Extraction. 1 ml of 100% TEOA was added to 40 ml of methanol alcohol (MeOH) to make a 0.2M solution. Contact lenses (PureVision, balafilcon A) were functionalized according to Example 28 and placed in 5 ml of MeOH at 0.2M TEOA. Non-plasma treated and no-peg lenses were also prepared as controls. 7.5% DVS was added to each vial. The lenses were swirled in the solution and then placed on the mixing table for 1 hour. The DVS was discarded and 40 ml of IPA was added to each solution prior to placing the lenses on the mixing table for 1 hour. The IPA was changed and the lenses were placed on the mixing table for 1 hr. The IPA was replaced with 40 ml of deionized (DI) water and mixed for 1 hr. The DI water was changed and the lenses were mixed for 1 hr. The lenses were dip coated and autoclaved according to Example 28.

Example 40

PureVision Lenses Dip Coated in Methanol Solvent to Obtain a Bulk Layer of PEG. Contact lenses (PureVision, balafilcon A) were functionalized according to Example 28. A MeOH at 0.2 Molar TEOA solution was made according to Example 39. The macromer solutions of Example 4 were combined with the MeOH at 0.2 M TEOA at 0.1%, 0.25% and 0.5% PEG. A 0% PEG solution was also prepared as a control. The volume of MeOH detailed below was added to individual glass vials; followed by the noted volume of PEG-VS. The surface functionalized PureVision lenses were added to this solution and vortexed. The PEG-SH was added and the solution was again vortexed. The lenses were placed on a mixing table for 24 hrs.

A MeOH washing cycle was developed and implemented: The MeOH at 0.2 M TEOA and PEG solution was replaced with pure MeOH and the lenses were placed on the mixing table for 1 hr. The MeOH was replaced with IPA and the lenses were placed on the mixing table for 1 hr. The IPA was replaced with a solution consisting of 50% IPA and 50% DI water and the lenses were placed on the mixing table for 1 hr. The 50% solution was replaced with 100% DI water and the lenses were placed on the mixing table for 1 hr. The DI water was replaced with Phosphate Buffered Saline (PBS) and autoclaved according to Example 28.

|  |  | PEG Concentration | | | |
| --- | --- | --- | --- | --- | --- |
|  |  | 0.00% | 0.1% | 0.25% | 0.5% |
| Volume (µL) | PEG-VS | 0.0 | 5.3 | 13.25 | 26.6 |
|  | PEG-SH | 0.0 | 9.7 | 24.25 | 48.4 |
|  | MeOH at 0.2M TEOA | 1500 | 1485 | 1462.5 | 1425 |
|  | Total | 1500 | 1500 | 1500 | 1500 |

Example 41

Plasma Treatment Process. The setting for the plasma treatment process were tested and updated. The plasma treatment process used nitrogen gas, grade 5, in a plasma chamber (Plasma Etch PE-50) with settings: 150 mTorr set point, 200 mtorr vacuum, 3 min, @ 100% RF power. Pressure was reduced to 200 milliTorr with continuous flow of nitrogen gas at 2.5-5 standard cubic centimeters per minute. The chamber was allowed to stabilize for 30 seconds before initiating plasma at 100 W for 3 minutes. The chamber was then vented to atmosphere and lenses removed. Lenses were then used within 1 hour.

Example 42

Lenses Extracted in Isopropanol Alcohol, Desiccated, and Dip Coated. Lenses were placed in 1.5 ml of IPA and set on a mixing table for 18 hrs. The IPA was switched and the lenses were washed for an additional hour. The IPA was replaced with deionized water and the lenses were washed for 1 hr. The water was replaced twice and the lenses were washed for 30 min each time. The lenses were placed in a vacuum chamber and the chamber was evacuated using a pump (Mastercool, 6 cfm) for 24 hrs. The lenses were functionalized and coated at the 0% and 0.5% concentrations according to Example 28 with the plasma treatment process of Example 41. The PEG solution was replaced with deionized water and the lenses were washed for 1 hr. The lenses were placed in PBS and autoclaved per Example 28.

Example 43

PureVision Lenses Dip Coated to Obtain a Bulk Layer of PEG. Example 28 was repeated using the plasma treatment process of Example 41.

Example 44

PureVision Lenses Dip Coated in Low Concentration PEG with Immediate Autoclave in Glass. Example 36 was repeated using the plasma treatment process of Example 41.

Example 45

PureVision Lenses Dip Coated in Organic Solvents to Obtain Bulk Layer of PEG. Example 38 was repeated using the plasma treatment process of Example 41.

Example 46

PureVision Lenses Dip Coated in Methanol Solvent to Obtain a Bulk Layer of PEG. Example 40 was repeated using the plasma treatment process of Example 41.

Example 47

PureVision Lenses Extracted in Isopropanol Alcohol, Desiccated, Dip Coated, with Immediate Autoclave. Contact lenses (PureVision, balafilcon A) were extracted, desiccated, and dip coated according to Example 42. Immediately after the dip coating process the lenses were autoclaved while in the PEG solution according to Example 28.

Example 48

Silicone Lenses Extracted in Isopropanol Alcohol, Desiccated, and Dip Coated. Silicone contact lenses (NuSil, Med 6755) were extracted, desiccated, dip coated and autoclaved according to Example 42.

Example 49

PureVision Lenses Extracted in Isopropanol Alcohol, Desiccated, and Dip Coated. Contact lenses (PureVision, balafilcon A) lenses were extracted, desiccated, dip coated and autoclaved according to Example 42.

Example 50

PureVision Lenses Dip Coated in Methanol Solvent with Heated Rotation to Obtain a Bulk Layer of PEG. Contact lenses (PureVision, balafilcon A) were functionalized using oxygen gas in a plasma chamber (Plasma Etch PE-50) at settings: 200 mTorr, 3 min, 100% RF power. The lenses were dip coated according to Example 40 and placed in a heated oven with rotation at 37° C. for 24 hours. The lenses were washed and autoclaved according to Example 40, but with the following shortened wash times: MeOH 2× quick swirls, IPA 2×20 min, IPA:H20 (50:50) 20 min, H20 10 min, and PBS for autoclave.

Example 51

Silicone Lenses Dip Coated in Methanol Solvent with Heated Rotation to Obtain a Bulk Layer of PEG. Silicone contact lenses (NuSil, Med 6755) were functionalized using oxygen gas in a plasma chamber (Plasma Etch PE-50) at settings: 200 mTorr, 3 min, 100% RF power. The lenses were dip coated according to Example 40 and placed in a heated oven with rotation at 37° C. for 24 hours. The lenses were washed and autoclaved according to Example 40, but with the following shortened wash times: MeOH 2× quirk swirls, IPA 2×20 min, IPA:H20 (50:50) 20 min, H20 10 min, and PBS for autoclave.

Example 52

PureVision Lenses Pre-Activated, Dip Coated in Methanol Solvent with Heated Rotation. Lenses (PureVision, balafilcon A) were functionalized using oxygen gas in a plasma chamber (Plasma Etch PE-50) at settings: 200 mTorr, 3 min, 100% RF power. The lenses were pre-activated with PEG-VS or VS, dip coated according to Example 40 and placed in a heated oven with rotation at 37 C for 24 hours. The lenses were washed and autoclaved according to Example 40, but with the following shortened wash times: MeOH 2× quick swirls, IPA 2×20 min, IPA:H20 (50:50) 20 min, H20 10 min, and PBS for autoclave.

Example 53

Silicone Lenses Dip Coated to Obtain a Bulk Layer of PEG. Example 30 was repeated using the plasma treatment process of Example 41.

Example 54

PureVision Lenses Dip Coated to Obtain a Bulk Layer of PEG using Oxygen Gas. Example 28 was repeated using oxygen gas, grade 5, during the plasma treatment process.

Example 55

PureVision Lenses Plasma Treated and Dip Coated in Hyaluronic Acid to Obtain a Bulk Layer. Contact lenses (PureVision, balafilcon A) were functionalized according to Example 28 with the addition hyaluronic acid (HA) at of 10 mg of hyaluronic acid (HA). Lenses were added to this solution and placed on the mixing table for 1 hr. The HA solution was replaced with DI water and the lenses were placed on a mixing table for 1 hr. The water was replaced and the lenses were placed on a mixing table for 1 hr, 2 additional times. The lenses were placed in individual plastic vials containing 3 ml-5 ml of PBS.

Example 56

PureVision Lenses Plasma Treated and Surface Activated with DVS in NaOH. Contact lenses (PureVision, balafilcon A) were functionalized according to Example 28. 0.5 ml of DVS was added to 4.5 ml of 0.5M Sodium BiCarbonate (NaOH). Lenses were added to this solution and placed on the mixing table for 20 min. Lenses were also placed in 5 ml of NaOH as controls. The solution was replaced with DI water and the lenses were placed on the mixing table for 20 min. This step was repeated 2 additional times.

Example 57

PureVision Lenses Plasma Treated and Dip Coated in Hyaluronic Acid to Obtain a Bulk Layer with a FITC-Maleimide Addition for Layer Visualization. Contact lenses (PureVision, balafilcon A) were functionalized according to Example 28 and dip coated according to Example 55. 51 µl of FITC-Maleimide was added to each of the solutions to visualize the PEG layer. The lenses were washed and stored according to Example 55.

Example 58

PureVision Lenses Plasma Treated and Dip Coated in Hyaluronic Acid in NaOH to Obtain a Bulk Layer. Contact lenses (PureVision, balafilcon A) were functionalized according to Example 28. 5 ml of HA was added to 45 ml of 10M NaOH. 5 ml of HA was added to 45 ml of DI water for a control. Lenses were added to these solutions and placed on the mixing table for 1 hr. The solutions were replaced with DI water and the lenses were placed on the mixing table for 1 hr. The lenses were placed in individual plastic vials containing 3 ml-5 ml of PBS.

Example 59

Silicone Lenses Plasma Treated then Encapsulated in PEG Hydrogel. Silicone lenses (NuSil, Med 6755) were functionalized according to Example 28. Agar molds were prepared according to Example 4. Lenses were encapsulated according to Example 10.

Example 60

PureVision Lenses Plasma Treated and Dip Coated in Low or High Molecular Weight PEG. Contact lenses (PureVision, balafilcon A) were functionalized using monofunctional polyethylene glycol, end functionalized in vinyl sulfone (mPEG-VS). mPEGs of 5 kDa and 20 kDa were used.

5% w/v total mPEG-VS solutions were prepared in triethanolamine buffer (TEOA) at pH 8.0 and then filter sterilized in a 0.45 micron PVDF filter. A 0% PEG solution was also prepared as a control.

3 ml of PEG solution was added to individual plastic vials (McMaster Carr 4242T83). The surface functionalized PureVision lenses were added to this solution and vortexed. The lenses were placed on a mixing table for 24 hrs. The lenses were transferred to new plastic vials containing Phosphate Buffered Saline (PBS) and placed on the mixing table for 24 hrs.

Example 61

Silicone Lenses Plasma Treated then Encapsulated in PEG Hydrogel with a FITC-Maleimide Addition for PEG Layer Visualization. Silicone lenses (NuSil, Med 6755) were functionalized according to Example 28. Agar molds were prepared according to Example 4. 5.1 µl of FITC-Maleimide was added to each of the solutions to visualize the PEG layer. Lenses were encapsulated according to Example 10.

Example 62

Oaysys Lenses Desiccated and Plasma Treated then Encapsulated in PEG Hydrogel. Contact lenses (Acuvue Oaysys, senofilcon A) were desiccated according to Example 42 and functionalized according to Example 28. Agar molds were prepared according to Example 4. Lenses were encapsulated according to Example 10.

Example 62

Lenses Encapsulated in PEG Hydrogel. Lenses (Lotrafilcon B) were functionalized according to Example 1. Agar molds were prepared according to Example 4. Lenses were encapsulated according to Example 10.

Example 63

Lenses Desiccated and Plasma Treated then Encapsulated in PEG Hydrogel. Lenses (Lotrafilcon B) were desiccated according to Example 42 and functionalized according to Example 28. Agar molds were prepared according to Example 4. Lenses were encapsulated according to Example 10.

Example 64

Silicone Lenses Plasma Treated and Dip Coated in Low or High Molecular Weight PEG. Silicone lenses (NuSil, Med 6755) were functionalized according to Example 28, with the addition of a non-plasma treated control, and dip coated according to Example 60.

Example 65

PureVision Lenses Plasma Treated then Encapsulated in PEG Hydrogel. Contact lenses (PureVision, balafilcon A) were functionalized according to Example 28. Agar molds were prepared according to Example 4. Lenses were encapsulated according to Example 10.

Example 66

PureVision Lenses Dip Coated to Obtain a Bulk Layer of PEG. Contact lenses (PureVision, balafilcon A) were functionalized and coated according to Example 28. The lenses were washed according to example 33 and autoclaved according to Example 28.

Example 67

Glucose Loading of Hydrogel Contact Lenses. Hydrogel contact lenses containing acrylate groups on the surface were incubated in d-Glucose solution (10 mL/lens) for at least 4 hours. The glucose concentration may range from 0.1 mM to 25 mM.

Example 68

PureVision Lenses Dip Coated and Accelerated Life Tested to Identify the Stability of the Bulk Layer of PEG. Example 46 was repeated; contact lenses (PureVision, balafilcon A) dip coated in methanol solvent to obtain a bulk layer of peg. Post autoclave process according to Example 28, the lenses were tested according to Example 25. The lenses were placed in PBS and autoclaved once more according to Example 28 or placed in sterile saline (Walgreens—Sterile Saline Solution). The lenses were placed in hybridization ovens (Stovall Life Science Inc) at 20, 40, or 60 degrees Centigrade. The lenses were tested on dates that correspond to six or twelve months of accelerated life testing as detailed by FDA 510K clearance requirements for medical devices generally, and daily wear contacts specifically. Post testing, the sterile saline was replaced with new sterile saline and the lenses were replaced in the respective hybridization oven. Lot numbers with corresponding solutions and temperatures are detailed below.

| 0% PEG n = 6 Temp [C.] | Storage Solution Saline | Sterile Saline |
|---|---|---|
| 20 | M167 | M170 |
| 45 | M168 | M171 |
| 60 | M169 | M172 |

| 0.5% PEG n = 6 Temp [C.] | Storage Solution Saline | Sterile Saline |
|---|---|---|
| 20 | M173 | M176 |
| 45 | M174 | M177 |
| 60 | M175 | M178 |

Example 69

MJS Lenses Dip Coated to obtain a Bulk Layer of PEG. MJS Lenses (MJS Lens Technology Ltd, Standard Product, 55% water content) were functionalized according to Example 41, coated and autoclaved according to Example 28, and tested according to Example 25. The lenses were then placed in hybridization ovens (Stovall Life Science Inc) at 60 degrees Celsius for 7 days. The sterile saline (Walgreens—Sterile Saline Solution) was replaced and the lenses were retested according to Example 25.

Example 70

Determining water content of poly(ethylene glycol) coated contact lenses utilizing mass balance. This example illustrates how to determine the water content of a contact lens of the invention. In an effort to determine the potential water content of the polyethylene-glycol layer(s) of the contact lenses of the invention, samples consisting of the layer components are prepared for evaluation. The resulting gels are then hydrated and tested to determine water content.

PEG hydrogel macromer solutions as described in Example 5 were pipetted between two hydrophobic glass slides separated by a 1 mm spacer and allowed to incubate at 37° C. for 1 hour.

Hydrated samples were blotted dry and the mass at hydrated state was recorded via mass balance. Following the recording of the mass at hydrated state, the samples were all dried under a vacuum of <1 inch Hg overnight.

Dried samples were removed from the vacuum oven after overnight drying and then measured to record dry mass. Water content was calculated using the following relationship: Water content=[(wet mass−dry mass)/wet mass]×100%

Example 71

Preparation of Poly(ethylene glycol) Hydrogel Macromer Solutions. In one example, the PEG hydrogel consists of two components. The first is 8-arm, 10 kDa poly(ethylene glycol) (PEG) end functionalized with vinyl sulfone (PEG-VS). The second is 4-arm, 10 kDa PEG end functionalized with thiol groups (PEG-SH). The PEG-VS was dissolved to 10% w/v in triethanolamine buffer (TEOA) at pH 8.0 and then filter sterilized in a 0.45 micron PVDF filter. The PEG-SH was dissolved to 10% w/v in distilled water and then filter sterilized in a 0.45 micron PVDF filter.

Example 72

Contact Lenses. In another example, the following lenses and materials were each processed through the subsequent examples: Silicone (NuSil, Med 6755); PureVision, balafilcon A; Acuvue Oaysys, senofilcon A; AIR OPTIX, Lotrafilcon B, MJS Lenses, MJS Lens Technology Ltd. All subsequent references to 'lenses', include each of the above lenses and materials.

Example 73

Contact Lenses Dip Coated to Obtain a Bulk Layer of Poly(ethylene glycol) (PEG) Hydrogel. In another example, commercially available and hydrated lenses were washed in deionized water three times for 30 min each time. The lenses were desiccated in a vacuum chamber for 2-24 hrs.

Lens surfaces were functionalized using nitrogen gas in a standard plasma chamber (Plasma etch PE-50) at settings: 200 mTorr, 3 min, 100 W RF power, 5-20 standard cubic centimeters per minute. Lenses were then used within 1 hour.

The PEG macromers were combined with either deionized water (DI Water), Isopropanol Alcohol (IPA), or Methanol (MeOH) @ 0.2M TEOA to obtain solutions with a total solids concentration of 0.1%, 0.25% and 0.5%. Various concentrations of substrates were used; each solution was at a 10% molar excess of VS (See quantities in table below) and a 0% PEG solution was also prepared as a control.

The volume of substrate detailed below was added to individual vials, followed by the noted volume of PEG-VS. The surface functionalized lenses were added to this solution. The PEG-SH was added and the lenses were placed on a mixing table for 1 hr-24 hrs. The lenses were washed individually in the corresponding substrate for 30 min. For the solvent conditions, consecutive 30 min washes were in 100% IPA, 50% IPA in DI Water, and 100% DI Water. Lenses in the aqueous substrate were only washed in 100% DI water.

The lenses were placed in Phosphate Buffered Saline (PBS) and autoclaved in a wet cycle at 250° F. for 30 min. Lens general comfort and contact angle were determined through wear and direct in-house measurement, respectively.

|  |  | PEG Concentration | | | |
| --- | --- | --- | --- | --- | --- |
|  |  | 0.00% | 0.1% | 0.25% | 0.5% |
| Volume (µL) | PEG-VS | 0.0 | 5.3 | 13.25 | 26.6 |
|  | PEG-SH | 0.0 | 9.7 | 24.25 | 48.4 |
|  | DI H20, IPA, or MeOH @ 0.2M TEOA | 1500 | 1485 | 1462.5 | 1425 |
|  | Total | 1500 | 1500 | 1500 | 1500 |

Example 74

Lenses Dip Coated with Recycled PEG. In another example, the steps of above Example 73 were repeated for contact lenses PureVision, balafilcon A, at a 0.4M concentration of TEOA. The PEG from this process was kept. After 24 hrs, a PEG solution was developed using 50% of the original (750 µL) and 50% fresh or non-previously-used PEG. Example 73 was repeated using this PEG solution.

Example 75

Lenses Surface Activated using Hydrogen Peroxide and Dip Coated. In another example, dehydrated contact lenses PureVision, balafilcon A, were placed in commercially available Hydrogen Peroxide for 1 hr. The lenses were washed with DI water for 30 min. The coating, washing, autoclave, and testing process was repeated according to Example 73.

Example 76

Lenses Extracted, Desiccated, and Dip Coated. In another example, lenses were placed in 1.5 ml of IPA or MeOH (solvent) and set on a mixing table for 12-18 hrs. The solvent was switched and the lenses were washed in the corresponding solvent for an additional hour. The solvent was replaced with deionized water and the lenses were washed three times for 30 min to 1 hr each time. The lenses were desiccated in a vacuum chamber for 2-24 hrs.

Lens surfaces were functionalized using nitrogen gas in a standard plasma chamber (Plasma etch PE-50) at settings: 200 mTorr, 3 min, 100 W RF power, 5-20 standard cubic centimeters per minute. Lenses were then used within 1 hour. The lenses were coated, washed, autoclaved, and tested according to the aqueous process of Example 73.

Example 77

Lenses Dip Coated and Accelerated Life Tested to Identify the Stability of the Bulk Layer of PEG. In another example, the steps of Example 73 were repeated; for contact lenses (PureVision, balafilcon A and MJS Lens Technology Ltd). Post autoclave and testing process, the lenses were placed in PBS and autoclaved once more or placed in sterile saline. The lenses were placed in hybridization ovens (Stovall Life Science Inc) at 20, 40, or 60 degrees Centigrade. The lenses were tested on dates that correspond to six or twelve months of accelerated life testing as detailed by FDA 510K clearance requirements for medical devices generally, and daily wear contacts specifically. Post-testing, the sterile saline was replaced with new sterile saline and the lenses were replaced in the respective hybridization oven.

Example 78

Coating Characterized via Captive Bubble Contact Angle Testing. In another example, to measure lens contact angles, the captive bubble technique was used. The lens was loaded onto a small plate with a bulbous feature. The lens was submerged in PBS and suspended atop a plate that has a hole through which the convex surface of the lens protrudes downward. A blunt needle was placed just below the surface of the center of the lens. A bubble was then advanced with a syringe pump until it makes contact with the lens, at which point the bubble was retracted until it breaks free from either the lens or the needle. Through a magnifying lens, a high-definition video camera records the entire procedure, after which an image was saved from the frame immediately preceding the moment the bubble detaches from either the lens or the needle. From this image, the angles between the lens and the bubble on both sides of the bubble were calculated in MATLAB and saved as the contact angles for that lens.

Example 79

Lubricity Test Method

A test method was designed and built to observe the affects that the hydrogel coating has on the lubricity of the lens. Three contact lenses were used in this evaluation:
1. Packaged silicone hydrogel lens A
2. Hydrogel coated silicone hydrogel lens A
3. Packaged silicone hydrogel lens B 6 sec A borosilicate glass plate was cleaned and submerged in a tank of PBS. One end of the plate was raised 30 mm with a shim to create a ramp with an angle of ~11 degrees. The test lenses were placed at the top of the ramp and weighted down with a stainless steel bolt, weighting approximately 1.13 grams. The lenses were allowed to slide down the ramp ~152 mm and the time required to reach the bottom of the ramp was recorded. Results:

| Lens Type | Time to Slide (sec) |
|---|---|
| Packaged silicone hydrogel lens A | Lens allowed to slide for X seconds but only slid down X mm |
| Hydrogel coated silicone hydrogel lens A | 2 second |
| Packaged silicone hydrogel lens B 6 sec | 6 seconds |

The results of the tests demonstrate a significant increase in lubricity of the lens coated with hydrogel as compared with the uncoated control.

Many of the above examples focus on applying a hydrophilic coating to a contact lens or lens core. However, the methods for applying the hydrophilic coatings can be applied to a variety of other surfaces disclosed herein using similar process conditions and steps. The hydrophilic layers applied to non-contact lens materials can have similar properties, such as compositions, thicknesses, covalently bonding to the surface, and cross-linking as the hydrophilic coatings applied to the contact lens or lens core.

Example 80

A catheter shaft is processed in accordance with the processes described herein to form a hydrophilic hydrogel coating on the outer surface of the catheter shaft.

Example 81

A stent is processed in accordance with the processes described herein to form a hydrophilic hydrogel coating on the stent surface.

Example 82

An implantable glucose sensor is processed in accordance with the processes described herein to form a hydrophilic hydrogel coating on the outer surface of the implantable glucose sensor.

Example 83

An implantable pacemaker is processed in accordance with the processes described herein to form a hydrophilic hydrogel coating on the outer surface of the pacemaker.

Example 84

Preparation of Polymer Solutions

The coating solution included two components. The first component was a poly(ethylene glycol) (PEG) molecule end functionalized with vinyl sulfone groups. The second component was a polyacrylamide molecule with pendant amine functional groups. The polymer solutions were prepared at a concentration of 2.5% in deionized water and then filter sterilized through a 0.45 micron PVDF filter.

Example 85

Preparation of Polymer Solutions

The coating solution included two components. The first component was A poly(ethylene glycol) (PEG) molecule end functionalized with succinimidyl ester groups. The second component was a polyacrylamide molecule with pendant amine functional groups. The polymer solutions were prepared at a concentration of 2.5% in deionized water and then filter sterilized through a 0.45 micron PVDF filter.

Example 86

Preparation of Polymer Solutions

The coating solution included two components. The first component was a poly(ethylene glycol) (PEG) molecule end functionalized with vinyl sulfone groups. The second component was a polyacrylamide molecule with pendant thiol functional groups. The polymer solutions were prepared at a concentration of 2.5% in deionized water and then filter sterilized through a 0.45 micron PVDF filter.

Example 87

Coating a Titanium Surface

A PEG and PAM polymer solution was used to coat a titanium surface. A plasma treatment was applied to the titanium surface as described herein. The polymer solution was applied to the titanium surface after the plasma surface treatment. The polymer solution was applied through a Click reaction as described herein to deposit a hydrophilic layer comprising PEG and PAM species covalently bound to the titanium surface through the reactive surface sites created by the plasma surface treatment.

Example 88

Coating a Stainless Steel Surface

A PEG and PAM polymer solution was used to coat a stainless steel surface. A plasma treatment was applied to the stainless steel surface as described herein. The polymer solution was applied to the stainless steel surface after the plasma surface treatment. The polymer solution was applied through a Click reaction as described herein to deposit a hydrophilic layer comprising PEG and PAM species covalently bound to the stainless steel surface through the reactive surface sites created by the plasma surface treatment.

Example 89

Coating a Polypropylene Surface

A PEG and PAM polymer solution was used to coat a polypropylene surface. A plasma treatment was applied to the polypropylene surface as described herein. The polymer solution was applied to a polypropylene surface after the plasma surface treatment. The polymer solution was applied through a Click reaction as described herein to deposit a hydrophilic layer comprising PEG and PAM species covalently bound to the polypropylene surface through the reactive surface sites created by the plasma surface treatment.

Example 90

Coating a Polyamide Surface

A PEG and PAM polymer solution was used to coat a polyamide surface. A plasma treatment was applied to the polyamide surface as described herein. The polymer solution was applied to a polyamide surface after the plasma surface treatment. The polymer solution was applied through a Click reaction as described herein to deposit a hydrophilic layer comprising PEG and PAM species covalently bound to the polyamide surface through the reactive surface sites created by the plasma surface treatment.

Example 91

Coating a Polyester Surface

A PEG and PAM polymer solution was used to coat a polyester surface. A plasma treatment was applied to the polyester surface as described herein. The polymer solution was applied to a polyester surface after the plasma surface treatment. The polymer solution was applied through a Click reaction as described herein to deposit a hydrophilic layer comprising PEG and PAM species covalently bound to the polyester surface through the reactive surface sites created by the plasma surface treatment.

Example 92

Coating a Pebax Surface

A PEG and PAM polymer solution was used to coat a pebax surface. A plasma treatment was applied to the pebax surface as described herein. The polymer solution was applied to a pebax surface after the plasma surface treatment. The polymer solution was applied through a Click reaction as described herein to deposit a hydrophilic layer comprising PEG and PAM species covalently bound to the pebax surface through the reactive surface sites created by the plasma surface treatment.

Example 93

Coating a Nylon Surface

A PEG and PAM polymer solution was used to coat a nylon surface. A plasma treatment was applied to the nylon surface as described herein. The polymer solution was applied to a nylon surface after the plasma surface treatment. The polymer solution was applied through a Click reaction as described herein to deposit a hydrophilic layer comprising PEG and PAM species covalently bound to the nylon surface through the reactive surface sites created by the plasma surface treatment.

Example 94

Coating a Nitinol Surface

A PEG and PAM polymer solution was used to coat a nitinol surface. A plasma treatment was applied to the nitinol surface as described herein. The polymer solution was applied to a nitinol surface after the plasma surface treatment. The polymer solution was applied through a Click reaction as described herein to deposit a hydrophilic layer comprising PEG and PAM species covalently bound to the nitinol surface through the reactive surface sites created by the plasma surface treatment.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A medical device comprising:
    an outer surface; and
    a hydrogel layer covalently attached to at least a portion of the outer surface, the hydrogel layer adapted to contact a body tissue or fluid, wherein the hydrogel layer comprises a biocompatible polymer population comprising:
        a first hydrophilic polymer species comprising polyethylene glycol (PEG) having between two to twelve branch arms, wherein at least a subset of the branch arms comprises a reactive sulfonyl group, and
        a second hydrophilic polymer species comprising polyacrylamide having one or more pendant reactive nucleophilic groups,
    wherein the reactive sulfonyl group of at least one of the subset of the branch arms of the PEG is reacted with the one or more pendant reactive nucleophilic groups of the polyacrylamide to at least partially covalently link the PEG to the polyacrylamide.

2. The device of claim 1, wherein the device is configured to be implantable within a mammalian body.

3. The device of claim 2, wherein the device is a stent configured to keep a cavity open.

4. The device of claim 3, wherein the stent is configured to keep a blood vessel, bile duct, intestine, nasal passage or cavity, sinus cavity, or intraocular channel open.

5. The device of claim 2, wherein the device is a sensor, camera, vital sign monitor, drug depot device, neurostimulator, ultrasound, silicone implant, saline implant, hernia mesh, penile implant, orthopedic rod or plate or pin or nails, pacemaker, cardiac valve, ear tube, aneurysm coil, or intraocular lens.

6. The device of claim 1, wherein the device is a test strip.

7. The device of claim 6, wherein the device is a drug, salivary, urine, blood or semen test strip.

8. The device of claim 1, wherein the device is a tool configured to be inserted within a mammalian body.

9. The device of claim 8, wherein the device is a catheter, trocar, endoscope, or laparoscope.

10. The device of claim 1, wherein the device is configured to be used externally on a mammalian body.

11. The device of claim 10, wherein the device is configured for use as a bandage, wound dressing, external sensor, hearing aid, or artificial skin.

12. The device of claim 1, wherein the outer surface of the device comprises one or more of: glass, plastic, titanium, nitinol, polyethylene, polypropylene, polyvinyl chloride, polytetrafluoroethylene, polydimethylsiloxane, polyethylene terephthalate, polyamides, polyether urethane, polyether urethane urea, polystyrene, polycarbonate, polysulfones, polymethyl methacrylate, poly 2-hydroxyethylmethacrylate, polyvinylalcohol, polyglycolic acid, polycaprolactone, polylactic acid, polyortho ester, cellulose acetate, collagen, or silk.

13. The device of claim 1, wherein the outer surface of the device consists essentially of a material selected from the group consisting of: glass, plastic, titanium, nitinol, polyethylene, polypropylene, polyvinyl chloride, polytetrafluoroethylene, polydimethylsiloxane, polyethylene terephthalate, polyamides, polyether urethane, polyether urethane urea, polystyrene, polycarbonate, polysulfones, polymethyl methacrylate, poly 2-hydroxyethylmethacrylate, polyvinylalcohol, polyglycolic acid, polycaprolactone, polylactic acid, polyortho ester, cellulose acetate, collagen, or silk.

14. The device of claim 1, wherein the one or more reactive nucleophilic groups is selected from the group consisting of: amines, amino-reactive groups, sulfhydryl, sulfhydryl-reactive groups, carboxyl groups, hydroxyl groups, haloalkyl groups, dienophile groups, aldehyde or ketone groups, alkenes, epoxides, and phosphoramidites.

15. The device of claim 1, wherein the reactive sulfonyl group of a second subset of the branched arms of the PEG is covalently linked to the outer surface of the device.

16. The device of claim 1, wherein the hydrogel layer substantially surrounds the outer surface of the device.

17. The device of claim 1, wherein the hydrogel layer or the hydrogel layer and device are substantially optically clear.

18. The device of claim 1, wherein the hydrogel layer is adapted to allow optical transmission through the hydrogel layer to the device.

19. The device of claim 1, wherein the hydrogel layer is adapted to attenuate x-ray transmission.

20. The device of claim 1, wherein the hydrogel layer is adapted to enable diffusion of biologic molecules, glucose, solutes, polymers, drugs.

21. The device of claim 1, wherein the hydrogel layer comprises a thickness between about 5 nm to about 30 nm.

22. The device of claim 1, wherein the hydrogel layer comprises a thickness below about 100 nm.

23. The device of claim 1, wherein the hydrogel layer comprises a thickness less than about 50 nm.

24. The device of claim 1, wherein the hydrogel layer comprises a thickness less than about 1 micron.

25. The device of claim 1, wherein the hydrogel layer comprises a maximum thickness of about 10 microns.

26. The device of claim 1, wherein a first portion of the hydrogel layer comprises a first thickness different from a second thickness of a second portion of the hydrogel layer.

27. The device of claim 1, wherein the hydrogel layer has a lower coefficient of friction than an underlying device surface.

28. The device of claim 1, wherein the hydrogel layer has a relative protein resistance compared to an underlying device surface.

29. The device of claim 1, wherein the hydrogel layer comprises between about 80% to about 98% water by weight.

* * * * *